(12) United States Patent
Wang et al.

(10) Patent No.: US 9,974,290 B2
(45) Date of Patent: May 22, 2018

(54) ANIMAL MODEL AND METHOD FOR STUDYING GENE-GENE INTERACTIONS

(71) Applicants: Jia-Wang Wang, Tampa, FL (US); Richard F. Lockey, Tampa, FL (US)

(72) Inventors: Jia-Wang Wang, Tampa, FL (US); Richard F. Lockey, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days. days.

(21) Appl. No.: 15/132,125

(22) Filed: Apr. 18, 2016

(65) Prior Publication Data

US 2016/0302398 A1 Oct. 20, 2016

Related U.S. Application Data

(60) Provisional application No. 62/149,330, filed on Apr. 17, 2015.

(51) Int. Cl.
*A01K 67/027* (2006.01)
*C12N 15/85* (2006.01)
*C07K 14/47* (2006.01)
*C07K 14/705* (2006.01)
*C12Q 1/68* (2018.01)
*G01N 15/14* (2006.01)
*G01N 15/00* (2006.01)
*G01N 15/10* (2006.01)

(52) U.S. Cl.
CPC ...... *A01K 67/0278* (2013.01); *A01K 67/0275* (2013.01); *C07K 14/4718* (2013.01); *C07K 14/705* (2013.01); *C12N 15/8509* (2013.01); *C12Q 1/6876* (2013.01); *C12Q 1/6897* (2013.01); *G01N 15/14* (2013.01); *A01K 2217/072* (2013.01); *A01K 2217/077* (2013.01); *A01K 2217/15* (2013.01); *A01K 2217/20* (2013.01); *A01K 2217/206* (2013.01); *A01K 2227/105* (2013.01); *A01K 2267/0325* (2013.01); *A01K 2267/0393* (2013.01); *C12N 2015/859* (2013.01); *C12N 2015/8563* (2013.01); *C12N 2800/30* (2013.01); *C12N 2800/80* (2013.01); *C12Q 2600/154* (2013.01); *C12Q 2600/156* (2013.01); *C12Q 2600/158* (2013.01); *G01N 15/1459* (2013.01); *G01N 2015/0065* (2013.01); *G01N 2015/1006* (2013.01)

(58) Field of Classification Search
CPC ............ A01K 67/0278; A01K 67/0275; A01K 2217/072; A01K 2217/077; A01K 2217/15; A01K 2217/20; A01K 2227/105; A01K 2267/0393; C12N 15/8509; C12N 2015/859; C12N 2800/30; C12N 2800/80
USPC ..................... 800/13, 18; 435/325
See application file for complete search history.

(56) References Cited

U.S. PATENT DOCUMENTS 7,704,963 B2 4/2010 Kerr et al.

FOREIGN PATENT DOCUMENTS

WO WO 2001/038557 5/2001

OTHER PUBLICATIONS

Steck et al. (2011) Clin. Chem., vol. 57(2) 176-185.*
Brunetti et al. (2014) World J. Diabetes, vol. 5920,128-140.*
King et al. (2012) Brit. J. Pharmacol., vol. 166, 877-894.*
Cai et al. (2013) Nature Methods, vol. 10(6) 540-548.*
Tasic et al. (2012) PLoS One, vol. (7(3):e33332, pp. 1-15.*
Aghajani, K. et al. Generation of CD4CreER(T(2)) transgenic mice to study development of peripheral CD4-T-cells. *Genesis* 50, 908-13 (2012).
Alangari, A. et al. LPS-responsive beige-like anchor (LRBA) gene mutation in a family with inflammatory bowel disease and combined immunodeficiency. *J Allergy Clin Immunol* 130, 481-8 e2 (2012).
Arnedo, J. et al. Uncovering the Hidden Risk Architecture of the Schizophrenias: Confirmation in Three Independent Genome-Wide Association Studies. *Am J Psychiatry in Advance*, 1-15 (2014).
Baudouin, S.J. et al. Shared synaptic pathophysiology in syndromic and nonsyndromic rodent models of autism. *Science* 338, 128-32 (2012).
Beck, J.A. et al. Genealogies of mouse inbred strains. *Nat Genet* 24, 23-5 (2000).
Belizario, J.E. The humankind genome: from genetic diversity to the origin of human diseases. *Genome* 56, 705-16 (2013).
Bottcher, R. et al. Efficient chromosomal gene modification with CRISPR/cas9 and PCR-based homologous recombination donors in cultured *Drosophila* cells. *Nucleic Acids Res* 42, e89 (2014).
Bryant, C.D. et al. Behavioral differences among C57BL/6 substrains: implications for transgenic and knockout studies. *J Neurogenet* 22, 315-31 (2008).
Burns, S.O. et al. LRBA gene deletion in a patient presenting with autoimmunity without hypogammaglobulinemia. *J Allergy Clin Immunol* 130, 1428-32 (2012).
Cai, D. et al. Improved tools for the Brainbow toolbox. *Nat Methods* 10, 540-7 (2013).
Chalfin, L. et al. Mapping ecologically relevant social behaviours by gene knockout in wild mice. *Nat Commun* 5, 4569 (2014).
Choe, J. A Dual-fluorescence Reporter System for High-throughput Clone Characterization and Selection by Cell Sorting. *Nucleic Acids Research* 33.5, E49 (2005).
Cong, L. et al. Multiplex genome engineering using CRISPR/Cas systems. *Science*, 339, 819-23 (2013).
Cost, G.J. Enzymatic ligation assisted by nucleases: simultaneous ligation and digestion promote the ordered assembly of DNA. *Nat Protoc* 2, 2198-202 (2007).
Cunningham-Rundles, C. Human B cell defects in perspective. *Immunol Res* 54, 227-32 (2012).

(Continued)

*Primary Examiner* — Anne Marie S Wehbe
(74) *Attorney, Agent, or Firm* — Saliwanchik, Lloyd & Eisenschenk

(57) ABSTRACT

The invention concerns a non-human animal model useful for sensitively studying gene-gene interactions over a wide genetic background; methods for producing the animal model; and methods for studying gene-gene interactions using an animal model of the invention.

19 Claims, 27 Drawing Sheets
(19 of 27 Drawing Sheet(s) Filed in Color)

(56) References Cited

OTHER PUBLICATIONS

De Gasperi, R. et al. The IRG Mouse: A Two-color Fluorescent Reporter for Assessing CRE-mediated Recombination and Imaging Complex Cellular Relationships in Situ. *Genesis*46.6, 308-17 (2008).

De Souza, N. et al. SEL-2, the C. elegans neurobeachin/LRBA homolog, is a negative regulator of lin-12/Notch activity and affects endosomal traffic in polarized epithelial cells. *Development* 134, 691-702 (2007).

Dean, K.M. et al. Advances in fluorescence labeling strategies for dynamic cellular imaging. *Nat Chem Biol* 10, 512-23 (2014).

Doetschman, T. Influence of genetic background on genetically engineered mouse phenotypes. *Methods Mol Biol* 530, 423-33 (2009).

Donoho, G. et al. Analysis of gene targeting and intrachromosomal homologous recombination stimulated by genomic double-strand breaks in mouse embryonic stem cells. *Mol Cell Biol* 18, 4070-8 (1998).

Drumm, M.L. et al. Genetic modifiers of lung disease in cystic fibrosis. *N Engl J Med* 353, 1443-53 (2005).

Erard, M. et al. Minimum set of mutations needed to optimize cyan fluorescent proteins for live cell imaging. *Mol Biosyst* 9, 258-67 (2013).

Espinosa, J.S. et al. Mosaic analysis with double markers (MADM) in mice. *Cold Spring Harb Protoc* 2014, 182-9 (2014).

Ewald, D. et al. Time-sensitive reversal of hyperplasia in transgenic mice expressing SV40 T antigen. *Science* 273, 1384-6 (1996).

Feil, S. et al. Inducible Cre mice. *Methods Mol Biol* 530, 343-63 (2009).

Franklin, C.L. Microbial considerations in genetically engineered mouse research. *ILAR J* 47, 141-55 (2006).

Fu, Y. et al. High-frequency off-target mutagenesis induced by CRISPR-Cas nucleases in human cells. *Nat Biotechnol* 31, 822-6 (2013).

Fuchs, H. et al. Mouse phenotyping. *Methods* 53, 120-35 (2011).

Fujii, W. et al. Efficient generation of large-scale genome-modified mice using gRNA and CAS9 endonuclease. *Nucleic Acids Res*41, e187 (2013).

Gerondakis, S. et al. Nf-kappaB control of T cell development. *Nat Immunol* 15, 15-25 (2014).

Gibson, D.G. et al. Enzymatic assembly of DNA molecules up to several hundred kilobases. *Nat Methods* 6, 343-5 (2009).

Gratz, S.J. et al. Highly specific and efficient CRISPR/Cas9-catalyzed homology-directed repair in *Drosophila*. *Genetics* 196, 961-71 (2014).

Harrison, M.M. et al. A CRISPR view of development. *Genes Dev* 28, 1859-1872 (2014).

Hartwich, H. et al. A Pink Mouse Reports the Switch from Red to Green Fluorescence upon CRE-mediated Recombination. *BMC Research Notes* 5.1, 296 (2012).

Hippenmeyer, S. et al. Mosaic analysis with double markers reveals cell-type-specific paternal growth dominance. *Cell Rep* 3, 960-7 (2013).

Horii, T. et al. Validation of microinjection methods for generating knockout mice by CRISPR/Cas-mediated genome engineering. *Sci Rep* 4, 4513 (2014).

Ingenious-Targeting-Laboratory. Flexible Accelerated STOP Tetracycline Operator-knockin (FAST): a versatile and efficient new gene modulating system. www.genetargeting.com/products-and-services/types-of-mouse-models/f-a-s-t/.

Inui, M. et al. Rapid generation of mouse models with defined point mutations by the CRISPR/Cas9 system. *Sci Rep* 4, 5396 (2014).

Jinek, M. et al. A programmable dual-RNA-guided DNA endonuclease in adaptive bacterial immunity. *Science* 337, 816-21 (2012).

Kabadi, A.M. et al. Multiplex CRISPR/Cas9-based genome engineering from a single lentiviral vector. *Nucleic Acids Res Advance Access* 1-11 (2014).

Kado, S. et al. Intestinal microflora are necessary for development of spontaneous adenocarcinoma of the large intestine in T-cell receptor beta chain and p53 double-knockout mice. *Cancer Res* 61, 2395-8 (2001).

Kim, J.H. et al. High cleavage efficiency of a 2A peptide derived from porcine teschovirus-1 in human cell lines, zebrafish and mice. *PLOS ONE* 6, e18556 (2011).

Kistner, A. et al. Doxycycline-mediated quantitative and tissue-specific control of gene expression in transgenic mice. *Proc Natl Acad Sci USA* 93, 10933-8 (1996).

Kleinstiver, B.P. et al. High-fidelity CRISPR-Cas9 nucleases with no detectable genome-wide off-target effects. *Nature* 529, 490-5 (2016).

Kratochwil, C.F. et al. The Cre/Lox system to assess the development of the mouse brain. *Methods Mol Biol* 1082, 295-313 (2014).

Linder, C.C. Genetic variables that influence phenotype. *ILAR J* 47, 132-40 (2006).

Liu, C. et al. Mosaic analysis with double markers reveals tumor cell of origin in glioma. *Cell* 146, 209-21 (2011).

Livet, J. et al. Transgenic strategies for combinatorial expression of fluorescent proteins in the nervous system. *Nature* 450, 56-62 (2007).

Loew, R. et al. Improved Tet-responsive promoters with minimized background expression. *BMC Biotechnol* 10, 81 (2010).

Loulier, K. et al. Multiplex cell and lineage tracking with combinatorial labels. *Neuron* 81, 505-20 (2014).

Ma, S. et al. CRISPR/Cas9 mediated multiplex genome editing and heritable mutagenesis of BmKu70 in Bombyx mori. *Sci Rep* 4, 4489 (2014).

Manolio, T.A. et al. Genes, environment, health, and disease: facing up to complexity. *Hum Hered* 63, 63-6 (2007).

Mashiko, D. et al. Generation of mutant mice by pronuclear injection of circular plasmid expressing Cas9 and single guided RNA. *Sci Rep* 3, 3355 (2013).

McLaughlin, M.E. et al. The Nf2 tumor suppressor regulates cell-cell adhesion during tissue fusion. *Proc Natl Acad Sci USA* 104, 3261-6 (2007).

Metzger, D. et al. Conditional site-specific recombination in mammalian cells using a ligand-dependent chimeric Cre recombinase. *Proc Natl Acad Sci USA* 92, 6991-5 (1995).

Niu, Y. et al. Generation of gene-modified cynomolgus monkey via Cas9/RNA-mediated gene targeting in one-cell embryos. *Cell* 156, 836-43 (2014).

Pearson, H. Surviving a knockout blow. *Nature* 415, 8-9 (2002).

Podjasek, J.C. et al. Autoimmune cytopenias in common variable immunodeficiency. *Front Immunol* 3, 189 (2012).

Ramsdell, F. et al. FOXP3 and scurfy: how it all began. *Nat Rev Immunol* 14, 343-9 (2014).

Reiser, M.A. et al. Lipopolysaccharide Responsive Beige-Like Anchor Subcellular Localization Involving in Vesicle Trafficking Responsive to Lipopolysaccharide. *Austin Journal of Clinical Immunology* 1, 8 (2014).

Ridgway, W.M. et al. New tools for defining the 'genetic background' of inbred mouse strains. *Nat Immunol* 8, 669-73 (2007).

Rogner, U.C. et al. Congenic mice: cutting tools for complex immune disorders. *Nat Rev Immunol* 3, 243-52 (2003).

Sakuma, T. et al. Multiplex genome engineering in human cells using all-in-one CRISPR/Cas9 vector system. *Sci Rep* 4, 5400 (2014).

Sakurai, T. et al. A non-inheritable maternal Cas9-based multiple-gene editing system in mice. *Sci Rep* 6, 20011 (2016).

Schreiber, S.L. et al. Genetic screen for modifiers of the rough eye phenotype resulting from overexpression of the Notch antagonist hairless in *Drosophila*. *Genesis* 33, 141-52. (2002).

Shamloula, H.K. et al. R. rugose (rg), a *Drosophila* a kinase anchor protein, is required for retinal pattern formation and interacts genetically with multiple signaling pathways. *Genetics* 161, 693-710 (2002).

Shcherbakova, D.M. et al. Near-infrared fluorescent proteins for multicolor in vivo imaging. *Nat Methods* 10, 751-4 (2013).

Sundberg, J.P. et al. The Cinderella effect: searching for the best fit between mouse models and human diseases. *J Invest Dermatol* 133, 2509-13 (2013).

(56) References Cited

OTHER PUBLICATIONS

Tanaka, K.F. et al. Flexible Accelerated STOP Tetracycline Operator-knockin (FAST): a versatile and efficient new gene modulating system. *Biol Psychiatry* 67, 770-3 (2010).
Taylor-Cousar, J.L. et al. Histo-blood group gene polymorphisms as potential genetic modifiers of infection and cystic fibrosis lung disease severity. *Plos One* 4, e4270 (2009).
Teles Alves, I. et al. Next-generation sequencing reveals novel rare fusion events with functional implication in prostate cancer. *Oncogene* 34, 568-77 (2015).
Treuting, P.M. et al. Of mice and microflora: considerations for genetically engineered mice. *Vet Pathol* 49, 44-63 (2012).
Tu, Z. et al. Embryonic and hematopoietic stem cells express a novel SH2-containing inositol 5'-phosphatase isoform that partners with the Grb2 adapter protein. *Blood* 98, 2028-38 (2001).
Van De Ven, A.A. et al. The autoimmune conundrum in common variable immunodeficiency disorders. *Curr Opin Allergy Clin Immunol* 15, 514-24 (2015).
Wan, Y.Y. et al. Identifying Foxp3-expressing suppressor T cells with a bicistronic reporter. *Proc Natl Acad Sci USA* 102, 5126-31 (2005).
Wang, B. et al. Highly efficient CRISPR/HDR-mediated knockin in mouse embryonic stem cells and zygotes. *BioTechniques* 59, 201-208 (2015).
Wang, H. et al. One-step generation of mice carrying mutations in multiple genes by CRISPR/Cas-mediated genome engineering. *Cell* 153, 910-8 (2013).
Wang, J-W. et al. CRISPR/Cas9 nuclease cleavage combined with Gibson assembly for seamless cloning. *BioTechniques* 58, 161-70 (2015).
Wang, J-W. et al. Deregulated expression of LRBA facilitates cancer cell growth. *Oncogene* 23, 4089-97 (2004).
Wang, J-W. et al. Identification of a novel lipopolysaccharide-inducible gene with key features of both a kinase anchor proteins and chs1/beige proteins. *J Immunol* 166, 4586-95 (2001).
Wang, J-W. et al. Influence of SHIP on the NK repertoire and allogeneic bone marrow transplantation. *Science* 295, 2094-7 (2002).
Wang, J-W. et al. Lipopolysaccharide-responsive beige-like anchor (LRBA), a novel regulator of human immune disorders. *Austin Journal of Clinical Immunology* 1, 9 (2014).
Wang, J-W. et al. LRBA Causes Immunodeficiency and Autoimmunity by Deregulating NFkB-Mediated Multiple Immune Effectors Critical for B Cell Activation. *Journal of Allergy and Clinical Immunology* 133, AB251-AB251 (2014).
Wang, J-W. et al. Nucleotide sequence of a 1446 base pair SalI fragment and structure of a novel early gene of Leucania separata nuclear polyhedrosis virus. *Arch Virol* 140, 2283-91 (1995).
Wech, I. et al. Mutations in rugose promote cell type-specific apoptosis in the Drosophila eye. *Cell Death Differ* 12, 145-52 (2005).
Wright, F.A. et al. Genome-wide association and linkage identify modifier loci of lung disease severity in cystic fibrosis at 11p13 and 20q13.2. *Nat Genet* 43, 539-46 (2011).
Yang, H. et al. Generating genetically modified mice using CRISPR/Cas-mediated genome engineering. *Nat Protoc* 9, 1956-68 (2014).
Yang, H. et al. One-step generation of mice carrying reporter and conditional alleles by CRISPR/Cas-mediated genome engineering. *Cell* 154, 1370-9 (2013).
Yasue, A. et al. Highly efficient targeted mutagenesis in one-cell mouse embryos mediated by the TALEN and CRISPR/Cas systems. *Sci Rep* 4, 5705 (2014).
Yatim, A. et al. NOTCH1 nuclear interactome reveals key regulators of its transcriptional activity and oncogenic function. *Mol Cell* 48, 445-58 (2012).
Zhou, J. et al. Dual sgRNAs facilitate CRISPR/Cas9-mediated mouse genome targeting. *FEBS J* 281, 1717-25 (2014).
Zhou, X. et al. Optimization of the Tet-On system for regulated gene expression through viral evolution. *Gene Ther* 13, 1382-90 (2006).
Zong, H. et al. Mosaic Analysis with Double Markers in Mice. *Cell* 121, 479-92 (2005).
Zuk, O. et al. The mystery of missing heritability: Genetic interactions create phantom heritability. *Proc Natl Acad Sci USA* 109, 1193-8 (2012).

\* cited by examiner

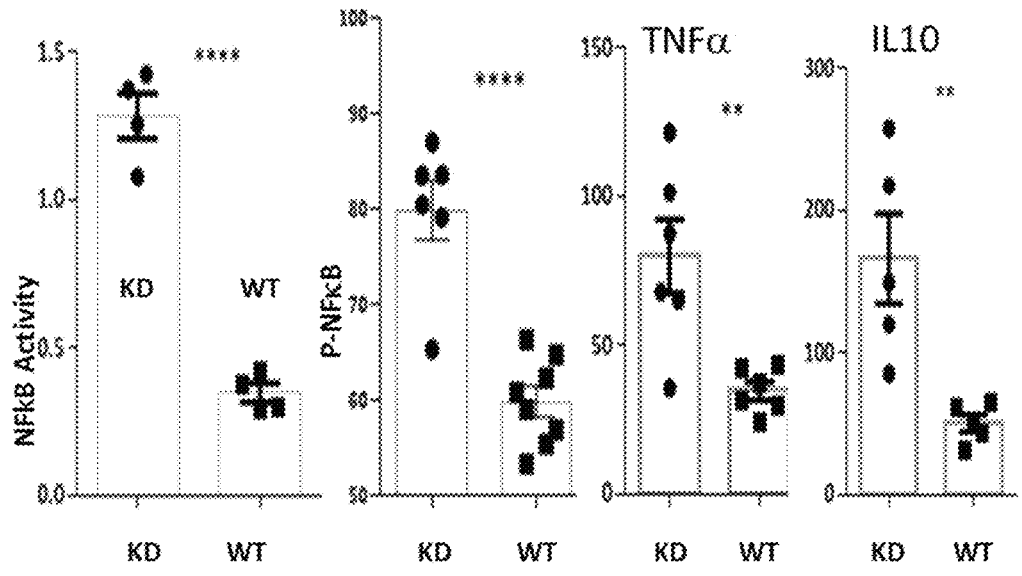
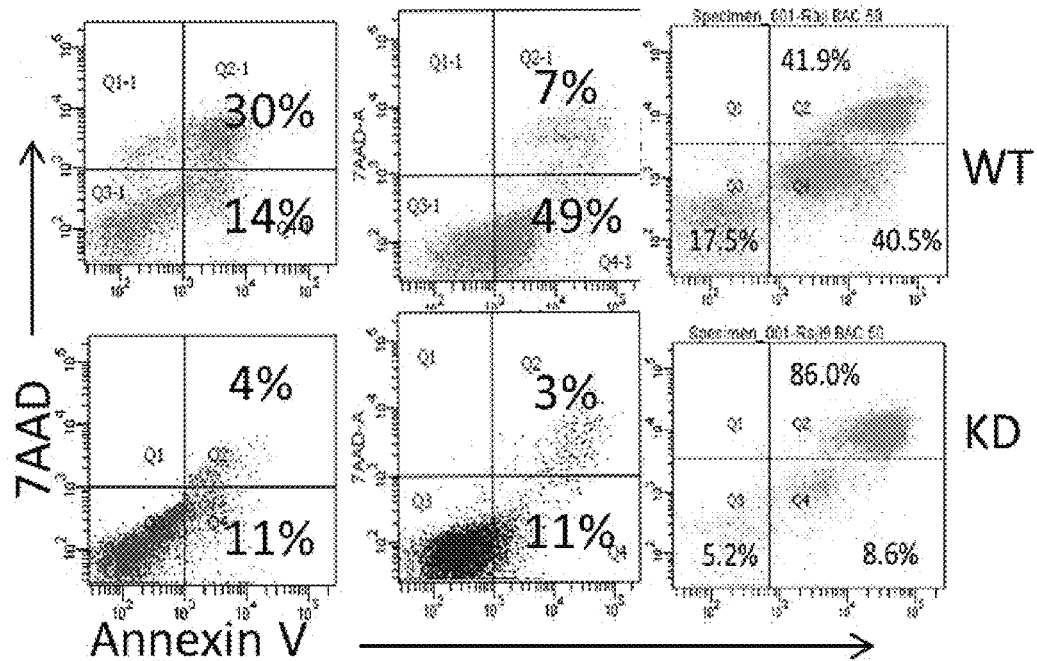
FIG. 2D

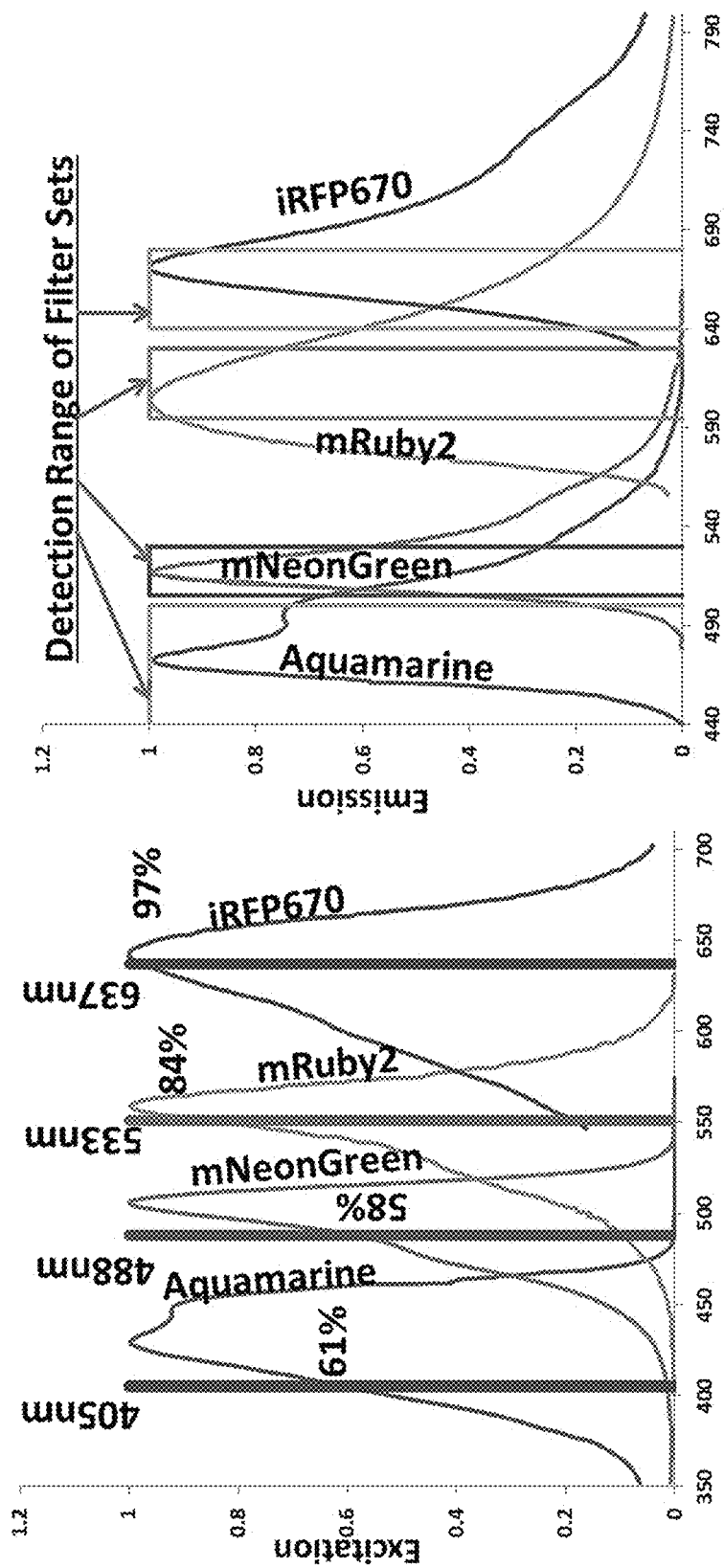

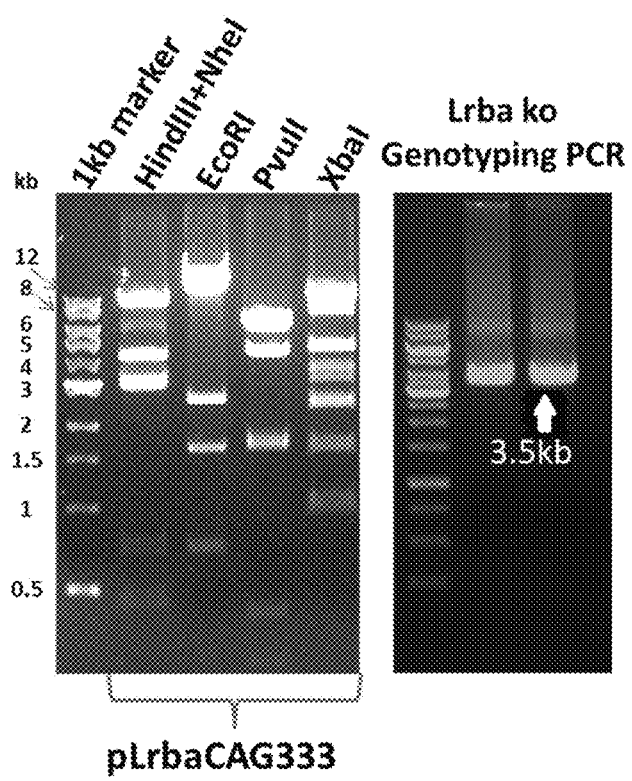
FIG. 4A  FIG. 4B
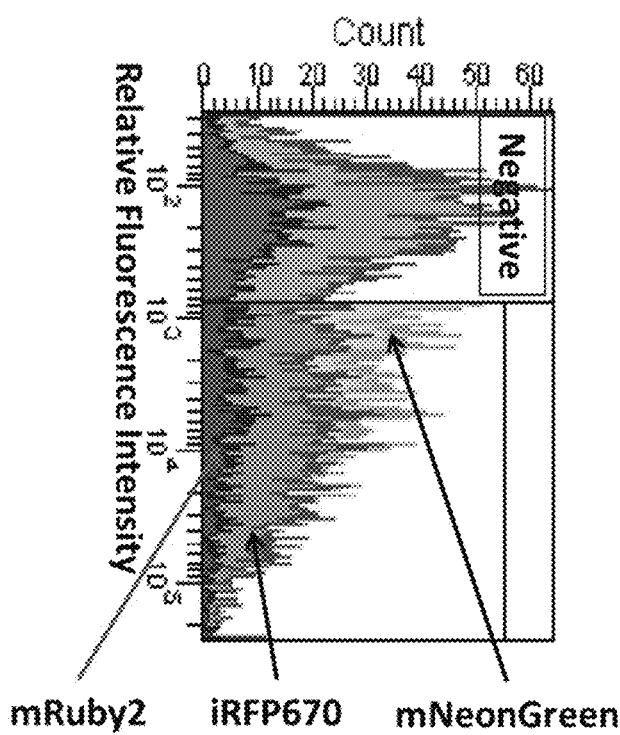 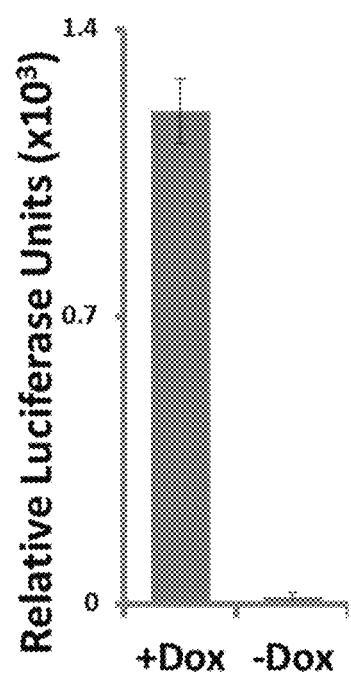
FIG. 4C  FIG. 4D

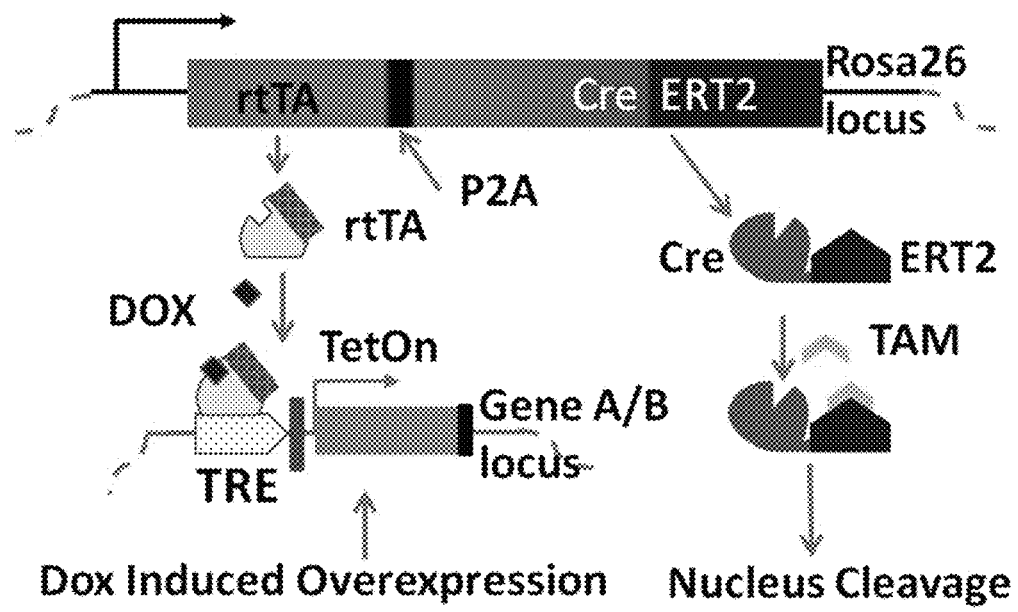
FIG. 5A
| Days | 0 | 7-10 | 10 | 17 | 24-31 | 31 |
|---|---|---|---|---|---|---|
| Treatment | B I | DOX | B II | B III | TAM | B IV |
| Lrba | - | +++ | | - | | ++, +-, -- |
| Nfkb1 | - | +++ | | - | | ++, +-, -- |
FIG. 5B
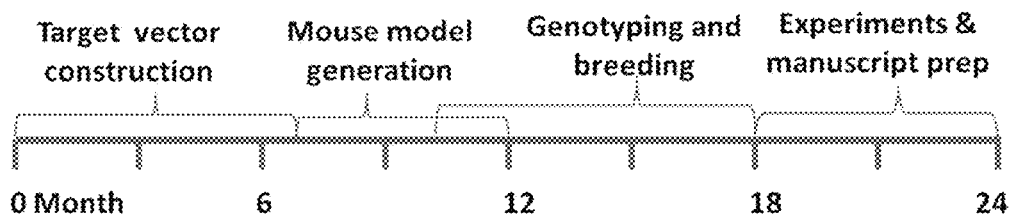
FIG. 5C

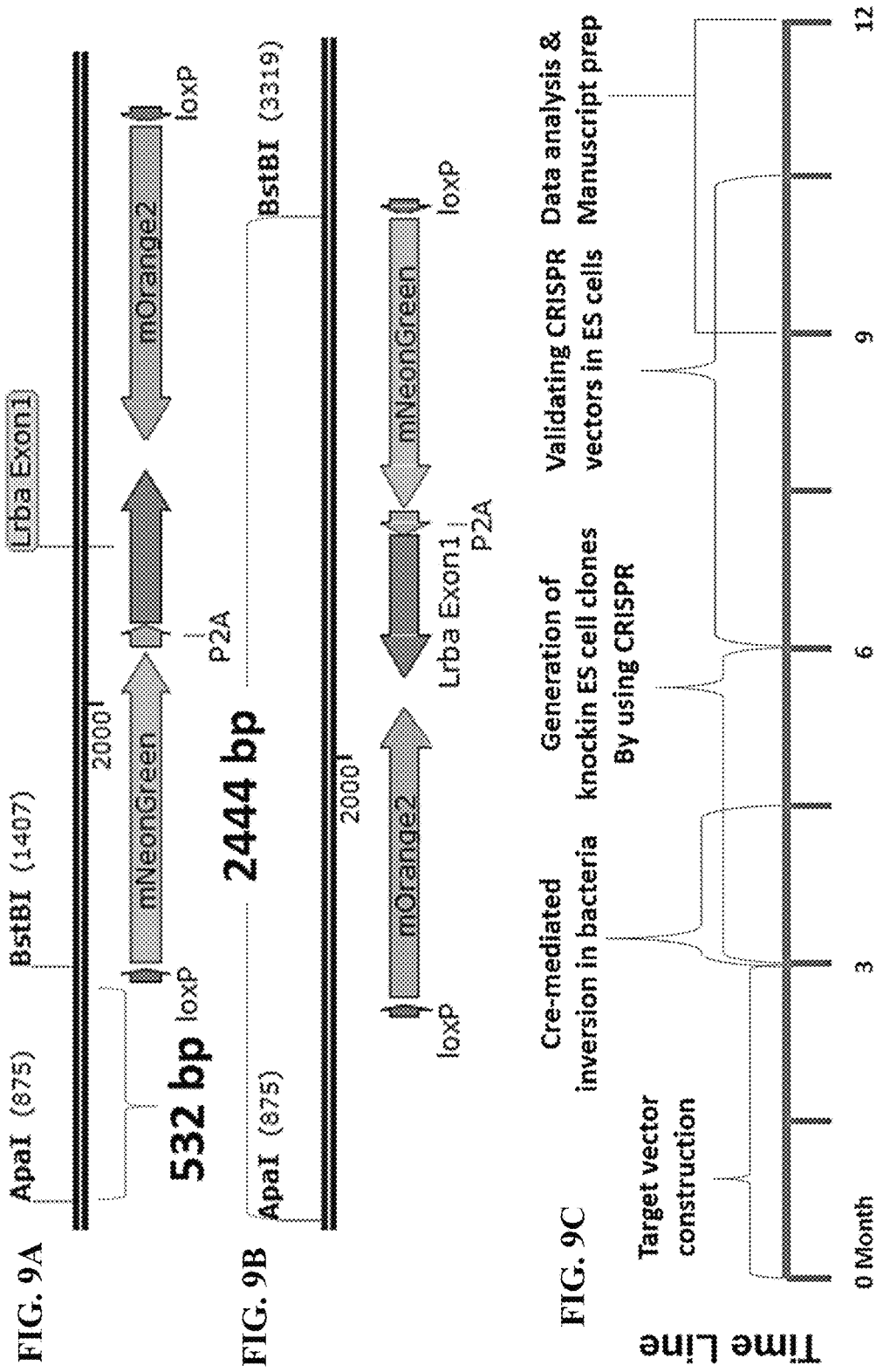

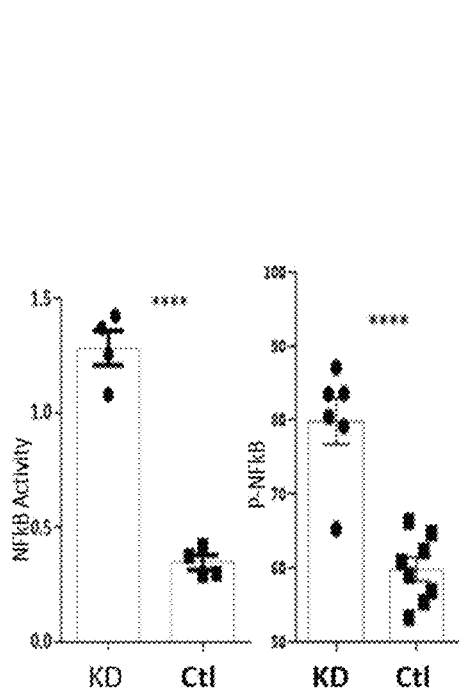
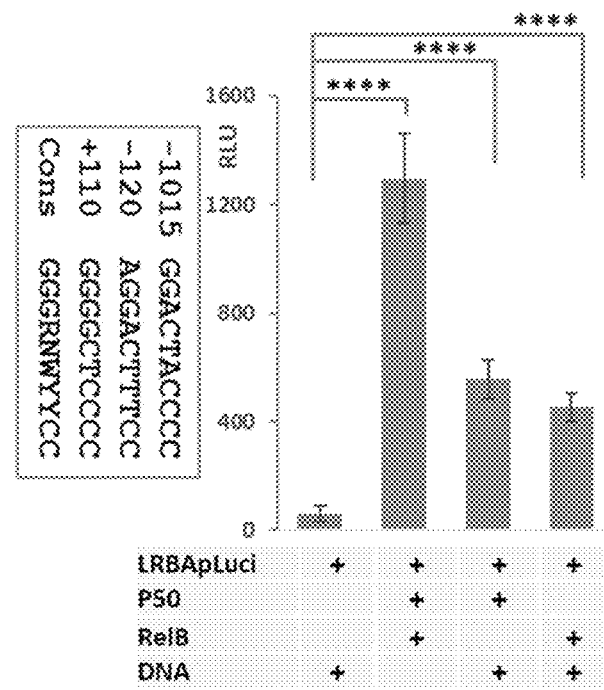
FIG. 11A  FIG. 11C
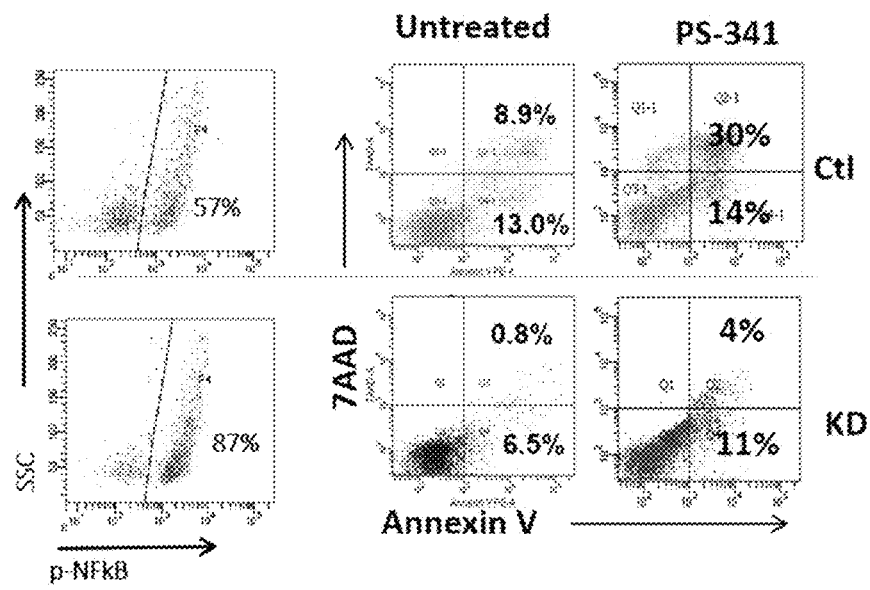
FIG. 11B

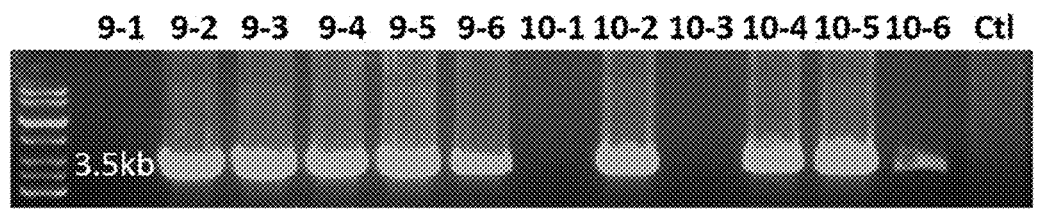
FIG. 12C
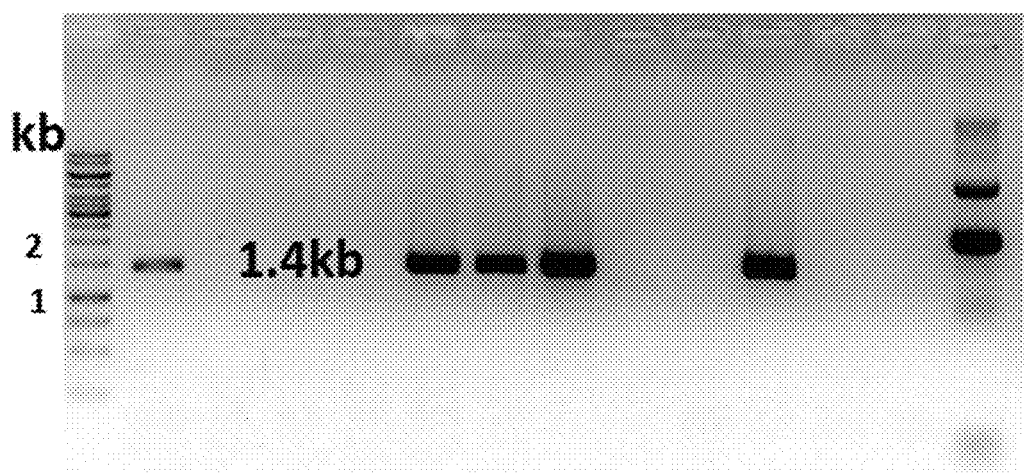
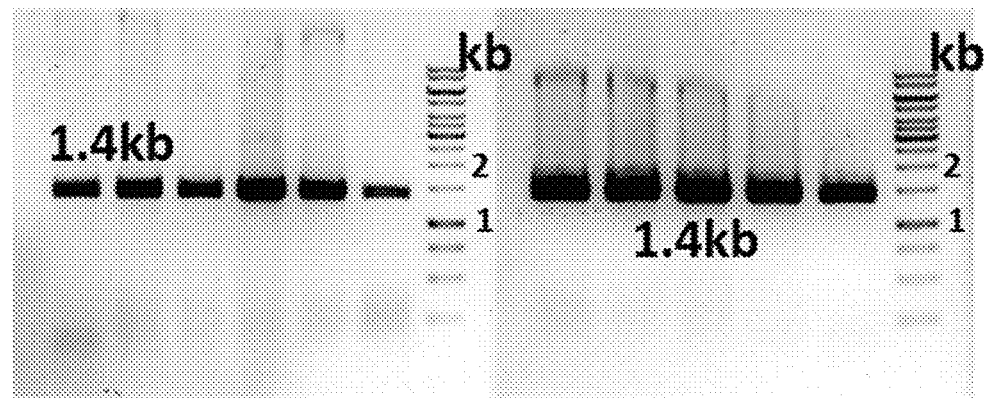
FIG. 12F

Comparison of phenotyping sensitivity

| | | Phenotype Average | Variation | Sensitivity | *Mouse # | *Cell # |
|---|---|---|---|---|---|---|
| T | WT | 18 | 8 | 2 | 2250 | NA |
| | KO | 16 | 8 | | | |
| G | WT | 18 | 0.05 | 0.002 | 1 | 87750 |
| | KO | 17.998 | 0.05 | | | |

T=traditional methods; G= Genebow

FIG. 13C

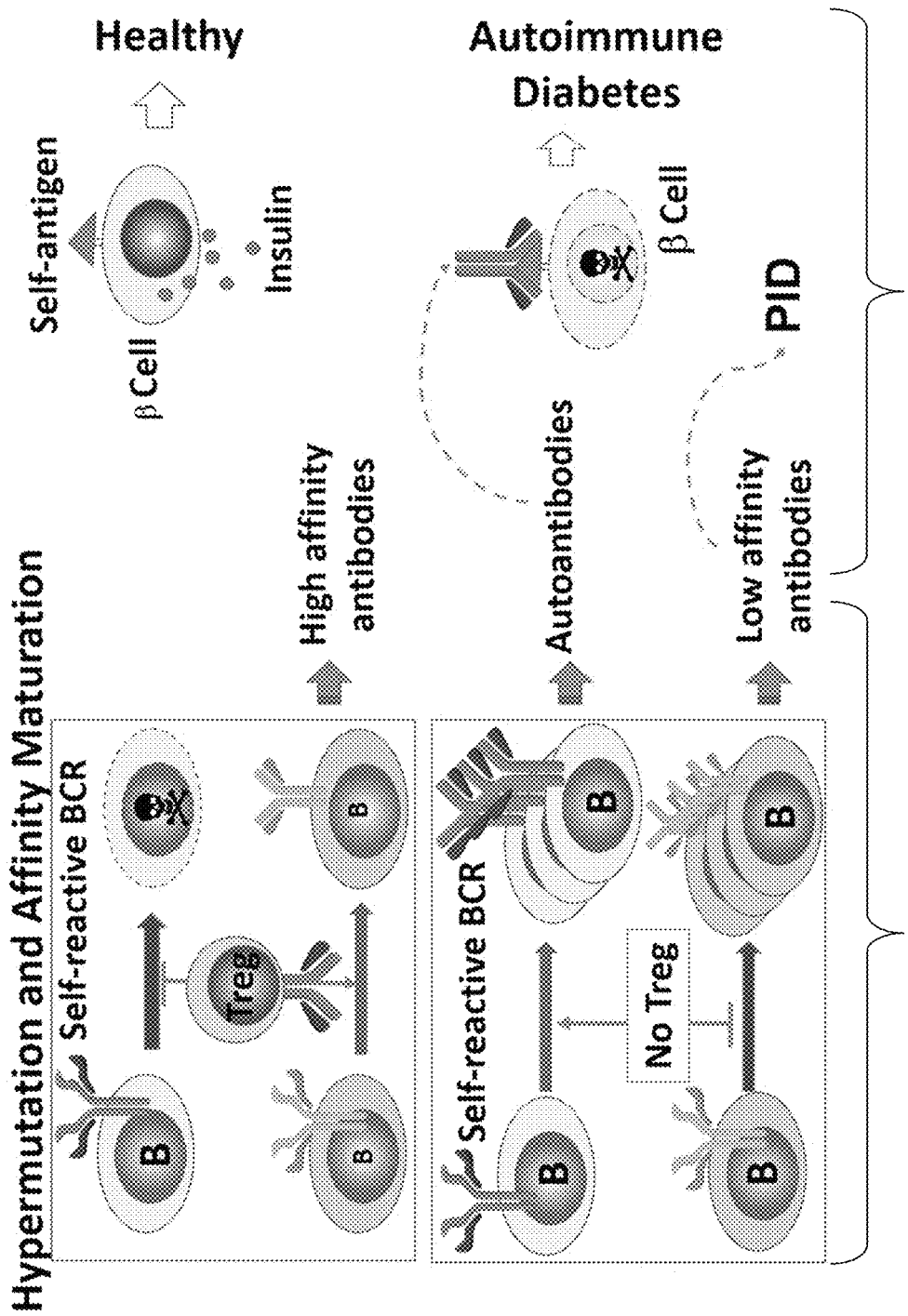

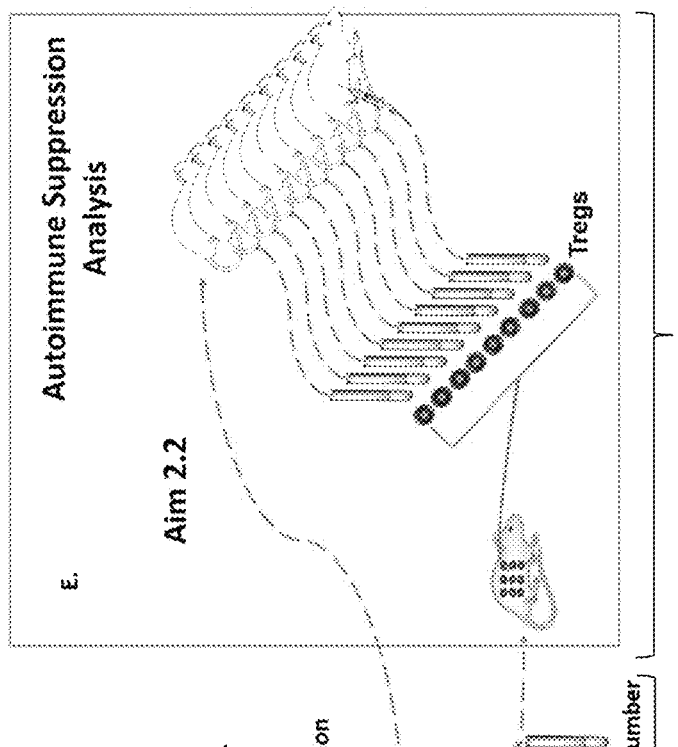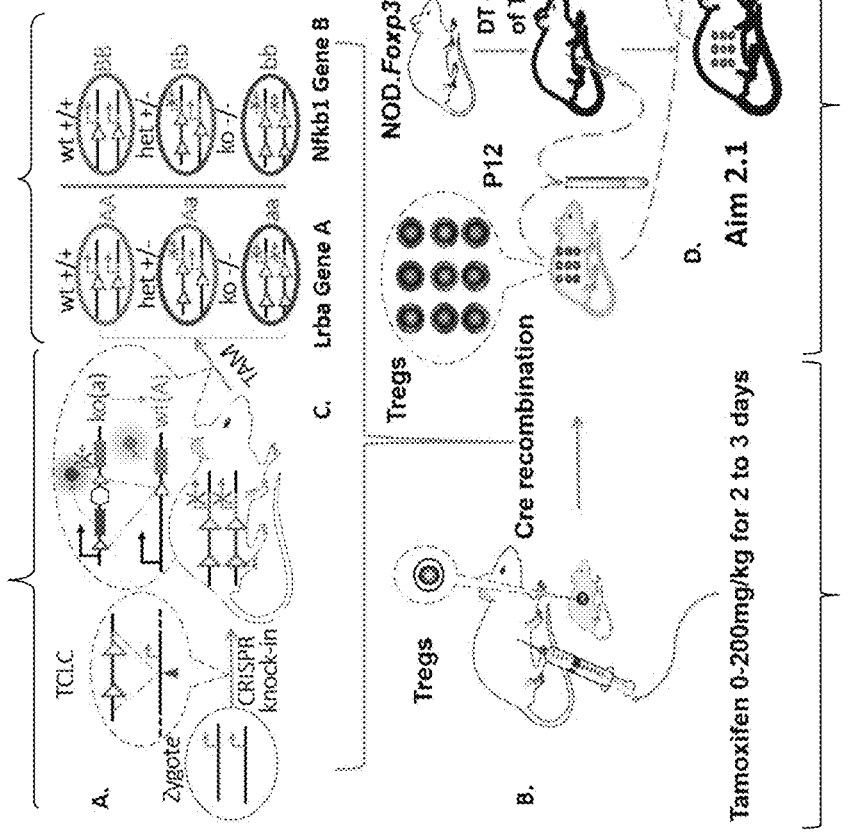
FIG. 16A  FIG. 16C
FIG. 16B  FIG. 16D  FIG. 16E

ANIMAL MODEL AND METHOD FOR STUDYING GENE-GENE INTERACTIONS

CROSS-REFERENCE TO RELATED APPLICATION

The present application claims the benefit of U.S. Provisional Application Ser. No. 62/149,330, filed Apr. 17, 2015, which is hereby incorporated by reference herein in its entirety, including any figures, tables, nucleic acid sequences, amino acid sequences, or drawings.

The Sequence Listing for this application is labeled "2HJ1326.txt" which was created on Apr. 18, 2016 and is 80 KB. The entire contents of the sequence listing is incorporated herein by reference in its entirety.

BACKGROUND OF THE INVENTION

It is believed that many human common diseases result from the complex interplay of genetic and environmental factors, and individual gene contributions are usually small and can be masked by genetic and environmental variations, posing a great challenge in studying genetic interactions in human diseases. Although animal models are indispensable and powerful tools for studying these interactions, current animal models are not suitable to study genetic interactions. Techniques must be developed to rapidly, specifically and sensitively study the interplay of genetic factors in any laboratory animal models over a wide genetic background, essential to understand and treat most human diseases.

The genome-wide association studies (GWAS) show that many common diseases result from the complex interplay of many genes and environmental factors, and that individual gene contributions are small and can be masked by genetic and environmental variations [1]. The history of mouse genetics also makes it clear that the genetic background can cause considerable phenotypic variation in the mice with the same targeted gene. These variables pose a great challenge in studying human disease gene-gene interactions. GWAS have failed to establish common variant risk for the majority of common diseases [15,20]. Animal models are indispensable and powerful tools that have tremendously increased knowledge of gene function. However, animal techniques that can sensitively study gene-gene interactions over a wide genetic background required to decode complex human diseases have yet to be developed.

Current animal models are dependent on establishing a congenic strain and the presumption that animals within the strain are identical [6,7]. Unfortunately, these animals are still subject to genetic, epigenetic and environmental variations which can result in high background noise, low sensitivity, or even false data. Moreover, the lab mice have limited genetic diversity to recapitulate gene-gene interactions in human diseases.

Furthermore, most gene studies have focused on one gene and one strain. To recapitulate human disease gene-gene interactions, the targeted gene should be studied in a variety of inbred strains and wild mice to find interactors of the gene. However, the outbreeding will lose homogeneity, making it virtually impossible to study the gene, and a "congenic" strain from backcrossing has variations as stated above.

BRIEF SUMMARY OF THE INVENTION

To resolve problems associated with currently available animal models, this invention provides a novel animal model in which the nine genotypes of two genes are specifically labeled with four distinct detectable labels (also referred to as reporter molecules) such as fluorescent proteins in a single animal, using the clustered regularly interspaced short palindromic repeats (CRISPR) technique.

This model can be crossed with other strains or wild animals (e.g., wild mice). As each genotype will have the other eight genotypes as controls, congenic strain establishment is not required, allowing a rapid (about two months) genetic background switch and the F1 animals can be directly used in study. Therefore, this technique, named "Genebow", can be used to label cells with many signals (e.g., colors) which may be measured or otherwise detected to study interactions of adjacent cells as in Brainbow. More importantly, Genebow can be used to study gene-gene interaction with high sensitivity, specificity due to the elimination of aforementioned variations, and over a wide genetic background required to model human disease gene-gene interactions.

As proof of principle, the lipopolysaccharide-responsive, beach and anchor containing (Lrba) and Nfkb1 genes will be used to develop the Genebow model to study how the genetic interactions of the two genes affect the apoptosis of leukocytes. The mutations of LRBA cause immunodeficiency and autoimmunity with highly variable symptoms and LRBA interacts with many crucial regulators including NFkB in vitro. The invention will permit study of how LRBA interacts with these regulators in vivo to better understand the immune system.

Mutations of LRBA paradoxically cause both immunodeficiency and autoimmunity. LRBA deficient patients have more $CD20^+$ B cells responsive to anti-CD20 therapy [46-49], indicating increased B cell survival. LRBA knockdown (KD) protects Raji B cells from death induced by various stress stimuli (FIG. 2D). However, LRBA has been suggested to be an oncogene, and LRBA KO decreases cell survival (FIG. 2E) and LRBA KD causes more Raji cells death upon infections (FIG. 2D, right panels). These contradictory results and the highly variable symptoms present in LRBA-deficient patients indicate complex interactions in multiple genes and environmental inputs. Indeed, LRBA interacts with multiple genes such as EGFR, NOTCH and RAS/MAPK [3-5], and LRBA KD increases phospho-NFkB levels and NFkB activity (FIGS. 2A and 2B). Correspondingly, the levels of TNF and IL10, NFkB target gene products, are increased (FIGS. 2C-1 and 2C-2). On another hand, NFkB potentially regulates LRBA [4,50]. NFkB is the central regulator of the immune system and plays a pivotal role in cell survival [4,51,52]. Without being limited by theory, the inventors propose that NFKB1 is an important modifier of LRBA and genetically interacts with the latter to affect cell survival, a key to understand the paradoxical association of immunodeficiency and autoimmunity, a unsolved fundmental question.

The CRISPR can generate up to 78% multiplex targeted mutations in mice in about three months [53-59,60]. It causes a DNA double strand break (DSB), which can be repaired by homology-directed-repair (HDR) [61,62]. A DNA fragment flanked by two homologous sequences can be inserted into the DSB cleaved site by homologous recombination, the efficiency of which can be 5000 times higher than traditional homologous recombination [63]. Due to these advantages, the CRISPR/HDR technique will be used to generate the Genebow mouse model (FIG. 1). It requires a single guide RNA (sgRNA) and a target repair template for each gene.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 2A, 2B, 2C-1, 2C-2, 2D, and 2E. LRBA interacts with NFkB and regulates cell survival. FIG. 2A: LRBA was stably knocked down in Raji cells by the short hairpin (sh) RNA technique in Raji B cells. NFkB activity was measured by an NFkB luciferase reporter. FIG. 2B: The phospho-NFkB (pS529) levels were detected by Phosflow Kit. FIGS. 2C-1 and 2C-2: TNFα (FIG. 2C-1) and IL10 (FIG. 2C-2) proteins levels were measured by the human Th1/Th2 cytokine bead-array kit. FIG. 2D: Apoptosis assay. Raji B cells were treated with various stress stimuli including proteasome inhibitors, serum starvation and bacterial infection. Apoptosis was detected by Annexin V-PE and 7-AAD. FIG. 2E: LRBA (−/−) ES cell clones were obtained by culturing LRBA (+/−) ES cells with 1 mg/ml G418 for ~two weeks. Equal number of ES cells was plated into each well of a 96-well plate. The average cell numbers were counted from three wells at each time point.

FIGS. 3A-3C. FIG. 3A: High throughput construction of target templates (SEQ ID NOs:8-11). The left and right arms (each 1 kb) that end or start with the sequences shown will be PCR amplified from the C57Bl/6J genomic DNA. The target template will be assembled by the enzymatic ligation assisted by nucleases (ELAN) via simultaneous ligation and digestion, in the presence of gel purified TCFP, both arms, BsmBI, with T4 DNA ligase and ATP added to the mixture following the protocol [2]. BsmBI will produce ends of the left and right arms compatible to the MluI and SalI stick ends at the ends of the TCFP cassette. This one-tube preparative-scale assembly will produce enough DNA template for CRISPR targeting, which requires a 200 ng/ml DNA template. Thus, cloning is not necessary. FIGS. 3B and 3C: Excitation and emission spectra of the four FPs. Four excitation lasers (thick lines) and detection filter sets (open bars) are shown. The percentages are excitation efficiencies for each dye with the designed laser. These is no detection overlap between these FPs. The LIVE/DEAD Yellow and R-PE-Cy7 dyes, used for dead cell and annexin V labeling, also will not overlap with any FP after compensation. For clarity, their spectra are not shown.

FIGS. 4A-4I. Construction of CRISPR/HDR vectors and CRISPR cleavage test. The target vector is constructed from a 12 kb fragment subcloned from a C57BL/6J BAC clone using BAC subcloning kit (Gene Bridges). The TCFP cassette splits the genomic fragment into 3 kb left and 9 kb right arms. FIG. 4A: The Lrba target vector was digested with restriction enzymes. FIG. 4B: PCR Genotyping test of Lrba KO using the primers from the TCFP cassette and the genomic DNA sequence outside of the short arm. FIG. 4C: Flow cytometry detection of the three FP in H293 cells. FIG. 4D: A secretable luciferase gene was inserted in place of Lrba through HR to functionally test the TCFP. The Luciferase assay was conducted in H293 cells transfected with the target vector with and without Dox. Without induction, the luciferase activity is negligible. FIG. 4E: SpeI digestion of the PCR product using genomic DNA from mouse ES cells transfected with Lrba sgRNA/Cas9 vector. The white arrow indicates the mutated alleles (SpeI destroyed). The sgRNA target site in the PCR product, 713 bp, contains a SpeI site. SpeI digestion produces 527 bp and 186 bp fragments in wt but cannot cut the CRISPR targeted allele. FIG. 4F: Cas9/sgRNA can specifically digest the Lrba BAC subclone plasmid as expected. Portions of sequencing trace showing sequences of Lrba/SD/loxP (FIG. 4G) (SEQ ID NO:12), STOP/loxP (FIG. 4H) (SEQ ID NO:13), and Aqua/P2A/Lrba (FIG. 4I) (SEQ ID NO:14).

FIGS. 5A-5C. FIG. 5A: TetOn and inducible Cre system. The overexpression of gene AB can be induced by Dox while TAM activates Cre to cleave the STOP and restore the expression of gene A/B. FIG. 5B: Protocol for studying Lrba and Nfkb1 genes. A concentration of 20 µg/ml Dox in 2% sucrose will be supplied in the drinking water for the Genebow mice >6 wks of age for three days (red line (rtTA)) to overexpress Lrba and Nfkb1. The withdrawal of Dox will turn off the expression of the two genes. Administration of Tam by i.p. will activate Cre (green line). Peripheral blood will be collected as indicated from the mouse before and after each treatment and subjected to flow cytometry assay. ++wt, +−het, −−ko, +++overexpression. B: bleeding. FIG. 5C: Timeline.

FIG. 7A: Traditionally, cells from each mouse (genotype) have to be analyzed separately, because if mixed, they cannot be distinguished. In contrast, Genebow can distinguish each genotype in a mixture. Consequently, e.g., to quantitate T cells of different genotypes, traditional method usually requires at least 27 mice and 27 tubes. While the Genebow requires only one mice and one tube. More importantly, the phenotyping sensitivity can be greatly increased, e.g., 1000 times (2/0.002. Bottom, an example). Calculations [112] were based on hypothetic averages and variations.*Total number required to obtain statistically significant data (p<0.05, power=80%). Nine genotypes are color-labeled. Wild type: uppercase, knockout: lowercase. FIG. 7B: LRBA KD deregulates MAPKs. LRBA was stably knocked down (KD) in Raji cells by the short hairpin RNA technique. Cell lysates from WT or LRBA KD stable Raji cells were analyzed by Western blot. Protein levels were quantified with Quantity One software. Phosphorylated (P-) protein levels were normalized to β-Actin. FIG. 7C: NFkB activity was measured by an NFkB luciferase reporter. FIG. 7D: NFkB binding sites in human LRBA promoter and LRBA promoter assay (SEQ ID NOs: 15-18). H1299 cells were transfected with the same amount of plasmid DNA expressing luciferase under LRBA promoter (LRBApLuci), NFkB p50 (P50) and RelB. DNA is an irrelevant plasmid DNA used to ensure equivalent amount of DNA in each transfection. RLU, relative luciferase unit. ****, $p<5.8E-5$. FIG. 7E: CRISPR knock-in in H1299 cells with short homologous arms (1 kb) of LRBA. Primers from the genomic sequence outside of homologous arm and exogenous sequence in the knockin vector were used for the PCR screening. The predicted size of the PCR product for positive clones is 1.4 kb.

FIG. 8A: (SEQ ID NOs:19-30). Cre recombinase-mediated inversion. loxP (locus of crossover in P1) consists of two 13 bp inverted repeats flanking an 8 bp core sequence that determines its polarity (denoted by dashed arrows). Cre recombinase cleaves (small vertical arrows) the two inverted loxP sites. The cleavage produces two complementary protruding sequences: 5'-cataca at the ends of the intervening DNA, and 3'-tgtatg at the ends of the flanking DNA. The cleaved intervening DNA is ligated back in an inverted orientation. As the sequences of the two loxP sites and the size of the intervening DNA remain unchanged, the reaction is reversible and the reaction rates of forward and reverse reactions should be equal. In a balanced reaction, the numbers of the two end products, the original (i) and the inverted (ii), are equal. FIG. 8B: Genotype-switching and labeling cassettes (GSLC). The first exon of Lrba is flanked with two inverted fluorescent protein genes. The green FP† and Lrba are coexpressed. Cre-mediated inversion inactivates the co-expression but activates red FP expression. The wt allele is converted to ko allele and the green FP is replaced by red FP. Correspondingly, as each cell has two alleles, ko cells (with two ko alleles) will be labeled as red FP, wt cells as green FPs, and heterozygous (het) cells as red/green FPs, and can be distinguished by flow cytometry. As stated in FIG. 8A, the numbers of wt and ko alleles should be equal. This is important, as Cre recombination will not be a variable confound the interpretations of results that are affected by genotype frequency. After the Cre reaction is balanced, Cre has to be removed. This can be easily done by stopping tamoxifen (TAM) treatment in the TAM-induced Cre system. Otherwise the cleavage/inversion will continue forever, and the wt/ko alleles in the cells will be switched back and forth. †mNeongreen (NeonG), mOrange2, mKate2, and TagBFP2 have relative brightnesses over 35.23 EGFP and mRFP1 have a relative brightness of 36 and 13 have been successfully used to label cells [122]. Therefore, the inventors will use these four fluorescent proteins to label the two genes. The flow cytometer can detect 16 colors. Since four channels will be used by the four FPs, there are 12 channels available to conduct almost any multiplex flow cytometry that is routinely used in research. FIG. 8C: Cloning strategy of donor vectors. The Lrba homologous arms (~2 kb) will be PCR amplified and cloned into the pJet vector using the CloneJET PCR Cloning Kit. The GSLC1 (2 kb) with short homologous sequences of Lrba at both ends will be synthesized by Genscript, and cloned into the pJetHR-Lrba vectors by using the CRISPR cloning technique [118].

FIGS. 9A-9C. Characterization of Cre-mediated inversion by restriction enzyme digestion, and Time Line (FIG. 9C). The ApaI/BstI digestion will produce a 532 bp fragment when the intervening DNA is in original orientation (FIG. 9A), or a 2444 bp fragment when the intervening DNA is in inverted orientation (FIG. 9B). This assay will be used to analyze Cre-mediated inversion in bacteria detected by electrophoresis and in ES cells detected by Southern blot.

FIGS. 11A-11E. LRBA interacts with important genes in regulating apoptosis and proliferation. LRBA was stably knocked down (KD) in Raji cells by the short hairpin RNA technique. FIG. 11A: NFkB activity was measured by an NFkB luciferase reporter. The Phosphorylated (P-) NFkB (pS529) levels were detected by Phosflow Kit. FIG. 11B: Apoptosis assay. Raji B cells were treated with PS-341, an NFkB inhibitor. FIG. 11C: NFkB binding sites in human LRBA promoter and LRBA promoter assay (SEQ ID NOs: 15-18). H1299 cells were transfected with the same amount of plasmid DNA expressing luciferase under LRBA promoter (LRBApLuci), NFkB p52 (P52) and RelB. DNA is an irrelevant plasmid DNA used to ensure equivalent amount of DNA in each transfection. RLU, relative luciferase unit. ****, $p<5.8E-5$. FIG. 11D: LRBA$^{-/-}$ ES cell clones were obtained by culturing LRBA$^{+/-}$ ES cells with 1 mg/ml G418 for ~two weeks. Equal numbers of ES cells were plated into each well of a 96-well plate. The average cell numbers were counted from three wells at each time point. FIG. 11E: LRBA KD deregulates MAPKs. Cell lysates from WT or LRBA KD stable Raji cells were analyzed by Western blot. Protein levels were quantified with Quantity One software. Phosphorylated (P-) protein levels were normalized to β-Actin.

FIGS. 12A-12F. CRISPR vector construction and CRISPR targeting of mouse embryonic stem (ES) cells and zygotes. The target vector was constructed from a 12.5 kb genomic fragment and has 3.5 kb left and 9 kb right arms flanking the transcription control and labeling cassette (TCLC). FIG. 12A. Portions of sequencing trace show the sequences at the 5' junction (FIG. 12A) (SEQ ID NO:31) and 3' junction (FIG. 12B) (SEQ ID NO.14) of the TCLC cassette insertion. FIG. 12C: PCR screening for Lrba knockin-positive ES clones. Primers from the genomic sequence outside of homologous arm and exogenous sequence in the knockin vector were used for the PCR screening. The predicted size of the PCR product is 3.5 kb. FIG. 12D: Southern blot. EcoRV-digested genomic DNAs were hybridized with a 5' external probe with expected fragment sizes of 5 kb (wt) and 13 kb (targeted). 1. Linearized target vector (22 kb). 2-11: G418-positive clones. #4 and #9 incorrectly targeted. #6 Wt, other clones are correctly targeted heterozygotes. The results agree with the PCR results. FIG. 12E: Nested PCR detection of correctly targeted blastocysts derived from zygotes injected with CRISPR reagents. One quarter of DNA from a blastocyst was used for the first PCR (FIG. 12C). FIG. 12F: CRISPR knock-in with short homologous arms (1 kb). Primers were designed as in FIG. 12C. The predicted size of the PCR product is 1.4 kb.

FIGS. 13A-13C. Principle of Genebow. FIG. 13A: The structure of TCLCs is the same as that of Brainbow 3.1 [158], except a porcine teschovirus-1 2A (P2A†) peptide DNA sequence is inserted between the last FR gene and the targeted genes just before the translation codon to co-express the two genes in links. CFP=Aquamarine, which is superior to the popular form ECFP [166]; RFP=iRFP670, a near-infrared FP [167]. lox sites: loxP (P), loxN (N), lox2272 (2), lox 5171 (5). pA, SV40 PolyA sequence is used to stop the transcription of downstream genes. †Due to its small size, high self-cleavability, and ability to produce an equal molar ratio of the two proteins, P2A is widely used to link two proteins to be co-expressed by a single promoter [168]. FIG. 13B: Cre recombinase-mediated recombination solely removes DNA between two identical lox sites. The recombination between the two loxP sites turns on the $FR1_+^\dagger$, producing the ko allele. While the recombination between the two Lox2272 sites turns on CFP, producing the wt allele. $_+^\dagger$ Fluorescent proteins are the most commonly used reporters as best exemplified by the Brainbow [158,162]. Aquamarine and iRFP670 will be used as their spectra are well separated and do not overlap with those of commonly used fluorophores. mRuby2, mKate2, Aqua and iRFP670 with a relative brightness of 46, 35, 23 and 13, respectively [169]. EGFP and mRFP1 with a relative brightness of 36 and 13 have been successfully used to label cells [170]. Therefore, the inventors will use four fluorescent proteins to label the two genes. The flow cytometer can detect 16 FCs. Since four channels will be used by the four FRs, there are 12 channels available to conduct almost any multiplex flow cytometry that is routinely used in research. FIG. 13C: Comparison of phenotyping sensitivity. In this example, phenotyping sensitivity can be greatly increased by 1000 times (2/0.002) in the Genebow model. Calculations [171] were based on hypothetic averages and variations. *Total number required to obtain statistically significant data (p<0.05, power=80%) for the 9 genotypes.

FIGS. 14A-14D. LRBA's role in the development and function of Tregs in autoimmune diabetes mouse models. FIG. 14A: Cloning strategy of donor vectors. The homologous arms (~2 kb) for each gene will be PCR amplified and cloned into the pJet vector. TCLC1 or 2 (~3 kb) with short homologous sequences of Lrba or Nfkb1 at both ends will be synthesized, and cloned into the corresponding vectors that have homologous sequences for targeting Lrba and Nfkb1 by using the inventors' CRISPR cloning techniques [139]. FIG. 14B: Generation of mouse model and mating scheme. Genebow mouse model will be generated by triplex CRISPR targeting. Foxp3.DTR+ mice express human diphtheria toxin receptor from the Foxp3 promoter from BAC transgenesis—without disrupting expression of the endogenous Foxp3 gene. Diphtheria toxin (DT) administration results in ablation of Treg cells. DT administration results in ablation of Treg cells 2 days after injection. Neonates injected with DT daily all die from autoimmune disease within 27 days of birth. Lrba and Nfkb1 are 49 Mb away on chromosome 3, CreERT2/Rosa 26 on chromosome 6, and FoxP3GFP on chromosome X. FIG. 14C: Tregs play a major role in regulating the production of antibody and autoantibody. Tfrs are required to produce high affinity antibodies, and to limit autoantibody production. Depletion of Tfrs leads to autoantibody overproduction and antibodies with low affinity, resulting in autoimmune disease and immunodeficiency, respectively.

FIGS. 16A-16E. Genebow mouse model and genetic interaction study. FIG. 16A: a transcription control and labeling cassette (TCLC) is inserted into the genomic locus of Lrba by using the CRISPR technique. This insertion turns off Lrba as the TCLC contains a STOP cassette but turns on a red FR (RFR) as it places the RFR under the Lrba promoter. For clarity, only one pair of lox sites is shown. FIG. 16B: tamoxifen (TAM) will be administered to neonates via lactating mother intraperitoneally injected with tamoxifen at optimal dosage and time. FIG. 16C: TAM activates Cre recombinase, which removes the RFR-STOP between the two loxP sites (triangle) and turns on Lrba and switches the RFR to blue FR (BFR). Thus, the on and off of Lrba can be labeled separately with two FRs. Cre recombination will result in three genotypes: knockout (ko, red), heterozygote (het, blue/red) and wild type (wt, blue). Similarly, another gene can be labeled with two other FRs (purple/green). The 9 genotypes of two genes thus can be specifically labelled with four FRs. X=no expression. FIG. 16D: Tregs with nine genotypes will be sorted and $3.6 \times 10^5$ of mixed ($4 \times 10^4$/genotype) Tregs will be injected ip into Treg-depleted non-obese diabetic (NOD) neonates. For depletion of Treg cells, Foxp3-DTR+ mice or control littermates will be injected ip with DT every other day for 10 days. FIG. 16E: Tregs with nine genotypes will be sorted and $3.6 \times 10^5$ of Tregs for each genotype from Genebow mice will be injected ip into a Treg-depleted non-obese diabetic (NOD) neonate, and then followed for manifestations of autoimmune disease up to 100 days.

BRIEF DESCRIPTION OF THE SEQUENCES

SEQ ID NO:1: *Mus musculus* LPS-responsive beige-like anchor (Lrba), transcript variant 2, mRNA. Accession number: NM_001077688.

SEQ ID NO:2: *Mus musculus* LPS-responsive beige-like anchor (Lrba), transcript variant 1, mRNA. Accession number: NM_030695.

SEQ ID NO:3: *Mus musculus* LPS-responsive beige-like anchor (Lrba), transcript variant 3, mRNA. Accession number: NM_001077687.

SEQ ID NO:4: *Homo sapiens* LPS-responsive vesicle trafficking, beach and anchor containing (LRBA), transcript variant 1, mRNA. Accession number: NM_001199282.

SEQ ID NO:5: *Homo sapiens* LPS-responsive vesicle trafficking, beach and anchor containing (LRBA), transcript variant 2, mRNA. Accession number: NM_006726.

SEQ ID NO:6: *Mus musculus* nuclear factor of kappa light polypeptide gene enhancer in B cells 1, p105 (Nfkb1), mRNA. Accession number: NM_008689.

SEQ ID NO:7: Human nuclear factor kappa-B DNA binding subunit (NF-kappa-B) mRNA, complete cds. Accession number: M58603.

Figure 3A:
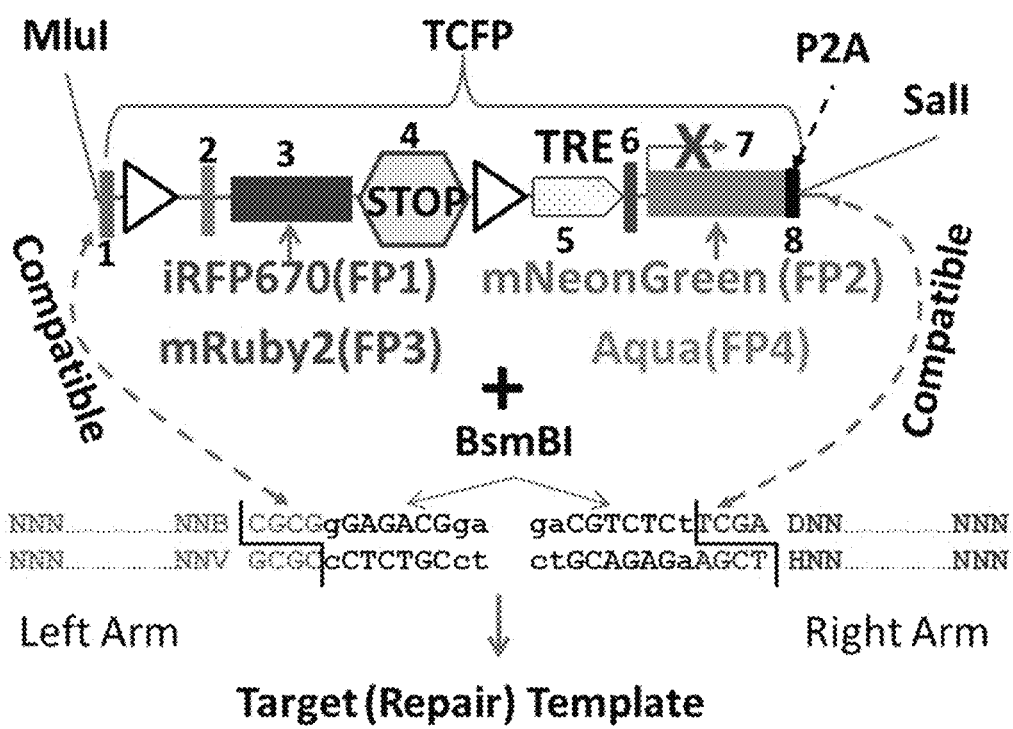

SEQ ID NOs:8-11: target template sequences (FIG. 3A).

SEQ ID NO:12: Lrba/SD/loxP portion of Lrba BAC subclone plasmid (FIG. 4G).

Figure 4E:
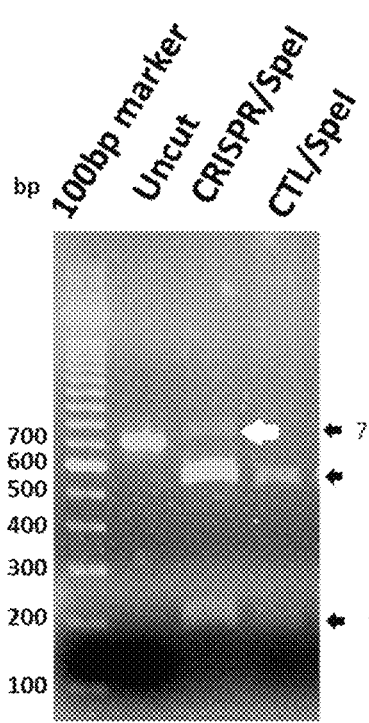
Figure 4F:
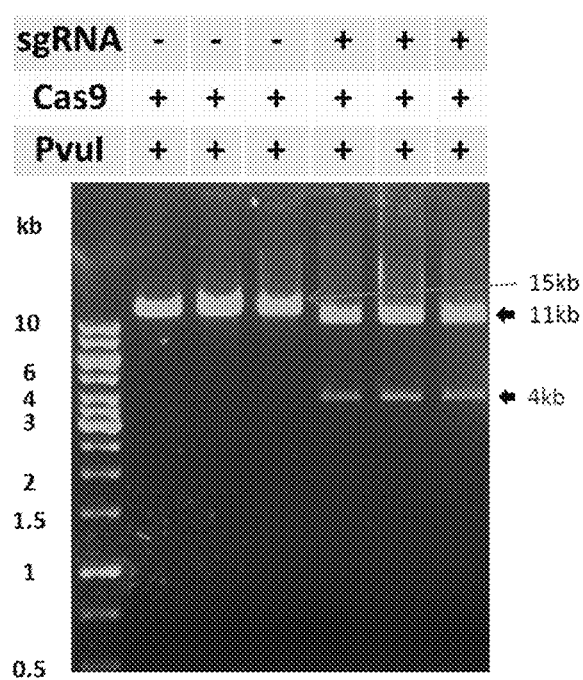
Figures 4G, 4H, 4I:
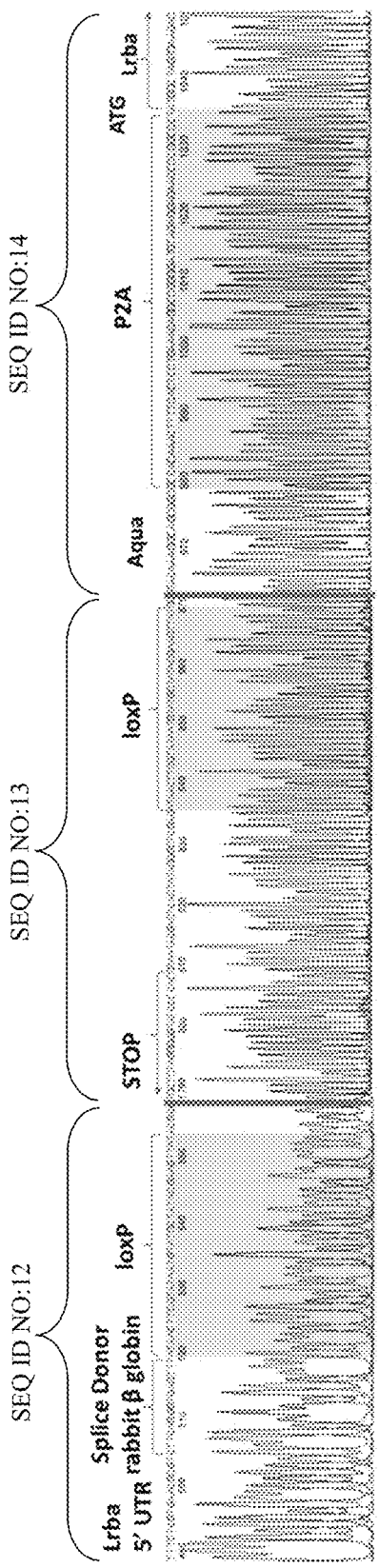

SEQ ID NO:13 STOP/loxP portion of Lrba BAC subclone plasmid (FIG. 4H).

SEQ ID NO:14: Aqua/P2A/Lrba portion of Lrba BAC subclone plasmid (FIG. 4I).

Figure 7A:
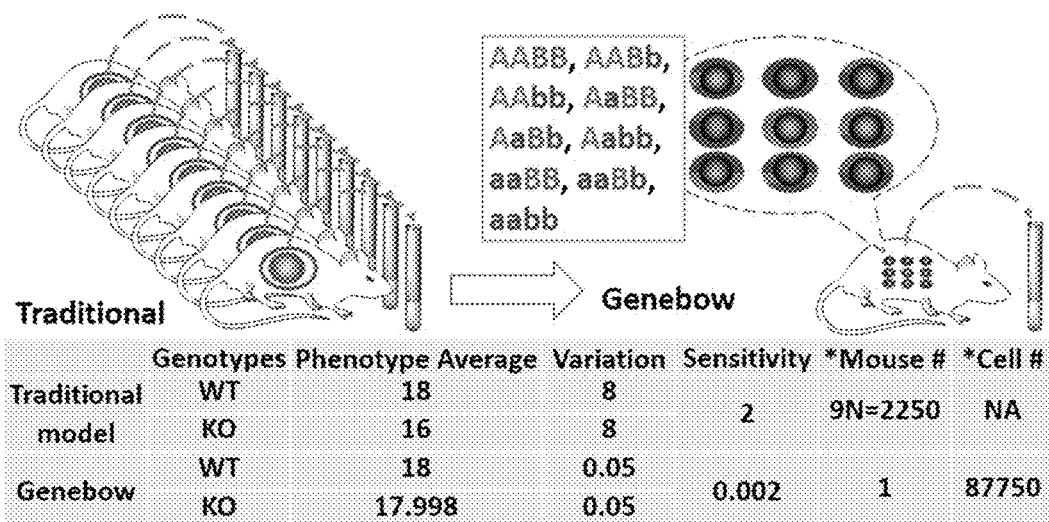
FIGS. 7A-7E. Comparison of Genebow and traditional method, and preliminary data.
Figures 7B, 7C:
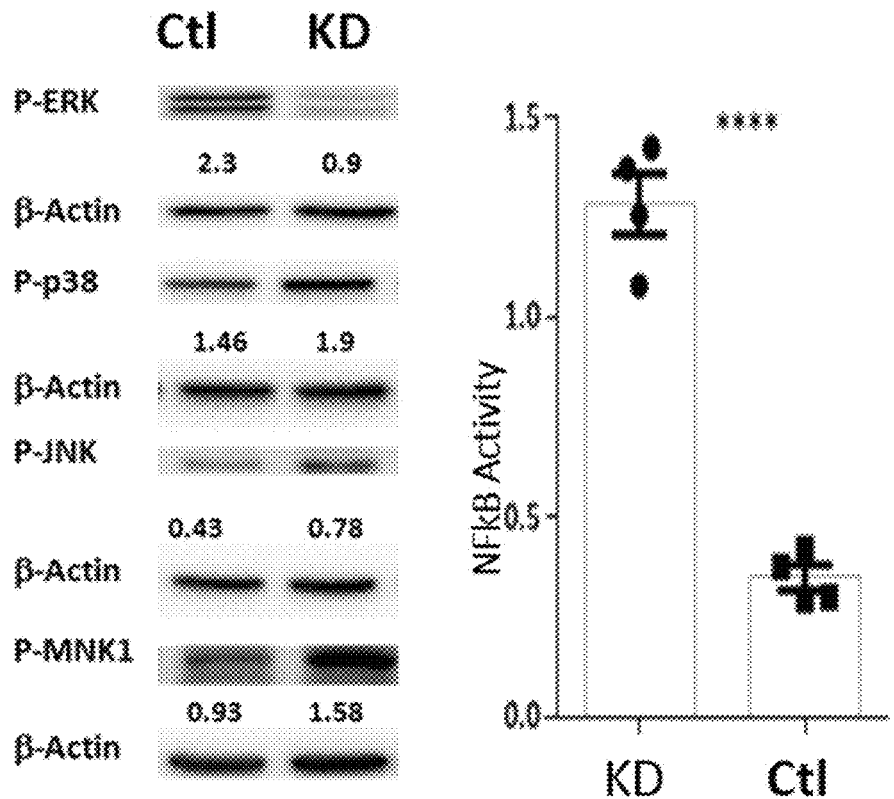
Figure 7D:
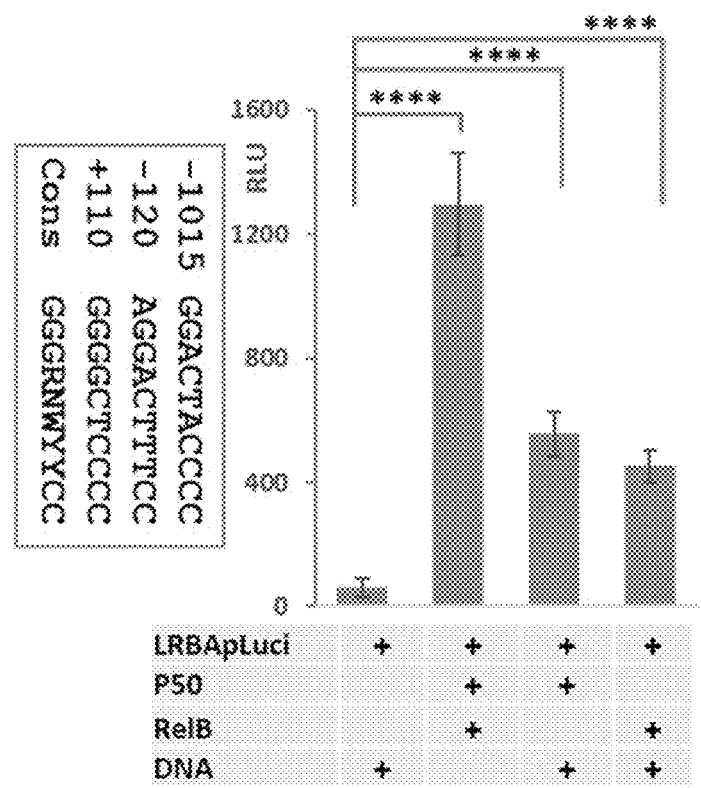

SEQ ID NOs:15-18: NFkB binding site of LRBA promoter (FIG. 7D).

Figures 8A, 8B:
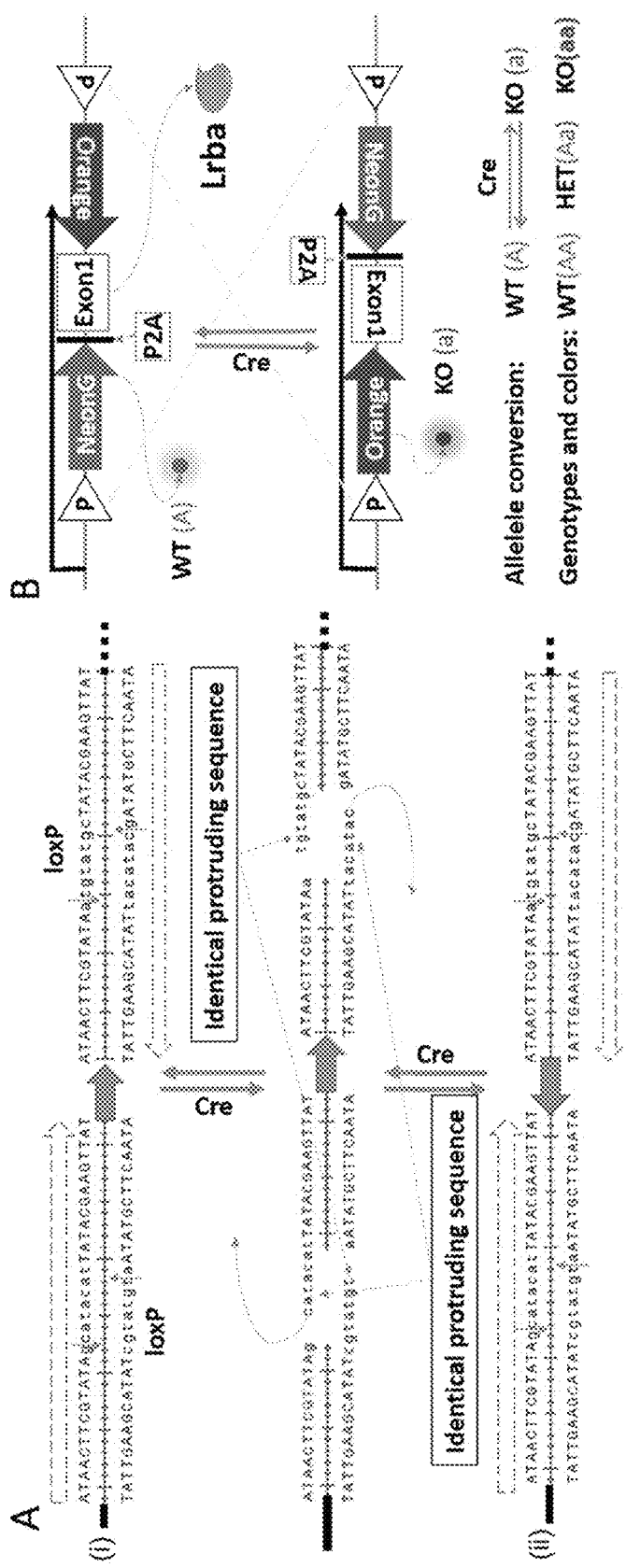
FIGS. 8A-8C. Principle of Genebow and Cloning strategy.

SEQ ID NOs:19-30: Locus of Cre recombinase-mediated crossover (FIG. 8A).

Figure 12A:
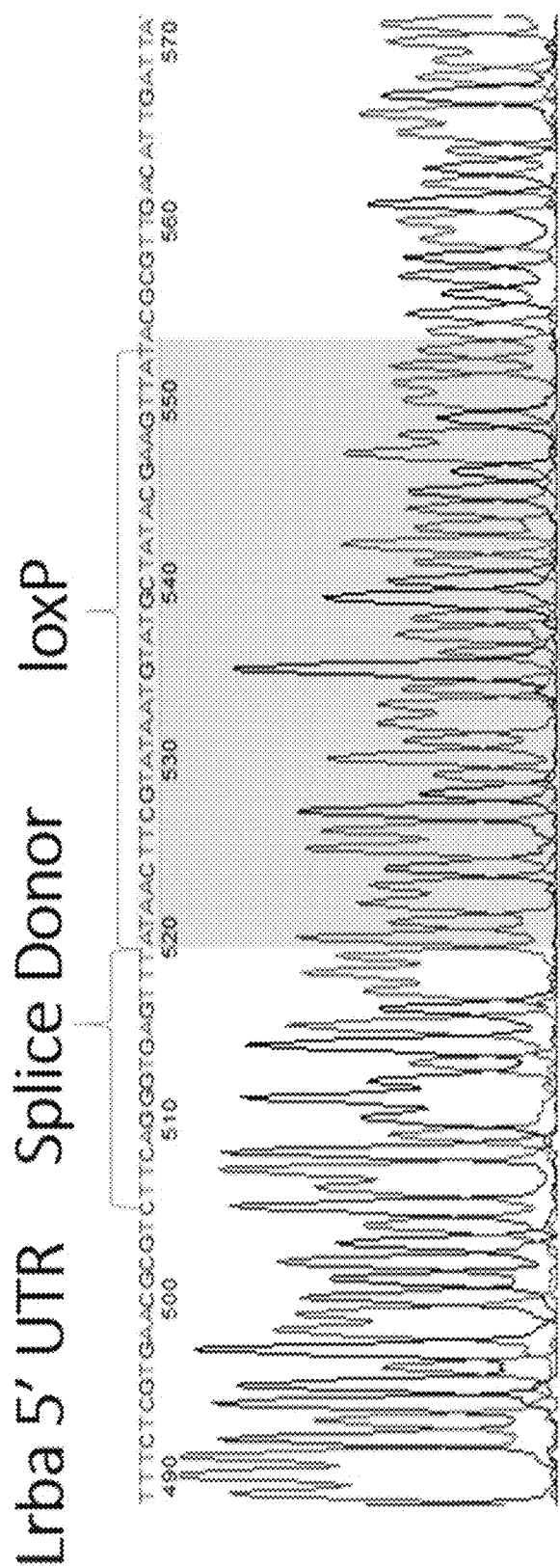

SEQ ID NO:31: Sequence at 5' junction of TCLC cassette insertion (FIG. 12A).

DETAILED DESCRIPTION OF THE INVENTION

An aspect of the invention concerns non-human animal models useful, for example, in studying gene-gene interactions, wherein the animal model comprises nine genotypes of two genes specifically labeled with four distinct detectable labels. In some embodiments, the two genes comprise a wild-type first gene (A), a wild-type second gene (B), an inactivated form of the first gene (a), and an inactivated form of the second gene (b), wherein the four distinct detectable labels comprise:

a first label co-expressed with the wild-type first gene (A), a second label co-expressed with the inactivated form of the first gene (a), a third label co-expressed with the wild-type second gene (B), and a fourth label co-expressed with the inactivated form of the second gene (b).

In some embodiments, the animal model comprises:

(a) a first genotype comprising homozygous alleles for the wild-type first gene (AA) and homozygous alleles for the wild-type second gene (BB), wherein the wild-type first gene (A) is co-expressed with the first label and the wild-type second gene (B) is co-expressed with the third label;

(b) a second genotype comprising homozygous alleles for the wild-type first gene (AA), one allele for the wild-type second gene (B), and one allele for the inactivated form of the second gene (b), wherein the first gene (A) is co-expressed with the first label, the second gene (B) is co-expressed with the third label, and wherein the allele for the inactivated form of the second gene (b) is co-expressed with the fourth label;

(c) a third genotype comprising homozygous alleles for the wild-type first gene (AA) and homozygous alleles for the inactivated form of the second gene (bb), wherein the homozygous alleles for the wild-type first gene (AA) are co-expressed with the first label, and wherein the homozygous alleles for the inactivated form of the second gene (bb) are co-expressed with the fourth label;

(d) a fourth genotype comprising one allele for the wild-type first gene (A), one allele for the inactivated version of the first gene (a), and homozygous alleles for the wild-type second gene (BB), wherein allele for the wild-type first gene (A) is co-expressed with the first label, the allele for the inactivated version of the first gene (a) is co-expressed with the second label, and the homozygous alleles for the wild-type second gene (BB) are co-expressed with the third label;

(e) a fifth genotype comprising one allele for the wild-type first gene (A), one allele for the inactivated version of the first gene (a), one allele for the wild-type second gene (B), and one allele for the inactivated form of the second gene (b), wherein the allele for the wild-type first gene (A) is co-expressed with the first label, the allele for the inactivated version of the first gene (a) is co-expressed second label, wherein the allele for the wild-type second gene (B) is co-expressed with the third label, and wherein the allele for the inactivated form of the second gene (b) is co-expressed with the fourth label;

(f) a sixth genotype comprising one allele for the wild-type first gene (A), one allele for the inactivated version of the first gene (a), and homozygous alleles for the inactivated version of the second gene (bb), wherein the allele for the wild-type first gene (A) is co-expressed with the first label, the allele for the inactivated version of the first gene (a) is co-expressed second label, and wherein the homozygous alleles for the inactivated form of the second gene (bb) are co-expressed with the fourth label;

(g) a seventh genotype comprising homozygous alleles for the inactivated version of the first gene (aa), and homozygous alleles for the wild-type second gene (BB), wherein the homozygous alleles for the inactivated version of the first gene (aa) are co-expressed with the second label, and wherein the homozygous alleles for the wild-type second gene (BB) are co-expressed with the third label;

(h) an eighth genotype comprising homozygous alleles for the inactivated version of the first gene (aa), one allele for the wild-type second gene (B), and one allele for the inactivated form of the second gene (b), wherein the homozygous alleles for the inactivated version of the first gene (aa) is co-expressed with the second label, the allele for the wild-type second gene (B) is co-expressed with the third label, and wherein the one allele for the inactivated form of the second gene (b) is co-expressed with the fourth label; and (i) a ninth genotype comprising homozygous alleles for the inactivated version of the first gene (aa), and homozygous alleles for the inactivated version of the second gene (bb), wherein the homozygous alleles for the inactivated version of the first gene (aa) is co-expressed with the second label, and wherein the homozygous alleles for the inactivated version of the second gene (bb) is co-expressed with the fourth label.

Genes may be inactivated by various methods, such as insertion, deletion, substitution, and/or recombination.

The first and second genes may be any genes of interest. Any two genes that at least potentially interact with each other either, physically or genetically, are suitable to be selected and studied using this animal model. In some embodiments, the first gene is Lrba and the second gene is NFkB, or vice-versa. These two genes are used as examples herein. Gene pairs that are important in human diseases are particularly advantageous to use in the animal model in place of Lrba and NFkB, include, for example, P53 and MDM2, NFkB and NOTCH1, EGFR and AKT1 gene pairs.

In some embodiments, the detectable labels are fluorescent labels or luminescent labels.

In some embodiments, the animal model is a rodent, such as a mouse. In some embodiments, the animal model is a primate.

Another aspect of the invention includes a method for studying gene-gene interaction, comprising: providing a non-human animal model of the invention; and analyzing the interaction of the two genes specifically labeled with four distinct detectable labels. In some embodiments of the method, the analysis is carried out by analyzing the characteristics and/or behavior of the animal model or one or more cell populations of the animal model. In some embodiments, the analysis includes subjecting cells of the animal model to flow cytometry. In some embodiments of the method, the analysis is carried out in the presence and/or absence of an exogenous agent administered to the animal model.

In some embodiments of the method, the analysis includes measuring or otherwise detecting a detectable label (e.g., one label, some of the labels, or all of the labels) of one of the genes (the label signal) and, optionally, comparing the measured detectable label (signal) to that of the other gene. Depending upon the type of label, the signal may be detected and optionally quantitatively measured using the appropriate modality for the type of label.

In some embodiments of the method, the two genes comprise a wild-type first gene (A), a wild-type second gene (B), an inactivated form of the first gene (a), and an inactivated form of the second gene (b), wherein the four distinct detectable labels comprise:

a first label co-expressed with the wild-type first gene (A),
a second label co-expressed with the inactivated form of the first gene (a),
a third label co-expressed with the wild-type second gene (B), and
a fourth label co-expressed with the inactivated form of the second gene (b); and
wherein the analyzing comprises measuring one or more of the first label, second label, third label, or fourth label.

In some embodiments of the method, the animal comprises:

(a) a first genotype comprising homozygous alleles for the wild-type first gene (AA) and homozygous alleles for the wild-type second gene (BB), wherein the wild-type first gene (A) is co-expressed with the first label and the wild-type second gene (B) is co-expressed with the third label;

(b) a second genotype comprising homozygous alleles for the wild-type first gene (AA), one allele for the wild-type second gene (B), and one allele for the inactivated form of the second gene (b), wherein the first gene (A) is co-expressed with the first label, the second gene (B) is co-expressed with the third label, and wherein the allele for the inactivated form of the second gene (b) is co-expressed with the fourth label;

(c) a third genotype comprising homozygous alleles for the wild-type first gene (AA) and homozygous alleles for the inactivated form of the second gene (bb), wherein the homozygous alleles for the wild-type first gene (AA) are co-expressed with the first label, and wherein the homozygous alleles for the inactivated form of the second gene (bb) are co-expressed with the fourth label;

(d) a fourth genotype comprising one allele for the wild-type first gene (A), one allele for the inactivated version of the first gene (a), and homozygous alleles for the wild-type second gene (BB), wherein allele for the wild-type first gene (A) is co-expressed with the first label, the allele for the inactivated version of the first gene (a) is co-expressed with the second label, and the homozygous alleles for the wild-type second gene (BB) are co-expressed with the third label;

(e) a fifth genotype comprising one allele for the wild-type first gene (A), one allele for the inactivated version of the first gene (a), one allele for the wild-type second gene (B), and one allele for the inactivated form of the second gene (b), wherein the allele for the wild-type first gene (A) is co-expressed with the first label, the allele for the inactivated version of the first gene (a) is co-expressed second label, wherein the allele for the wild-type second gene (B) is co-expressed with the third label, and wherein the allele for the inactivated form of the second gene (b) is co-expressed with the fourth label;

(f) a sixth genotype comprising one allele for the wild-type first gene (A), one allele for the inactivated version of the first gene (a), and homozygous alleles for the inactivated version of the second gene (bb), wherein the allele for the wild-type first gene (A) is co-expressed with the first label, the allele for the inactivated version of the first gene (a) is co-expressed second label, and wherein the homozygous alleles for the inactivated form of the second gene (bb) are co-expressed with the fourth label;

(g) a seventh genotype comprising homozygous alleles for the inactivated version of the first gene (aa), and homozygous alleles for the wild-type second gene (BB), wherein the homozygous alleles for the inactivated version of the first gene (aa) are co-expressed with the second label, and wherein the homozygous alleles for the wild-type second gene (BB) are co-expressed with the third label;

(h) an eighth genotype comprising homozygous alleles for the inactivated version of the first gene (aa), one allele for the wild-type second gene (B), and one allele for the inactivated form of the second gene (b), wherein the homozygous alleles for the inactivated version of the first gene (aa) is co-expressed with the second label, the allele for the wild-type second gene (B) is co-expressed with the third label, and wherein the one allele for the inactivated form of the second gene (b) is co-expressed with the fourth label; and (i) a ninth genotype comprising homozygous alleles for the inactivated version of the first gene (aa), and homozygous alleles for the inactivated version of the second gene (bb), wherein the homozygous alleles for the inactivated version of the first gene (aa) is co-expressed with the second label, and wherein the homozygous alleles for the inactivated version of the second gene (bb) is co-expressed with the fourth label; and wherein the analyzing includes measuring one or more of the first label, second label, third label, or fourth label (i.e., one label, two labels, three labels, or all four labels).

Another aspect of the invention includes a method for studying gene-gene interaction in vitro, comprising: providing a population of cells (ex vivo) from the non-human animal model of the invention (the cells may be in isolated form, or as a tissue, for example); and analyzing the interaction of the two genes specifically labeled with four distinct detectable labels. In some embodiments of the method, the analyzing comprises analyzing the characteristics and/or behavior of the cells. In some embodiments of the method, the analyzing comprises subjecting cells of the animal model to flow cytometry.

In some embodiments of the method, the analyzing is carried out in the presence and/or absence of an exogenous agent administered to the animal in vivo or brought into contact with the cells in vitro.

In some embodiments of the method, the analyzing comprises measuring or otherwise detecting the detectable label of one of the genes and, optionally, comparing the measured detectable label to that of the other gene. Depending upon the type of label, the signal may be detected and optionally quantitatively measured using the appropriate modality for the type of label.

In some embodiments of the method, the two genes comprise a wild-type first gene (A), a wild-type second gene (B), an inactivated form of the first gene (a), and an inactivated form of the second gene (b), wherein the four distinct detectable labels comprise:

a first label co-expressed with the wild-type first gene (A), a second label co-expressed with the inactivated form of the first gene (a), a third label co-expressed with the wild-type second gene (B), and a fourth label co-expressed with the inactivated form of the second gene (b); and wherein said analyzing comprises measuring one or more of the first label, second label, third label, or fourth label (i.e., one, two, three, or all four labels).

In some embodiments of the method, the animal comprises:

(a) a first genotype comprising homozygous alleles for the wild-type first gene (AA) and homozygous alleles for the wild-type second gene (BB), wherein the wild-type first gene (A) is co-expressed with the first label and the wild-type second gene (B) is co-expressed with the third label;

(b) a second genotype comprising homozygous alleles for the wild-type first gene (AA), one allele for the wild-type second gene (B), and one allele for the inactivated form of the second gene (b), wherein the first gene (A) is co-expressed with the first label, the second gene (B) is co-expressed with the third label, and wherein the allele for the inactivated form of the second gene (b) is co-expressed with the fourth label;

(c) a third genotype comprising homozygous alleles for the wild-type first gene (AA) and homozygous alleles for the inactivated form of the second gene (bb), wherein the homozygous alleles for the wild-type first gene (AA) are co-expressed with the first label, and wherein the homozygous alleles for the inactivated form of the second gene (bb) are co-expressed with the fourth label;

(d) a fourth genotype comprising one allele for the wild-type first gene (A), one allele for the inactivated version of the first gene (a), and homozygous alleles for the wild-type second gene (BB), wherein allele for the wild-type first gene (A) is co-expressed with the first label, the allele for the inactivated version of the first gene (a) is co-expressed with the second label, and the homozygous alleles for the wild-type second gene (BB) are co-expressed with the third label;

(e) a fifth genotype comprising one allele for the wild-type first gene (A), one allele for the inactivated version of the first gene (a), one allele for the wild-type second gene (B), and one allele for the inactivated form of the second gene (b), wherein the allele for the wild-type first gene (A) is co-expressed with the first label, the allele for the inactivated version of the first gene (a) is co-expressed second label, wherein the allele for the wild-type second gene (B) is co-expressed with the third label, and wherein the allele for the inactivated form of the second gene (b) is co-expressed with the fourth label;

(f) a sixth genotype comprising one allele for the wild-type first gene (A), one allele for the inactivated version of the first gene (a), and homozygous alleles for the inactivated version of the second gene (bb), wherein the allele for the wild-type first gene (A) is co-expressed with the first label, the allele for the inactivated version of the first gene (a) is co-expressed second label, and wherein the homozygous alleles for the inactivated form of the second gene (bb) are co-expressed with the fourth label;

(g) a seventh genotype comprising homozygous alleles for the inactivated version of the first gene (aa), and homozygous alleles for the wild-type second gene (BB), wherein the homozygous alleles for the inactivated version of the first gene (aa) are co-expressed with the second label, and wherein the homozygous alleles for the wild-type second gene (BB) are co-expressed with the third label;

(h) an eighth genotype comprising homozygous alleles for the inactivated version of the first gene (aa), one allele for the wild-type second gene (B), and one allele for the inactivated form of the second gene (b), wherein the homozygous alleles for the inactivated version of the first gene (aa) is co-expressed with the second label, the allele for the wild-type second gene (B) is co-expressed with the third label, and wherein the one allele for the inactivated form of the second gene (b) is co-expressed with the fourth label; and (i) a ninth genotype comprising homozygous alleles for the inactivated version of the first gene (aa), and homozygous alleles for the inactivated version of the second gene (bb), wherein the homozygous alleles for the inactivated version of the first gene (aa) is co-expressed with the second label, and wherein the homozygous alleles for the inactivated version of the second gene (bb) is co-expressed with the fourth label; and wherein the analyzing comprises measuring one or more of the first label, second label, third label, or fourth label (i.e., one, two, three, or all four labels).

Animals

The non-human animal model is preferably a mammal. For example, the animal model may be a rodent or non-human primate.

In some embodiments, the animal is selected from the group consisting of a mouse, rat, guinea pig, hamster, gerbil, pig, cow, dog, wolf, coyote, jackel, and cat. In some embodiments, the animal model is a monkey or ape. In some embodiments, the animal model is a primate selected from the group consisting of a macaque, marmoset, tamarin, spider monkey, vervet monkey, squirrel monkey, and baboon. In some embodiments, the animal model is an ape selected from the group consisting of a gorilla, chimpanzee, orangutan, and gibbon. The animal model may be a hybrid of two non-human animals (e.g., dog-wolf).

The animal model may have any desired genetic background. The animals may be crossed with many strains, and the genes may be studied with a wide genetic background, which is desired to recapitulate the complexity of human disease. As controls are not required, establishing isogenic strains are not necessary. The animal model of the invention can be crossed with many strains simultaneously and the function of a gene can be studied in a wide genetic background, which is desirable for recapitulating human complex diseases and can save time and resources.

The animal may be further modified at the genetic or epigenetic level so as to be useful in modeling a particular disease, such as cancer, cardiovascular disease, a metabolic disease such as diabetes, or a monogenic disease. For example, the animal model may be further modified to model Down Syndrome, cystic fibrosis, cancer, glaucoma, type-I diabetes, type-II diabetes, epilepsy, heart disease, muscular dystrophy, or gynecological tumors.

Down Syndrome—One of the most common genetic birth defects in humans, occurring once in every 800 to 1,000 live births, Down syndrome results from an extra copy of chromosome 21, an abnormality known as trisomy. The Ts65Dn mouse, developed at The Jackson Laboratory, mimics trisomy 21 and exhibits many of the behavioral, learning, and physiological defects associated with the syndrome in humans, including mental deficits, small size, obesity, hydrocephalus and thymic defects. This model represents the latest and best improvement of Down syndrome models to facilitate research into the human condition.

Cystic Fibrosis (CF)—The Cftr knockout mouse has helped advance research into cystic fibrosis, the most common fatal genetic disease in the United States today, occurring in approximately one of every 3,300 live births. Scientists now know that CF is caused by a small defect in the gene that manufactures CFTR, a protein that regulates the passage of salts and water in and out of cells. Studies with the Cftr knockout have shown that the disease results from a failure to clear certain bacteria from the lung, which leads to mucus retention and subsequent lung disease. These mice have become models for developing new approaches to correct the CF defect and cure the disease.

Cancer—The p53 knockout mouse has a disabled Trp53 tumor suppressor gene that makes it highly susceptible to various cancers, including lymphomas and osteosarcomas. The mouse has emerged as an important model for human Li-Fraumeni syndrome, a form of familial breast cancer.

Glaucoma—The DBA/2J mouse exhibits many of the symptoms that are often associated with human glaucoma, including elevated intraocular pressure. Glaucoma is a debilitating eye disease that is the second leading cause of blindness in the United States.

Type 1 Diabetes—This autoimmune disease, also known as Juvenile Diabetes, or Insulin Dependent Diabetes Mellitus (IDDM), accounts for up to 10 percent of diabetes cases. Non-obese Diabetic (NOD) mice are enabling researchers to identify IDDM susceptibility genes and disease mechanisms.

Type 2 Diabetes—A metabolic disorder also called Non-Insulin Dependent Diabetes Mellitus (NIDDM), this is the most common form of diabetes and occurs primarily after age 40. The leading mouse models for NIDDM and obesity research were all developed at The Jackson Laboratory: Cpefat, Lepob, Leprdb and tub.

Epilepsy—The "slow-wave epilepsy," or swe, mouse is the only model to exhibit both of the two major forms of epilepsy: petit mal (absence) and grand mal (convulsive). It shows particular promise for research into absence seizures, which occur most often in children.

Heart Disease—Elevated blood cholesterol levels and plaque buildup in arteries within three months of birth (even on a low-fat diet) are characteristics of several experimental models for human atherosclerosis: the Apoe knockout mouse and C57BL/6J.

Muscular Dystrophy—The Dmd mdx mouse is a model for Duchenne Muscular Dystrophy, a rare neuromuscular disorder in young males that is inherited as an X-linked recessive trait and results in progressive muscle degeneration.

Ovarian Tumors—The SWR and SWXJ mouse models provide excellent research platforms for studying the genetic basis of ovarian granulosa cell tumors, a common and very serious form of malignant ovarian tumor in young girls and post-menopausal women.

Reporters

The various genotypes are labeled with a detectable label (also referred to herein as a reporter) in order to detect and track promoter activity and gene expression, e.g., by flow cytometry. Thus, the reporter gene and the first gene and second gene are operably linked such that they are co-expressed.

Such detectable labels are known in the art, and include, for example, fluorescent reporter proteins encoded by fluorescent reporter genes. Preferably, each reporter can be detected in a living animal. Thus, the amount, distribution, proliferation, movement, properties, and behavior of the labeled cells can thus be assessed and, optionally, monitored.

Exemplary reporters include light-emitting reporters, such as fluorescent and luminescent reporters. Polypeptides that result in the generation of light in a living organism (bioluminescence) include, but are not limited to, various luciferases, green fluorescent protein (GFP), yellow fluorescent protein (YFP) and aequorin (Wilson and Hastings, *Annu. Rev. Cell Dev. Biol.*, 1998, 14:197-230). Fluorescence reporters have many diverse uses, the most common of which are for fluorescence microscopy and also for flow cytometry. In both cases internal expression of the fluorescence reporter, using a reporter plasmid system, allows simple assessment of cell properties and/or behavior.

Luciferase is a luminescent molecule, and thus does not require excitation in order to generate light. It does typically require a substrate (e.g., luciferin, an aldehyde or coelenterazine), an energy source (e.g., ATP) and oxygen. In the case of bacterial luciferases, the genes encoding the substrate can be supplied the same vector as the gene(s) encoding the luciferase enzyme, thus eliminating the need for exogenously-supplied substrate (see, e.g., U.S. Pat. No. 5,650,135).

In some embodiments, the reporter is selected from the group consisting of red fluorescent protein (RFP), green fluorescence protein (GFP), yellow fluorescence protein (YFP), and cyano fluorescence protein (CFP). Polynucleotide cassettes encoding such polypeptides may be transfected into the target site as extra-chromosomal genetic elements (e.g., plasmids) or are stably incorporated into the genome (e.g., "hopped" in using, for example, a transposon).

If the reporter is a light-emitting reporter, method of measurement incluude using a photon detection device, such as an intensified CCD camera, a cooled CCD camera, or any other photon detection device with a high sensitivity. However, other methods may be used. For example, a light-emitting reporter may also be detected using a sensitive luminometer; a radioactive reporter may be detected by counts, X-ray imaging or scintillation.

The term "operatively linked" or "operably linked" refers to the connection of elements being a part of a functional unit such as a gene or an open reading frame (e.g., encoding LRBA). Accordingly, by operatively linking a promoter to a nucleic acid sequence encoding a gene product such as a polypeptide the two elements becomes part of the functional unit—a gene. The linking of the expression control sequence (promoter) to the nucleic acid sequence enables the transcription of the nucleic acid sequence directed by the promoter. By operatively linking two heterologous nucleic acid sequences encoding a polypeptide the sequences becomes part of the functional unit—an open reading frame encoding a protein or proteins comprising the amino acid sequences encoded by the heterologous nucleic acid sequences. By operatively linking two coding sequences, the sequences can be co-expressed.

To alleviate the limitations of current animal model techniques, a method for studying gene-gene interactions in a single animal (e.g., mouse) is provided (FIG. 1): Genebow, coined from the Brainbow [8]. The method of the invention aims to achieve 1) high sensitivity: phenotypes of the nine genotypes of the two genes from one mouse can be studied by flow cytometry in a single tube with high sensitivity due to the elimination of experimental variations; 2) congenic strain-independence: since within a single animal, each genotype has the other eight genotypes as controls, establishing a congenic strain is not necessary; 3) high specificity: the gene expression can be turned on/off (e.g., by the TetOn system). Phenotypes can be specifically attributed to the gene if they change in response to the switching gene expression on/off. The mutations of lipopolysaccharide-responsive, beach and anchor containing (LRBA) cause immunodeficiency and autoimmunity with highly variable symptoms and LRBA interacts with many crucial regulators including NFkB in vitro [3-5]. This animal model will permit study of how LRBA interacts with these regulators in vivo to better understand the immune system. As a proof of concept, Lrba and Nfkb1 can be used for the model.

The Genebow is a revolutionary technique for rapid, specific and sensitive study of the gene-gene interaction in any animals over a wide genetic background, which is essential to recapitulate the genetic interactions of human diseases. The PI has cloned the LRBA gene, contributed fifteen GenBank entries and generated six mouse models including a conditional knockout (KO) model [9,10]. The PI has also developed a novel CRISPR cloning method [11]. The expertise will ensure the accomplishment of this proposal.

The GWA studies have demonstrated that many human common diseases, such as cancer, cardiovascular disease, diabetes and allergic disease, and even rare "monogenic" diseases, result from the complex interplay of many genes and environmental factors, and that individual gene contribution typically is small and can be masked by genetic and environmental variations [1,12-18]. The history of mouse genetics also makes it clear that the genetic background can cause considerable phenotypic variation in the mice with the same targeted gene [19]. These variables pose a great challenge in studying human disease gene-gene interactions. GWA studies have failed to establish common variant risk for the majority of common diseases [15,20]. Animal models are indispensable and powerful tools, tremendously increasing knowledge of gene function. However, animal techniques that can sensitively study gene-gene interactions over a wide genetic background required to decode complex human diseases have yet to be developed. Current animal models are dependent on establishing a congenic strain and on the presumptions that the animals within the strain are identical and that reproducible data can be obtained [6,7]. Unfortunately, these animals are still subject to genetic, epigenetic and environmental variations. These variations may stem from the "passenger DNA" from the original targeted genome, epigenetic modifications of DNA, non-coding RNAs and RNA editing, and bacterial and viral infections [21-28]. All of these variations can play an important role in determining phenotype, which can result in high background noise, low sensitivity or even false data, e.g., the phenotypes originally attributed to the targeted gene actually attribute to other genes [29-33]. Experimental protocol also can introduce significant variations [34-36]. Moreover, the genetic diversity of current mouse models is only a fraction of that presented in wild mice [37], as the classical inbred mouse strains are derived from the same ancestors. In addition, most gene-targeting studies have focused on one strain, which is analogous to only a single human in the sense of genetic diversity [38]. To recapitulate the complex human disease gene-gene interactions, a gene should be studied in a variety of inbred strains and wild mice to increase genetic diversity to find the genetic modifiers of the targeted gene [39,40]. However, there is no such technique available, since the outbreeding will lose homogeneity, making it virtually impossible to study the targeted gene, and the intra-"congenic" strain animals from backcrossing are not identical.

To address these limitations, the inventors provide a novel concept to study gene-gene interactions in a single animal (FIG. 1) to achieve 1) high sensitivity: phenotypes of the nine genotypes from one mouse can be studied by flow cytometry in a single tube with high sensitivity due to the elimination of experimental variations and the power of flow cytometry, which has an analysis rate of up to 40,000 cells per second; 2) congenic strain-independence: since each genotype has the other eight genotypes as controls in a single mouse, establishment of a congenic strain is not necessary; 3) high specificity: the gene can be turned on/off by the TetOn system, allowing spatiotemporal control of gene expression. Phenotypes can be specifically attributed to the gene of interest if they change in response to switching the gene expression on/off. The nine-in-one model allows the rapid, specific and highly sensitive study of the genetic interaction of any two genes. This will form the base to study the gene-gene interactions in any animals, including non-human primates [41], on a wide genetic background, which is essential to recapitulate human diseases.

Brainbow is a process to label neuron cells with a random choice of up to 90 distinctive FP colors so that adjacent cells can be distinguished from each other to visually study neural connections in the brain [8,42]. The Genebow technique can be used to label cells with many distinct labels (e.g., colors) to study interactions of adjacent cells similar to Brainbow and other similar methods [43-45]. However, the Genebow labeling, unlike the other methods, is associated with the nine different genotypes and the promoter activities of the two genes. Therefore, it can be used to study gene-gene interaction with high sensitivity and specificity in a single animal. In addition, since each genotype has the other eight genotypes as controls in a single animal, there is no need for genotype control animals. Thus, a congenic strain establishment is not necessary. Any animal that has the genotype [aabb(rtTACreERT2)+/−, usually F2] can be used directly for experiments. This enables a rapid genetic background switch (~2 months) of the two targeted genes in many different inbred strains and wild animals (e.g., wild mice). As stated above, different genetic backgrounds may help to identify new genetic modifiers of the two genes, from which a gene interaction networks can be discovered. This is virtually impossible to accomplish using the current existing techniques.

There are alternative ways in which the animal model can be produced, including alternative ways to switch the genes on and off. An alternative to the CRISPR method, the traditional knock-in method based on mouse embryonic stem cells can be used to obtain this model. Similar to the Cre-loxP technology, Flp-FRT or PhiC31 Integrase-mediated recombination can also be used in the place of Cre-loxP recombination to turn on gene expression. In order to produce other species of animal models, the species-specific sequences will be used to replace mouse sequences. Other potential modifications include, for example, fertilized eggs and foster mothers from that species.

Figure 1:
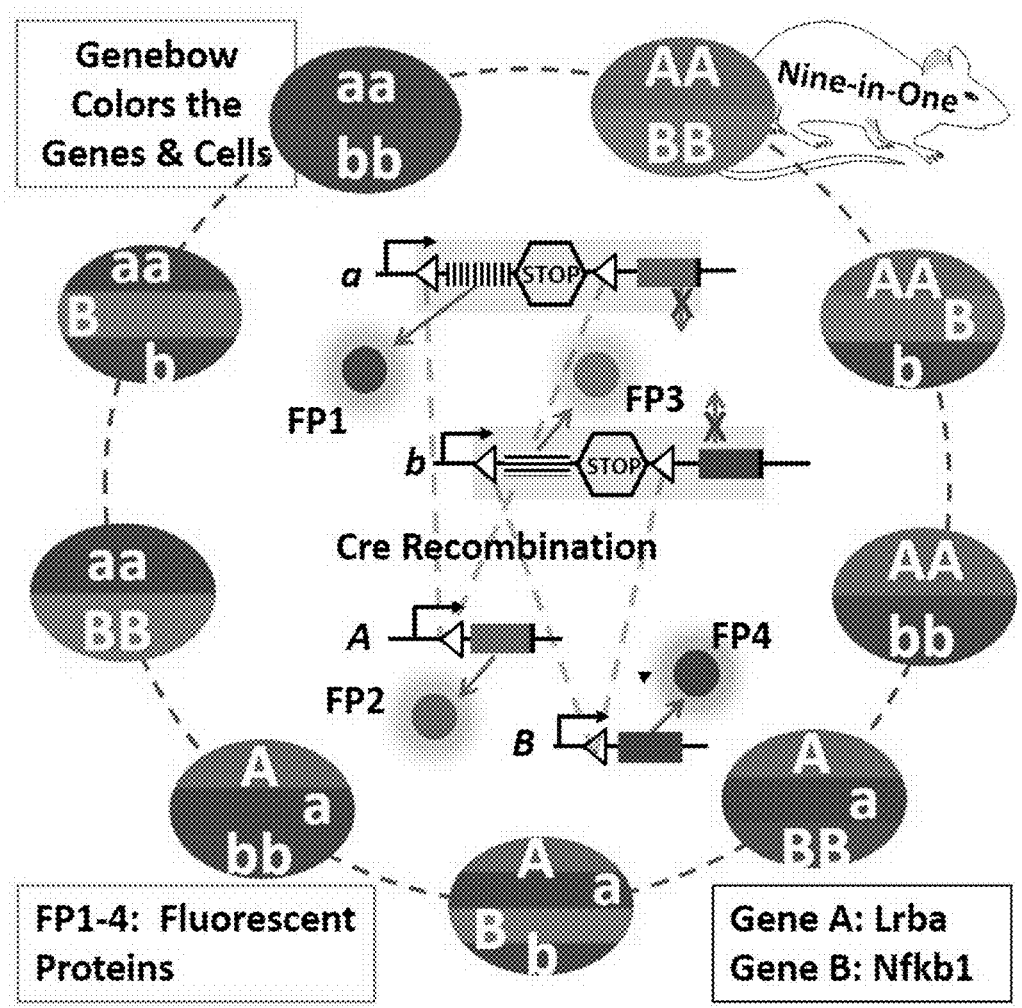
FIG. 1. Genebow: the nine genotypes of the two genes are labeled with four different FPs in a single mouse. Two transcription control FP cassettes (TCFP, shaded) and the Cre gene will be inserted into the gene A, gene B and the Rosa26 loci, respectively by the CRISPR technique. FP2 and FP4 co-express with gene A and gene B, respectively, while FP1 and FP3 "co-express" with the STOP, which stops downstream gene expression. The Cre partial cleavage of the two loxP sites (triangle) will result in nine genotypes and cells with specific FP labeling. Genebow can also detect whether the promoter of a gene has activity. For example, if neither of the two FP genes knocked into the gene locus is expressed, it indicates that the promoter of the gene is not active. Oval represents cells. A, B, wild type alleles; a, b, knockout alleles. Arrows denote gene expression. X=No translation.
Figure 2E:
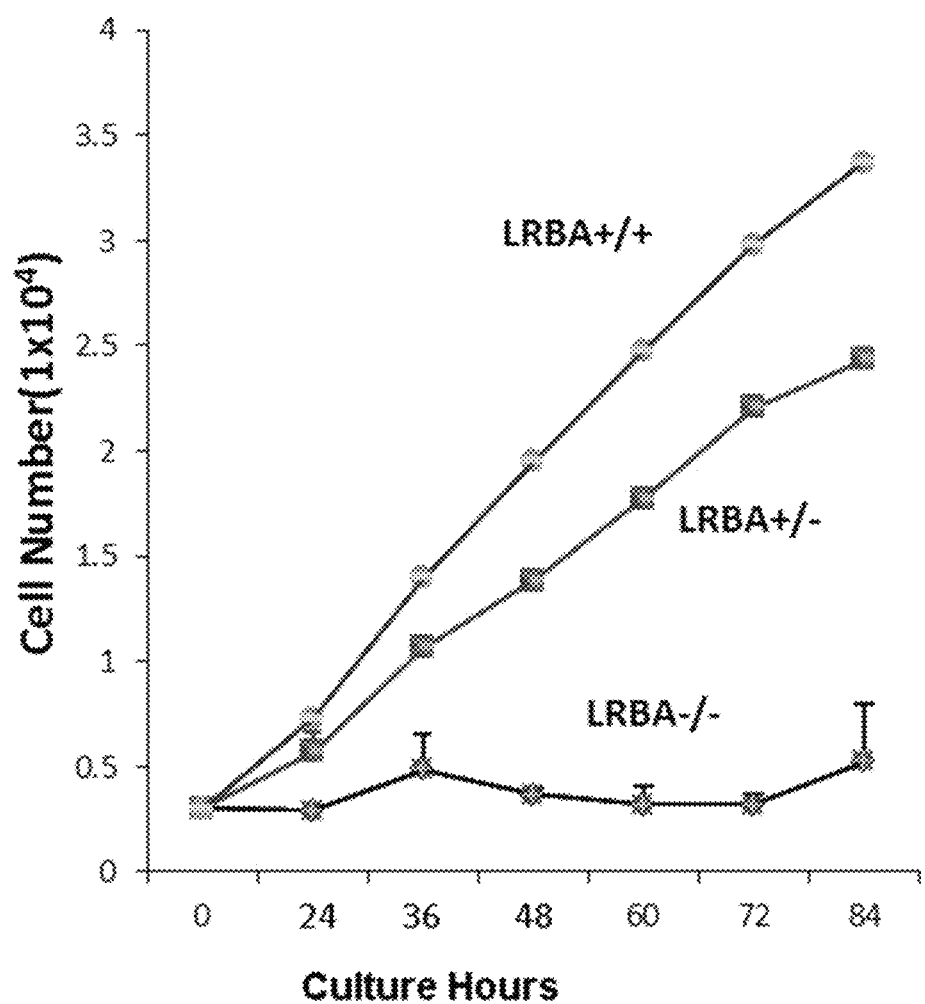

As an alternative to the fluorescent proteins (FP), two Fluorogen activating peptide—FAP-Tags®, a new class of small genetically encoded reporters that exhibit fluorescence (Green or red) only in the presence of micromolar concentrations of particular nontoxic soluble fluorogens, can be used in the place of two FPs (http://spectragenetics.com/). Therefore the two genes can be labeled with two fluorescent proteins and two FAP-tags. The FAP-tags can be used directly with Fluorogens to produce desired fluorescent colors. They also have Epitope Tag sequences that can be labeled with any colors, which gives the flexibility of accommodating multiplex fluorescence assay by flow cytometry and fluorescent microscopy. An LSRII flow cytometer may have the capacity of detecting 15 colors. The labeling of the two genes uses two fixed fluorescent colors and two other flexible colors. There are 11 color available to label cell surface markers of interest to conduct almost any multiplex fluorescence flow cytometry routinely used in research (FIG. 1).

Figure 6:
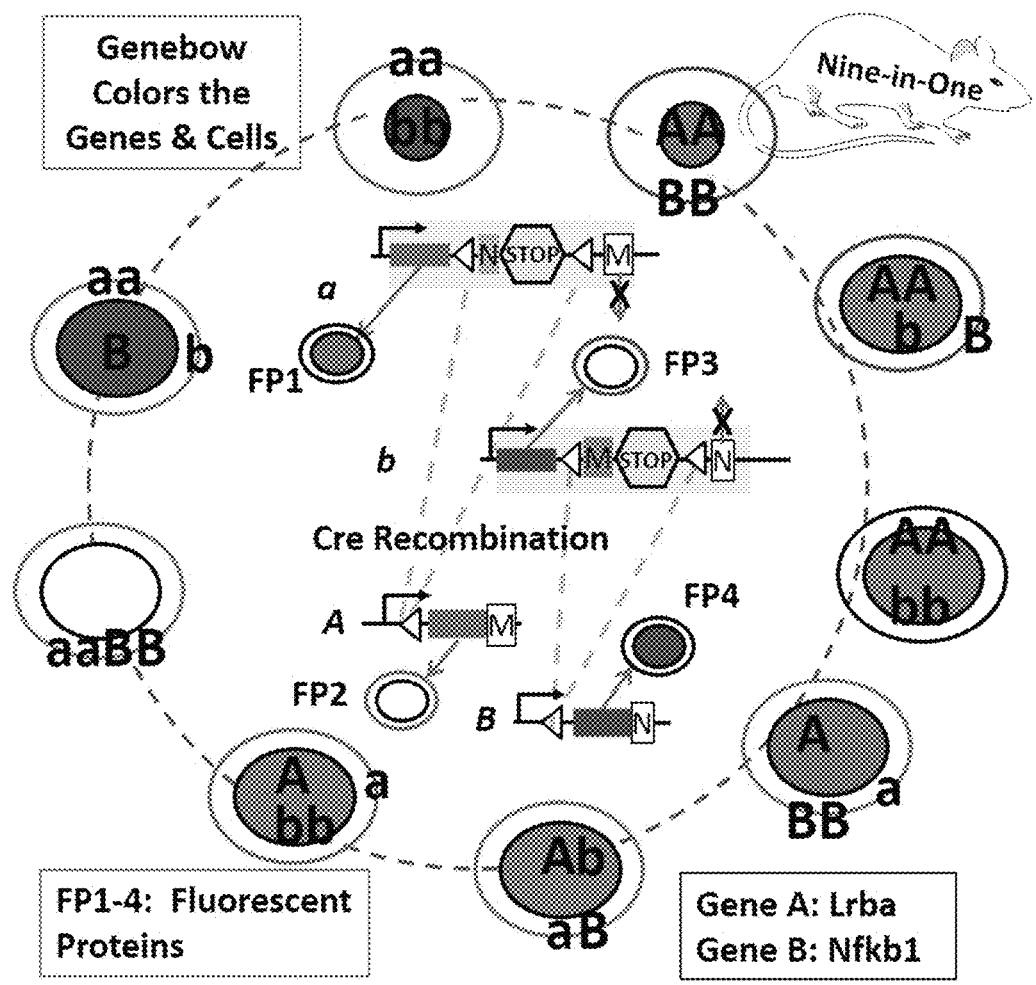
FIG. 6. Genebow: the nine genotypes of the two genes are labeled with two different FPs that localize to two different subcellular locations in a single mouse. Two transcription control FP cassettes (TCFP, shaded) and the Cre gene will be inserted into the gene A, gene B and the Rosa26 loci, respectively by the CRISPR technique. The FP1 and FP4 are separately tagged with a nuclear localization sequence (N) and will be localized in the nucleus. While the FP2 and FP3 are separately tagged (M) with a membrane localization sequence and will be localized in the cell membrane, FP2 and FP4 co-express with gene A and gene B, respectively, while FP1 and FP3 "co-express" with the STOP, which stops downstream gene expression. The Cre partial cleavage of the two loxP sites (triangle) will result in nine genotypes and cells with specific FP labeling, which can be detected by confocal fluorescent microscopy and image flow cytometry. Oval represents cells. A, B, wild type alleles; a, b, knockout alleles. Arrows denote gene expression. X=No translation.

An alternative labeling of the two genes is shown in FIG. 6. Each gene is labeled with only one label (with one fluorescence gene). However, the subcellular localization of each fluorescence protein can be switched from cell membrane to nucleus or vice versa. Therefore, this two-fluorescence-gene-labeling is equivalent to the four-fluorescence-gene-labeling described previously.

A vast array of experiments can be carried out using the animal model and cells obtained therefrom. Since each genotype of the nine genotypes of two genes is specifically labelled, e.g., with a color-code, it is not necessary to genotype cells in study. This will greatly facilitate the study of phenotype of the two genes. For example, lineage tracing of hematopoietic cells may be done: the 9 genotypes can be induced at early development of hematopoietic cells, e.g., hematopoietic stem cells, then trace the development of each genotype using flow cytometry and fluorescent microscopy, and answer the questions whether different genotypes have different development consequences in terms of cell numbers, cell types (B, T lymphocytes, monocytes, dendritic cells) and cell subtypes (CD4, CD8 T cells, B1 and B2 B cells, etc.). It is also possible to study lymphocyte and stromal cell interaction using the animal model. Lymphocytes undergo massive cell death at multiple developmental stages in order to eliminate non- or self-reactive lymphocytes through positive and negative selection, in which stromal cells play an important role. Since both lymphocytes and stromal cells are labeled with fluorescent colors specific to the genotypes, the influence of the different genotype of the stromal cells on the selection of lymphocytes can be studied. In addition, it is possible to study the cell-cell interactions of hematopoietic cells. Similarly, the cell-cell interaction play an important role in the activation or inhibition of hematopoietic cells, such as the activation of B cells by T cells, the inhibition of T cell proliferation by regulatory T cells.

Example 1 describes how to construct two target vectors for the two genes with the universal TCFP cassettes, the third target vector with the inducible Cre, and the reverse tetracycline transactivator (rtTA) gene will be constructed. The functionality of all three will be tested in vitro.

Example 2 describes how to generate the mouse model and model functionality. The clustered regularly interspaced short palindromic repeats (CRISPR) technique, which can quickly generate mutated mice at high efficiency, will be used to generate the model. The functionality of the model in terms of gene expression control and FP labeling will be tested by studying the genetic interaction of the two genes on cell apoptosis.

Following are examples that illustrate procedures for practicing the invention. These examples should not be construed as limiting. All percentages are by weight and all solvent mixture proportions are by volume unless otherwise noted.

EXAMPLE 1

Targeting Vector Construction and Functionality

1. Gene Labeling Strategy.
As shown in FIG. 1, the wild type (WT) allele (A) will be labeled with FP1, the KO allele (a) with FP2. The cells with alleles A and a will have two colors, FP1 and FP2. Thus the three genotypes of one gene can be specifically labeled with two FPs. To this end, FP2 and gene A are linked in frame with the porcine teschovirus-1 2A (P2A) sequence encoding a self-cleavable peptide, and they will be co-expressed. FP1 is placed downstream of the promoter of the gene A and will be expressed if the promoter is active. FP1 is followed by a STOP that serves as a stop signal for the transcription and translation of the downstream genes, i.e., FP2 and A genes. However, once the FP1 and the STOP are removed by the Cre/loxP system, FP2 and A will be expressed. Thus, FP1 (WT) and FP2 (KO) are exclusively expressed. Similarly, FP3 & 4 will be used to label gene B (FIG. 1). Together, the nine genotypes of the two genes can be specifically labeled (FIG. 1) and detected by flow cytometry.

2. Choosing Florescent Proteins (FPs).
Four bright FPs have been chosen for sensitive and specific detection: mNeonGreen, mRuby2, Aqua and iRFP670 with a relative brightness of 100, 46, 23 and 13, respectively [64]. EGFP and mRFP1 with a relative brightness of 36 and 13 have been successfully used to label cells [65]. These FPs do not overlap with each other in cytometry detection using the four lasers and detection filter sets as shown (FIGS. 3B and 3C). This ensures specific detection by flow cytometry (FIG. 3C).

3. Cloning Strategy.
For high throughput target construction, two universal TCFP cassettes will be constructed so the target repair template for any gene can be constructed as described in FIG. 3A. Gibson cloning kit (NEB) will be used to facilitate the cloning of the two universal TCFP cassettes [66,67]. The two target repair templates for Lrba and Nfkb1 will be assembled as described in FIG. 3A. The TCFP cassette is composed of the following components that have been tested previously. (A) Splice sites (1, 2 and 6 in FIG. 3A) for splicing out unwanted sequences that may impair translation of downstream coding sequences [1, splice donor (SD); 2, human β-globin (HBB) intron splice acceptor (SA) [44]; 6, rabbit β-globin SA [68]]. (B) FP reporter genes iRFP670 or mRuby2 (3); mNeonGreen or Aquamarine (Aqua) (7). iRFP670 is a near-infrared FP [69]. Aqua is superior to the popular form ECFP [70]. (C) STOP sequence (4) [71]. (D) Tetracycline responsive element (TRE) (5) [72-74]. (D) P2A (8). P2A peptide is used to link two proteins to be co-expressed by a single promoter [75]. Due to its small size (57 bp), high self-cleavability, and ability to produce an equal molar ratio of the two proteins, 2A is superior to IRES, which is large and causes differential expression of the two genes that it links [75].

4. Construction of the rtTA/CreERT2 Target Vector.
The tetracycline-inducible expression system has been used previously to turn on/off gene expression [76]. The Tet-On third generation tet-inducible gene expression system is 100-fold more Dox-sensitive than the original TetOn system. It has significantly reduced background, and also is widely cited [72-74]. The CreERT2 is a fusion protein, consisting of the loxP site-specific Cre recombinase linked to a triple mutant form of the ligand-binding domain of the human estrogen receptor, which does not bind its natural ligand but will bind the synthetic TAM. Cre-ERT2 is restricted to the cytoplasm and can only enter the nuclear compartment after exposure to TAM. Thus, it can be used to efficiently induce the recombinase activity by administration of TAM [77,78]. CreERT2 is currently the most successful CreER version [79]. The pMB80 (R26-CreER) (Addgene plasmid 12168) is a target vector for inserting CreERT2 into the Rosa26 locus [80]. The neomycin selection marker in this vector will be removed by Cre recombination in vitro and will be cleaved by a unique site enzyme PflFI just in the translation start codon ATG. Then, the rtTA-P2A (third generation TetOn gBlock) PCR fragment will be inserted and fused with the CreERT2 by Gibson cloning, so that rtTA and Cre-ERT2 can be coexpressed.

5. The Functionality of Three Target Vectors will be Validated before CRISPR Injection.

Each TCFP target vector and the rtTA/CreERT2 will be inserted into the JM8A3-N1 ES cells (passage #17, the Mouse Biology Program) as previously with the CRISPR technique [9]. The corrected targeted ES clones will be expanded, mixed, and subjected to (1) Doxycycline (Dox) induction of gene expression and (2) Tam induced Cre cleavage of the STOP sequence and gene expression. The four FP will be detected by flow cytometry. The gene expression of Lrba and Nfkb1 will be detected by real time PCR and Western blot and compared to that from the WT ES cells.

6. Preliminary Results and Feasibility.

The inventors have constructed an Lrba target vector from a BAC clone using recombination-mediated genetic engineering techniques: homologous recombineering (HR) and Gibson cloning. The correct cloning of the target vector was characterized by restriction digestion (FIG. 4A) and confirmed by sequencing (FIGS. 4G-4I). A PCR method for screening Lrba KO has been worked out (FIG. 4B) and will be used to genotype mice generated by the CRISPR technique. The FPs can be readily detected (FIG. 4C). A secretable luciferase gene was inserted in place of Lrba and used to show that the all-in-one Tet-inducible system in the vector functions as expected (FIG. 4D). The single guide (sgRNA) sequence for Lrba was designed using the online CRISPR Design Tool and then cloned into the pX330 vector [81]. As the sgRNA sequence spans the insertion site, the target vector does not have the sequence and will not be cleaved by the Cas9 nuclease. The sgRNA binding sequence also has a SpeI site. Thus SpeI digestion was used to identify gene mutations (FIG. 4E). The in vitro Cas9/sgRNA cleavage assay was also used to test the Lrba sgRNA (FIG. 4F). Both assays indicate that the Cas9/sgRNA is working and Lrba locus has been successfully mutated in the ES cells. Similarly, the sgRNAs for Nfkb1 and Rosa26 will be designed and cloned. Others have been successful in inserting a 3.5 kb loxP-STOP-TRE-loxP cassette and multiple functional lines have been generated using the traditional ko method [82].

The fragments for the two universal TCFP cassettes, the Hbb intron with SD and SA sequence and a loxP site, TRE-SA, mNeonGreen-2A, Aqua-2A and rtTA-2A with the P2A sequence at their C-termini have been synthesized as gBlocks and cloned. The vectors containing mRuby2, iRFP670 and STOP were ordered from Addgene. All of these fragments have been confirmed through sequencing and their functionality has been tested. With high fidelity PCR, Gibson cloning techniques [66], and the availability of all of these fragments, it is expected that the three target templates will be successfully assembled and function properly in vitro. One potential concern is that although high fidelity DNA polymerase will be used in the PCR reaction, mutations may be introduced. To avoid this problem, several clones will be picked up and sequence all of the two universal cassettes and the homologous arms. The correct clones will then be chosen for the next step.

EXAMPLE 2

Animal Model Generation and Model Functionality

1. Generation of Mouse Model Through CRISPR Technology.

The mouse model will be generated as described previously [53,83]. Briefly, the T7 promoter will be added to the Cas9 coding sequence, the sgRNAs of Nfkb1 and Rosa26 by PCR using the primer pairs (Lrba sgRNA has been synthesized) [53]. The RNAs will be synthesized by T7 RNA polymerase in vitro and purified. Then, the Cas9 mRNA (100 ng/ml), and sgRNA (50 ng/ml) and 200 ng/ml target DNA template for each target will be injected into the cytoplasm of fertilized B57BL/6 eggs. Cytoplasm injection yields the highest number of positive pups with 89% homozygous KO efficiency [84]. The genomic DNA from targeted and control mice, age 8 to 12 days, will be extracted from clipped toes and used for PCR screening: The correct 5' and 3' end targeting will be confirmed by the PCR protocol [9] using the primers from the vector and the genomic DNA sequence outside of the left or right arms (FIG. 4B). The mice that are correctly targeted as identified by PCR will be confirmed by Southern blot with the probes from mRuby2, iRFP670 and Cre genes in order to characterize the targeted Nfkb1, Lrba and Rosa26 loci, respectively as previously described [9].

2. Characterization of Mouse Model Functionality.

Dox-induced Lrba gene expression: This model has the all-in-one TetOn system. The expression of the Lrba and Nfkb1 genes can be induced by Dox and detected by flow cytometry. The triple knockin mouse aabbrtTAcreERT2+/− (a=Lrba KO, b=Nfkb1 KO) mice and C57BL/6 WT mice (6 wks of age) will be treated with or without Dox. Dox binds to the rtTA and will activate Lrba and Nfkb1 expression in the knockin mice in the presence of Dox.

Tam-induced Cre mosaic recombination: Nine genotypes of the two genes will be produced in a single Lrba Nfkb1 rtTAcreERT2+/− mouse by Tam-induced Cre mosaic recombination. It can be distinguished by flow cytometry (FIG. 1) since Cre mediated recombination is normally incomplete [9,85]. The conditions (dosing and time) of Tam treatment will be optimized to obtain roughly equal numbers of the three B cell types for each gene, as determined by flow cytometry. Mice will receive 0, 3, or 9 mg of Tam (ip injection) for 1 to 5 consecutive days. Then, on day 24, the mice will be treated with Tam (i.p.) at the optimized condition to induce partial Cre recombination, producing nine types of peripheral blood cells [86]. On days 0, 10, 17 and 31, blood from the submandibular vein will be collected and subjected to flow cytometry (FIG. 5B).

Flow cytometry: As mouse peripheral blood is limited, a no-lyse, no-wash staining flow cytometry technique will be utilized, which will use 20 µL of whole blood for each analysis [87,88]. Cells will be stained with the anti-mouse CD45-PE-Cy7 antibody (Ebioscience) to distinguish the white blood cells from the much more abundant red blood cells and the LIVE/DEAD® Yellow dye, which will keep data set sizes manageable. Live CD45 positive cells will be gated and the nine populations will be analyzed. Although there is no overlapping between the four FPs and minimal overlapping with PE-Cy7 and the Yellow dye, compensation will be carried out by using the Raji B cells stained with the Yellow dye and anti-human CD45 PE-Cy7 separately, and the Raji B cells transfected with the four individual FP expression vectors.

Apoptosis assay: Apoptosis is central to the immune system. Useful immune cells are kept alive; unwanted or harmful immune cells are eliminated by apoptosis. Deregulated apoptosis can cause diseases. The best example is the primary immunodeficiency autoimmune lymphoproliferative syndrome (ALPS) resulting from defective apoptosis [89,90]. Both LRBA and NFkB can be both anti-apoptotic and proapoptotic. Both are involved in immunodeficiency and autoimmunity. Without being limited by theory, the inventors hypothesize that Lrba and Nfkb1 genetically interact with each other to affect leukocyte survival. To test this hypothesis, flow cytometry will be carried out using Annexin V, biotin-X conjugate/R-PE/CY7 streptavidin conjugate and LIVE/DEAD® Yellow Dead Cell Stain Kit to stain the cells following a standard cytometry protocol with red cell lysis, using 100 μl of blood from each mouse older than 6 months. The nine types of cells with nine different genotypes will be gated and analyzed as standard apoptosis assay. The concentration of total white blood cells from each bleeding will be measured by single bead-enhanced cytofluorimetry [91].

It is expected that the Genebow mouse model with three knockins (aabbrtTAcreERT2+/−) will be successfully generated, since CRISPR technique has high efficiency of multiplex targeting [53,55,57,83,92-95]. However, if the mouse with the desired genotype is not generated, the inventors will mate these mice that have one or two knockins to obtain the mice with the desired genotype. CRISPR targeting may induce off-target mutations [53,96]. To detect any such potential mutations, the top 20 genome-wide off-target sites identified by the CRISPR Design tool will be amplified by PCR and sequenced. If mutations are detected, then the founders will be backcrossed with C57BL/6 mice multiple times until no mutations can be detected. It is expected that the apoptosis will be increased following the knockout of Lrba and Nfkb1 genes on a dose-dependent manner, i.e., apoptosis rate: A+++B+++ (Dox-induced overexpression of the two genes, bleeding II)<AABB<(AABb, AaBB)<(AAbb, AaBb, aaBB)<(Aabb, aaBb)<aabb<A−−−B−−− (There is no expression of the of the two genes in any cells in the mouse bleeding I & III). The prediction is based on that both Lrba and Nfkb1 are mainly anti-apoptotic [4,47,51,97,98]. They may have addictive anti-apoptotic effects and complement each another. However, the two gene appear to have contradictory functions in apoptosis. They can be pro-apoptotic [52]. In either case, a pattern should be observed from the study of the nine genotypes plus one overexpression (A+++B+++) and one complete KO (A−−−B−−−) and will design the next experiments, e.g., using MACS® Technology to isolate B or T cells to test the conditions (e.g., cell type, stimuli) under which Lrba or Nfkb1 is anti- or pro-apoptosis. This may help to demystify the paradoxical association of immunodeficiency and autoimmunity, an unsolved fundmental question.

Supplemental Disclosure 1

Genetic interaction study in the intact animal provides the most compelling means to define genotype-phenotype relationship, but it is extremely challenging in human and animal models, since the variations between individuals can interfere with a gene's contribution, which usually is small, to a phenotype. To overcome this barrier, the inventors propose that the nine genotypes of two genes are produced and respectively labeled with fluorescent proteins in a single animal (e.g., a mouse) so that they can be analyzed in a single flow cytometer tube. Phenotyping sensitivity thus can be greatly increased with the increased sample size and eliminated variations. To provide a proof of principle for this strategy, the inventors propose inserting a genotype-switching and labeling cassettes into the genomic loci of the lipopolysaccharide-responsive beige-like anchor (Lrba). The inventors will also test whether Lrba expression can be switched on and off with equal probabilities and the three phenotypes of Lrba are specifically labeled with fluorescent colors. The invention presents a revolutionary methodology to efficiently conduct genetic interaction study in animal models to understand the etiology of complex human diseases.

The inventors have developed a simple but eloquent technique to conditionally knockout a gene and label the three genotypes, wild type, heterozygous and knockout, with specific fluorescent colors, in a single mouse. This can be done by knocking a genotype-switching and labeling cassette into the genomic loci of a gene. The knockin will not interrupt the expression of the targeted gene as the gene and one fluorescent proteins (FP) linked by a porcine teschovirus-1 2A (P2A) peptide gene will be co-expressed under the same endogenous promoter. Cre recombinase-mediated cleavage and ligation of the two inverted loxP sites will invert the intervening DNA. The inversion will inactivate both the targeted gene and the FP that is co-expressed with the targeted gene, but will activate another FP. As the sequences of the loxP site and the size of the intervening DNA remain unchanged, the reaction is reversible with equal reaction rates at both directions.

The intervening DNA between two inverted loxP sites can be inverted back and forth with equal probabilities by Cre recombination, resulting in equal numbers of two plasmid molecules, in which the intervening DNA has opposite orientations, in bacteria. This will be proved by transforming competent cells with the two plasmids resulted from the Cre recombination. Equal numbers of bacterial colonies will harbor the two plasmids, respectively. The results should also be true in mouse embryonic stem (ES) cells. The frequencies of the two orientations of the intervening DNA in the genome are equal. Furthermore, the two alleles of Lrba gene are respectively labeled with two FP: green FP labels wild type (wt) allele, while red FP labels knockout (ko) allele. In other words the three genotypes of ES cells are specifically labeled with FPs: wt cells are labeled with green FP, ko cells are labeled with red FP, while heterozygous (het) cells are labeled with green FP and red FP. These cells in a mixture thus can be distinguished by flow cytometry without using traditional genotyping techniques. These results will demonstrate that Cre-mediated DNA inversion can be used to turn on and off gene expression with equal probabilities and the on/off status of gene expression can be specifically labeled with FPs. These results will provide proof of principle to develop Genebow models to conditionally produce equal frequencies of wt and ko alleles that are labeled with specific FPs, so that all the nine genotypes of two genes from a single mouse can be detected and assayed in a single flow cytometry tube. The two requirements, i.e. a large sample size and high phenotyping sensitivity required for genetic interaction study, can be fulfilled. By using the Genebow technique, genetic interaction study can be, for the first time, efficiently conducted in animal models at high resolution, critical to understanding the etiology of complex human diseases.

The mutation of the LRBA gene [99,100] causes severe autoimmune diseases, e.g., inflammatory bowel diseases [101], type 1 diabetes and rheumatoid arthritis [102,103]. The underlying molecular mechanisms of LRBA deficiency are unknown. Moreover, LRBA deficiency lacks a clear genotype-phenotype relationship (GPr) as the clinical manifestations are highly variable. This indicates complex genetic interactions, i.e., the phenotype of LRBA deficiency is dependent on the genetic interaction of LRBA with other genes. Indeed, LRBA interacts with multiple critical genes (FIGS. 7B-D) [100,104-106]. Therefore, the genetic interactions (GI) of LRBA with other critical genes must be studied to define a clear GPr to understand this complex human disease. The phenotype-based GI study in the intact animal provides the most compelling means to define GPr [107]. While a physical interaction study, based on two-hybrid, affinity capture-Western/mass spectrometry, is important, it does not link genotype to phenotype. However, GI study is extremely challenging in humans and animal models, since the variations between individuals can severely interfere with a gene's contribution to a phenotype, resulting in low phenotyping sensitivity. Consistently, the history of mouse genetics has demonstrated that "clear and consistent phenotypes are the exception rather than the rule", e.g., phenotypes cannot be detected in most gene knockouts [108]. An impractically large sample size is required to obtain statistically significant data, e.g., 500,000 subjects are required to achieve sufficient statistical power to detect non-additive effects of genetic variants [109]. To overcome this barrier, the inventors propose that the nine genotypes of two genes are produced and respectively labeled with four fluorescent proteins (FPs) in a single mouse and each cell will be studied as an individual analogous to a mouse in a traditional assay (FIG. 7A). In this manner, large numbers of cells, e.g., one mouse spleen contains ~2×106 T regulatory cells and ~2×108 splenocytes, with the nine different genotypes from a single mouse can be analyzed in a single tube with a flow cytometer, which can analyze up to 40,000 cells per second [110]. The background variations between these cells thus can be eliminated, because these cells are from the same mouse, thus have the same genetic background, epigenetic modifications and environmental inputs. With large sample size and eliminated variations, phenotyping sensitivity can be greatly increased (FIG. 7A bottom). The two requirements, i.e., a large sample size and high phenotyping sensitivity by knocking two genotype-switching and labeling cassettes (GSLC) separately into the genomic loci of two genes.

Figure 8C:
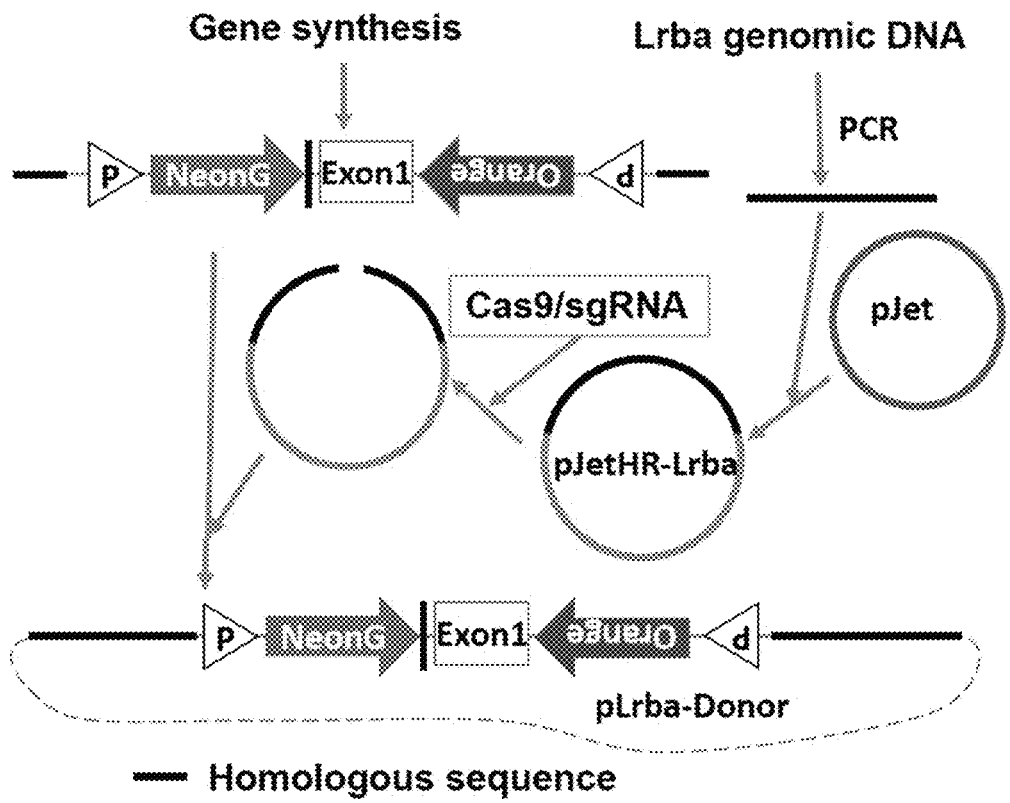

A GSLC is shown in FIG. 8B. The knockin will not interrupt Lrba expression, as Lrba and the green FP linked by a porcine teschovirus-1 2A (P2A) peptide gene will be co-expressed under the Lrba promoter. P2A is widely used to link two proteins to be co-expressed by a single promoter.15 Cre recombinase-mediated cleavage and ligation of the two inverted loxP sites will invert the intervening DNA, switching on/off between the expression of the green FP and Lrba (wild type, wt, allele) and that of red FP (knockout, ko, allele) (FIG. 8B). Therefore, ko cells will be labeled as red FP, wt cells will be labeled as green FP, and heterozygous (het) cells will be labeled as red/green FPs (FIG. 8A-C). Similarly, Nfkb1 can be labeled with two other FPs: ko (purple), het (purple/blue) and wt (blue) (FIG. 7A, FIG. 8B legend). The nine genotypes of the two genes thus can be produced and respectively labelled with four FPs (FIG. 7A). The concept of the Genebow technique, i.e., to visualize or "see" the genotypes of conditional gene knockouts, is highly innovative.

Construction of Lrba Knockin Vector.

Figure 7E:
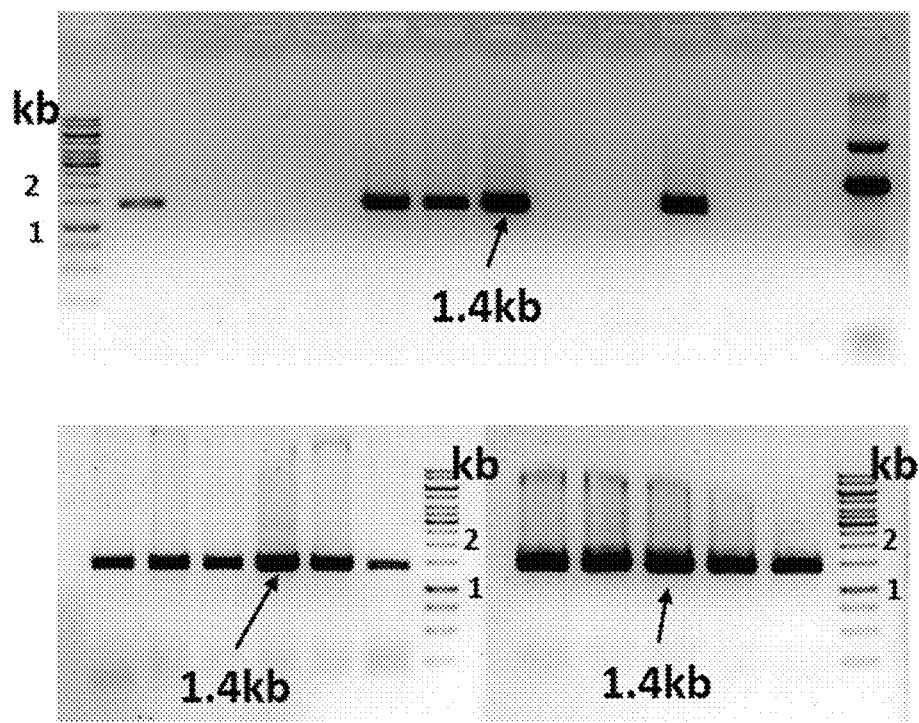

The CRISPR system causes DNA double strand break (DSB), which can be repaired by homology-directed-repair pathways. A DNA fragment flanked by two homologous sequences can be efficiently inserted into the cleavage site [114]. The inventors obtained correctly targeted mouse embryonic stem (ES) cells with high efficiency (67%) [115]. A knockin construct with short homologous arms was also tried and high knockin efficiency was obtained (FIG. 7E). Therefore, the CRISPR targeting system will be used to knock the GSLC1 into the genomic loci of Lrba [20,21]. Two vectors, i.e., a donor vector and Cas9/sgRNA vector, are required for targeting each gene. The Cas9/sgRNA vector provides Cas9 endonuclease and a target site-specific sgRNA to cleave the target site. The donor vector contains the GSLC1 flanked by two homologous fragments serves as a CRISPR repair template to mediate the knockin of the GSLC1. A protocol was established to readily construct these vectors, and the Cas9/sgRNA vector for Lrba is ready [115,118]. The cloning strategy of the donor vector is depicted in FIG. 8C. Gene synthesis will be used for easy gene assembly to facilitate the cloning [118-120]. The correct cloning of the knockin target vector will be characterized by restriction digestion and confirmed by sequencing.

Functionality of Lrba Knockin Vector.

The knockin vector contains the GSLC, which is used to switch and label the genotypes. The two functions will be tested in vitro. The Cre recombinase-mediated inversion will be tested in bacteria. Plasmid 706-Cre (Gene Bridges GmbH) will be transformed into the bacteria containing pLrba-Donor following the manufacturer's protocol, and the bacteria that harbor the two plasmids will be cultured 12-24 hours at 30° C. DNA will be extracted and re-transform competent cells. 20 colonies will be picked up and cultured for DNA isolation. Cre recombinase-mediated inversion will be examined by restriction enzyme digestion of isolated DNA (FIGS. 9A-C). It is expected that the numbers of the colonies that harbor the original and inverted intervening DNA are equal, indicating that the rates of Cre-mediated reactions at both directions are equal. The functionality of the CRISPR vectors will be validated in ES cells. The GSLC1 will be knocked into the Lrba genomic locus in ES cells as described [115]. Green FP positive clones will be picked up and screened by 5' and 3' PCR, and confirmed by Southern blot following the inventors' methods [115]. The correctly targeted ES clones will be infected with the recombinant retroviruses made from the plasmid MSCV.CreERT2.puro (Addgene) and selected by puromycin for stable clones, which will be used for Tamoxifen (TAM)-induced Cre-cleavage assay §. Gene expression will be directly detected by the expression of the fluorescent proteins by flow cytometry to detect Cremediated genotype-switching and labeling. The correct recombination and the association between the genotypes and FP colors will also be confirmed by sorting the three types of cells and conducting PCR and Western blot. Sorted cells will also be expanded and further confirmed by Southern blot [115]. It is expected that the three genotypes of Lrba will be generated and specifically labeled in ES cells with the ratios: 1 wt:2 het: 1 ko.

The TAM-inducible Cre recombination system allows optimization of the dose and time of TAM administration to have complete or near complete Cre recombination, which will be determined by flow cytometry. The condition (dosing and time) of TAM treatment that achieves balanced Cre reaction producing equal numbers of wt and ko cells as determined by flow cytometry, will be determined empirically, using 0 to 2 µM TAM for 12 to 72 hours [123,124]. Each experiment will be conducted in triplicate and repeat three times. The knockin vector may need to be modified using a CRISPR cloning technique [118] to obtain optimal genotype-switching and labeling results.

The principle of the Genebow technique is an improvement of Brainbow [111,120,125] and Cre/lox system [126], in that the Brainbow system only labels cells and traditional conditional knockout cannot "see" (visualize) a genotype. Genebow is a conditional gene knockout and genotype labeling technique.

The Genebow technique will allow researchers to efficiently conduct genetic interaction studies, for the first time, in animal models, which is critical to understanding the etiology of complex human diseases including the diseases caused by LRBA deficiency. LRBA is a critical immune regulator and plays a fundamental role in the immune system [99,100]. However, LRBA is only one example of the genes that may be investigated using the invention. For example, similar experiments with Nfkb1 can be conducted, generating the Genebow animals models for Lrba and Nfkb1 to study the genetic interaction of the two genes in animal models. LRBA and NFKB1 closely interact with each other (FIG. 7A). NFKB1, among the genes that cause autoimmunity when mutated, has the most autoimmune problems (70%) that are found in LRBA deficiency [129].

REFERENCES

1. Manolio, T. A. & Collins, F. S. Genes, environment, health, and disease: facing up to complexity. *Hum Hered* 63, 63-6 (2007).
2. Cost, G. J. Enzymatic ligation assisted by nucleases: simultaneous ligation and digestion promote the ordered assembly of DNA. *Nat Protoc* 2, 2198-202 (2007).
3. Shamloula, H. K. et al. rugose (rg), a *Drosophila* A kinase anchor protein, is required for retinal pattern formation and interacts genetically with multiple signaling pathways. *Genetics* 161, 693-710 (2002).
4. Wang, J. W. et al. Deregulated expression of LRBA facilitates cancer cell growth. *Oncogene* 23, 4089-97 (2004).
5. Yatim, A. et al. NOTCH1 nuclear interactome reveals key regulators of its transcriptional activity and oncogenic function. *Mol Cell* 48, 445-58 (2012).
6. Beck, J. A. et al. Genealogies of mouse inbred strains. *Nat Genet* 24, 23-5 (2000).
7. Rogner, U. C. & Avner, P. Congenic mice: cutting tools for complex immune disorders. *Nat Rev Immunol* 3, 243-52 (2003).
8. Livet, J. et al. Transgenic strategies for combinatorial expression of fluorescent proteins in the nervous system. *Nature* 450, 56-62 (2007).
9. Wang, J. W. et al. Influence of SHIP on the NK repertoire and allogeneic bone marrow transplantation. *Science* 295, 2094-7 (2002).
10. Wang, J. W., Howson, J., Haller, E. & Kerr, W. G. Identification of a novel lipopolysaccharide-inducible gene with key features of both A kinase anchor proteins and chs1/beige proteins. *J Immunol* 166, 4586-95 (2001).
11. Wang, J.-W., Wang, A., Li, K., Jin, S. & Lockey, R. F. CRISPR/Cas9 nuclease combined with Gibson assembly for scarless cloning into large vectors. *Biotechniques*. 2014. accepted for publication (2014).
12. Taylor-Cousar, J. L. et al. Histo-blood group gene polymorphisms as potential genetic modifiers of infection and cystic fibrosis lung disease severity. *PLoS One* 4, e4270 (2009).
13. Drumm, M. L. et al. Genetic modifiers of lung disease in cystic fibrosis. *N Engl J Med* 353, 1443-53 (2005).
14. Fuchs, H. et al. Mouse phenotyping. *Methods* 53, 120-35.
15. Belizario, J. E. The humankind genome: from genetic diversity to the origin of human diseases. *Genome* 56, 705-16 (2013).
16. Arnedo, J. et al. Uncovering the Hidden Risk Architecture of the Schizophrenias: Confirmation in Three Independent Genome-Wide Association Studies. *Am J Psychiatry*.
17. Podjasek, J. C. & Abraham, R. S. Autoimmune cytopenias in common variable immunodeficiency. *Front Immunol* 3, 189 (2012).
18. Wright, F. A. et al. Genome-wide association and linkage identify modifier loci of lung disease severity in cystic fibrosis at 11p13 and 20q13.2. *Nat Genet* 43, 539-46 (2011).
19. Doetschman, T. Influence of genetic background on genetically engineered mouse phenotypes. *Methods Mol Biol* 530, 423-33 (2009).
20. Kurtz, T. W. Genome-wide association studies will unlock the genetic basis of hypertension: con side of the argument. *Hypertension* 56, 1021-5 (2010).
21. Ermann, J. & Glimcher, L. H. After GWAS: mice to the rescue? *Curr Opin Immunol* 24, 564-70 (2012).
22. Kado, S. et al. Intestinal microflora are necessary for development of spontaneous adenocarcinoma of the large intestine in T-cell receptor beta chain and p53 double-knockout mice. *Cancer Res* 61, 2395-8 (2001).
23. Franklin, C. L. Microbial considerations in genetically engineered mouse research. *ILAR J* 47, 141-55 (2006).
24. Treuting, P. M., Clifford, C. B., Sellers, R. S. & Brayton, C. F. Of mice and microflora: considerations for genetically engineered mice. *Vet Pathol* 49, 44-63 (2012).
25. Watkins-Chow, D. E. & Pavan, W. J. Genomic copy number and expression variation within the C57BL/6J inbred mouse strain. *Genome Res* 18, 60-6 (2008).
26. Bryant, C. D. et al. Behavioral differences among C57BL/6 substrains: implications for transgenic and knockout studies. *J Neurogenet* 22, 315-31 (2008).
27. Saeed, S. et al. Epigenetic programming of monocyte-to-macrophage differentiation and trained innate immunity. *Science* 345, 1251086 (2014).
28. Stevens, J. C., Banks, G. T., Festing, M. F. & Fisher, E. M. Quiet mutations in inbred strains of mice. *Trends Mol Med* 13, 512-9 (2007).
29. Eisener-Dorman, A. F., Lawrence, D. A. & Bolivar, V. J. Cautionary insights on knockout mouse studies: the gene or not the gene? *Brain Behav Immun* 23, 318-24 (2009).
30. Ridgway, W. M. A new tool for dissecting genetic control of type 1 diabetes. *Diabetes* 63, 56-8 (2014).
31. Ridgway, W. M., Healy, B., Smink, L. J., Rainbow, D. & Wicker, L. S. New tools for defining the 'genetic background' of inbred mouse strains. *Nat Immunol* 8, 669-73 (2007).
32. Keane, T. M. et al. Mouse genomic variation and its effect on phenotypes and gene regulation. *Nature* 477, 289-94 (2011).
33. Sundberg, J. P., Roopenian, D. C., Liu, E. T. & Schofield, P. N. The Cinderella effect: searching for the best fit between mouse models and human diseases. *J Invest Dermatol* 133, 2509-13 (2013).
34. Greve, B. et al. High-grade loss of leukocytes and hematopoietic progenitor cells caused by erythrocyte-lysing procedures for flow cytometric analyses. *J Hematother Stem Cell Res* 12, 321-30 (2003).
35. Einwallner, E. et al. Lysis matters: red cell lysis with FACS Lyse affects the flow cytometric enumeration of circulating leukemic blasts. *J Immunol Methods* 390, 127-32 (2013).
36. Greve, B., Beller, C., Cassens, U., Sibrowski, W. & Gohde, W. The impact of erythrocyte lysing procedures 36. on the recovery of hematopoietic progenitor cells in flow cytometric analysis. *Stem Cells* 24, 793-9 (2006).
37. Frazer, K. A. et al. A sequence-based variation map of 8.27 million SNPs in inbred mouse strains. *Nature* 448, 1050-3 (2007).
38. Yang, H. et al. Subspecific origin and haplotype diversity in the laboratory mouse. *Nat Genet* 43, 648-55 (2011).
39. Chalfin, L. et al. Mapping ecologically relevant social behaviours by gene knockout in wild mice. *Nat Commun* 5, 4569 (2014).
40. Linder, C. C. Genetic variables that influence phenotype. *ILAR J* 47, 132-40 (2006).
41. Niu, Y. et al. Generation of gene-modified cynomolgus monkey via Cas9/RNA-mediated gene targeting in one-cell embryos. *Cell* 156, 836-43.
42. Cai, D., Cohen, K. B., Luo, T., Lichtman, J. W. & Sanes, J. R. Improved tools for the Brainbow toolbox. *Nat Methods* 10, 540-7 (2013).
43. Espinosa, J. S., Tea, J. S. & Luo, L. Mosaic analysis with double markers (MADM) in mice. *Cold Spring Harb Protoc* 2014, 182-9 (2014).
44. Zong, H., Espinosa, J. S., Su, H. H., Muzumdar, M. D. & Luo, L. Mosaic analysis with double markers in mice. *Cell* 121, 479-92 (2005).
45. Loulier, K. et al. Multiplex cell and lineage tracking with combinatorial labels. *Neuron* 81, 505-20 (2014).
46. Wang, J.-W. & Lockey, R. F. Lipopolysaccharide-responsive beige-like anchor (LRBA), a novel regulator of human immune disorders. *Austin Journal of Clinical Immunology* 1, 9 (2014).
47. Lopez-Herrera, G. et al. Deleterious mutations in LRBA are associated with a syndrome of immune deficiency and autoimmunity. *Am J Hum Genet* 90, 986-1001 (2012).
48. Burns, S. O. et al. LRBA gene deletion in a patient presenting with autoimmunity without hypogammaglobulinemia. *J Allergy Clin Immunol* 130, 1428-32 (2012).
49. Alangari, A. et al. LPS-responsive beige-like anchor (LRBA) gene mutation in a family with inflammatory bowel disease and combined immunodeficiency. *J Allergy Clin Immunol* 130, 481-8 e2 (2012).
50. Wang, J.-W. et al. LRBA Causes Immunodeficiency and Autoimmunity By Deregulating NFkB-Mediated Multiple Immune Effectors Critical For B Cell Activation. *Journal of Allergy and Clinical Immunology* 133, AB251-AB251 (2014).
51. Baltimore, D. NF-kappaB is 25. *Nat Immunol* 12, 683-5 (2011).
52. Hayden, M. S. & Ghosh, S. NF-kappaB, the first quarter-century: remarkable progress and outstanding questions. *Genes Dev* 26, 203-34 (2012).
53. Yang, H. et al. One-step generation of mice carrying reporter and conditional alleles by CRISPR/Cas-mediated genome engineering. *Cell* 154, 1370-9 (2013).
54. Zhou, J. et al. Dual sgRNAs facilitate CRISPR/Cas9-mediated mouse genome targeting. *FEBS J* 281, 1717-25 (2014).
55. Wang, H. et al. One-step generation of mice carrying mutations in multiple genes by CRISPR/Cas-mediated genome engineering. *Cell* 153, 910-8.
56. Yang, H. et al. One-step generation of mice carrying reporter and conditional alleles by CRISPR/Cas-mediated genome engineering. *Cell* 154, 1370-9.
57. Fujii, W., Kawasaki, K., Sugiura, K. & Naito, K. Efficient generation of large-scale genome-modified mice using gRNA and CAS9 endonuclease. *Nucleic Acids Res* 41, e187.
58. Jinek, M. et al. A programmable dual-RNA-guided DNA endonuclease in adaptive bacterial immunity. *Science* 337, 816-21 (2012).
59. Harrison, M. M., Jenkins, B. V., O'Connor-Giles, K. M. & Wildonger, J. A CRISPR view of development. *Genes Dev* 28, 1859-1872 (2014).
60. Yasue, A. et al. Highly efficient targeted mutagenesis in one-cell mouse embryos mediated by the TALEN and CRISPR/Cas systems. *Sci Rep* 4, 5705.
61. Bottcher, R. et al. Efficient chromosomal gene modification with CRISPR/cas9 and PCR-based homologous recombination donors in cultured *Drosophila* cells. *Nucleic Acids Res* 42, e89 (2014).
62. Gratz, S. J. et al. Highly specific and efficient CRISPR/Cas9-catalyzed homology-directed repair in *Drosophila*. *Genetics* 196, 961-71 (2014).
63. Donoho, G., Jasin, M. & Berg, P. Analysis of gene targeting and intrachromosomal homologous recombination stimulated by genomic double-strand breaks in mouse embryonic stem cells. *Mol Cell Biol* 18, 4070-8 (1998).
64. Dean, K. M. & Palmer, A. E. Advances in fluorescence labeling strategies for dynamic cellular imaging. *Nat Chem Biol* 10, 512-23 (2014).
65. Wan, Y. Y. & Flavell, R. A. Identifying Foxp3-expressing suppressor T cells with a bicistronic reporter. *Proc Natl Acad Sci USA* 102, 5126-31 (2005).
66. Gibson, D. G. et al. Enzymatic assembly of DNA molecules up to several hundred kilobases. *Nat Methods* 6, 343-5 (2009).
67. Gibson, D. G., Smith, H. O., Hutchison, C. A., 3rd, Venter, J. C. & Merryman, C. Chemical synthesis of the mouse mitochondrial genome. *Nat Methods* 7, 901-3.
68. Niwa, H., Yamamura, K. & Miyazaki, J. EFFICIENT SELECTION FOR HIGH-EXPRESSION TRANSFECTANTS WITH A NOVEL EUKARYOTIC VECTOR. *Gene* 108, 193-199 (1991).
69. Shcherbakova, D. M. & Verkhusha, V. V. Near-infrared fluorescent proteins for multicolor in vivo imaging. *Nat Methods* 10, 751-4 (2013).
70. Erard, M. et al. Minimum set of mutations needed to optimize cyan fluorescent proteins for live cell imaging. *Mol Biosyst* 9, 258-67 (2013).
71. Sauer, B. Manipulation of transgenes by site-specific recombination: use of Cre recombinase. *Methods Enzymol* 225, 890-900 (1993).
72. Zhou, X., Vink, M., Klaver, B., Berkhout, B. & Das, A. T. Optimization of the Tet-On system for regulated gene expression through viral evolution. *Gene Ther* 13, 1382-90 (2006).
73. Loew, R., Heinz, N., Hampf, M., Bujard, H. & Gossen, M. Improved Tet-responsive promoters with minimized background expression. *BMC Biotechnol* 10, 81 (2010).
74. Kistner, A. et al. Doxycycline-mediated quantitative and tissue-specific control of gene expression in transgenic mice. *Proc Natl Acad Sci USA* 93, 10933-8 (1996).
75. Kim, J. H. et al. High cleavage efficiency of a 2A peptide derived from porcine teschovirus-1 in human cell lines, zebrafish and mice. *PLoS One* 6, e18556 (2011).
76. Ewald, D. et al. Time-sensitive reversal of hyperplasia in transgenic mice expressing SV40 T antigen. *Science* 273, 1384-6 (1996).
77. Aghajani, K., Keerthivasan, S., Yu, Y. & Gounari, F. Generation of CD4CreER(T(2)) transgenic mice to study development of peripheral CD4-T-cells. *Genesis* 50, 908-13.

78. Metzger, D., Clifford, J., Chiba, H. & Chambon, P. Conditional site-specific recombination in mammalian cells using a ligand-dependent chimeric Cre recombinase. *Proc Natl Acad Sci USA* 92, 6991-5 (1995).
79. Feil, S., Valtcheva, N. & Feil, R. Inducible Cre mice. *Methods Mol Biol* 530, 343-63 (2009).
80. McLaughlin, M. E. et al. The Nf2 tumor suppressor regulates cell-cell adhesion during tissue fusion. *Proc Natl Acad Sci USA* 104, 3261-6 (2007).
81. Cong, L. et al. Multiplex genome engineering using CRISPR/Cas systems. *Science* 339, 819-23.
82. Tanaka, K. F. et al. Flexible Accelerated STOP Tetracycline Operator-knockin (FAST): a versatile and efficient new gene modulating system. *Biol Psychiatry* 67, 770-3 (2010).
83. Yang, H., Wang, H. & Jaenisch, R. Generating genetically modified mice using CRISPR/Cas-mediated genome engineering. *Nat Protoc* 9, 1956-68 (2014).
84. Horii, T. et al. Validation of microinjection methods for generating knockout mice by CRISPR/Cas-mediated genome engineering. *Sci Rep* 4, 4513.
85. Leneuve, P. et al. Cre-mediated germline mosaicism: a new transgenic mouse for the selective removal of residual markers from tri-lox conditional alleles. *Nucleic Acids Res* 31, e21 (2003).
86. Hayashi, S. & McMahon, A. P. Efficient recombination in diverse tissues by a tamoxifen-inducible form of Cre: a tool for temporally regulated gene activation/inactivation in the mouse. *Dev Biol* 244, 305-18 (2002).
87. Weaver, J. L., Broud, D. D., McKinnon, K. & Germolec, D. R. Serial phenotypic analysis of mouse peripheral blood leukocytes. *Toxicol Mech Methods* 12, 95-118 (2002).
88. Weaver, J. L., McKinnon, K. & Germolec, D. R. Phenotypic analysis using very small volumes of blood. *Curr Protoc Cytom* Chapter 6, Unit 6 30 (2010).
89. Todoric, K., Koontz, J. B., Mattox, D. & Tarrant, T. K. Autoimmunity in immunodeficiency. *Curr Allergy Asthma Rep* 13, 361-70 (2013).
90. Mackay, I. R., Leskovsek, N. V. & Rose, N. R. The odd couple: a fresh look at autoimmunity and immunodeficiency. *J Autoimmun* 35, 199-205 (2010).
91. Montes, M., Jaensson, E. A., Orozco, A. F., Lewis, D. E. & Corry, D. B. A general method for bead-enhanced quantitation by flow cytometry. *J Immunol Methods* 317, 45-55 (2006).
92. Cong, L. et al. Multiplex genome engineering using CRISPR/Cas systems. *Science* 339, 819-23 (2013).
93. Kabadi, A. M., Ousterout, D. G., Hilton, I. B. & Gersbach, C. A. Multiplex CRISPR/Cas9-based genome engineering from a single lentiviral vector. *Nucleic Acids Res* (2014).
94. Ma, S. et al. CRISPR/Cas9 mediated multiplex genome editing and heritable mutagenesis of BmKu70 in *Bombyx mori*. *Sci Rep* 4, 4489 (2014).
95. Sakuma, T., Nishikawa, A., Kume, S., Chayama, K. & Yamamoto, T. Multiplex genome engineering in human cells using all-in-one CRISPR/Cas9 vector system. *Sci Rep* 4, 5400 (2014).
96. Fu, Y. et al. High-frequency off-target mutagenesis induced by CRISPR-Cas nucleases in human cells. *Nat Biotechnol* 31, 822-6 (2013).
97. Andres, S. A., Brock, G. N. & Wittliff, J. L. Interrogating differences in expression of targeted gene sets to predict breast cancer outcome. *BMC Cancer* 13, 326 (2013).
98. Beg, A. A. & Baltimore, D. An essential role for NF-kappaB in preventing TNF-alpha-induced cell death. *Science* 274, 782-4 (1996).
99. Wang, J. W., Howson, J., Haller, E. & Kerr, W. G. Identification of a novel lipopolysaccharide-inducible gene with key features of both A kinase anchor proteins and chs1/beige proteins. *J Immunol* 166, 4586-95 (2001).
100. Wang, J. W., Gamsby, J. J., Highfill, S. L., Mora, L. B., Bloom, G. C., Yeatman, T. J., Pan, T. C., Ramne, A. L., Chodosh, L. A., Cress, W. D., Chen, J. & Kerr, W. G. Deregulated expression of LRBA facilitates cancer cell growth. *Oncogene* 23, 4089-97 (2004).
101. Serwas, N. K., Kansu, A., Santos-Valente, E., Kuloglu, Z., Demir, A., Yaman, A., Yaneth Gamez Diaz, L., Artan, R., Sayar, E., Ensari, A., Grimbacher, B. & Bortug, K. Atypical Manifestation of LRBA Deficiency with Predominant IBD-like Phenotype. *Inflamm Bowel Dis* 21, 40-7 (2015).
102. Wang, J.-W. & Lockey, R. F. Lipopolysaccharide-responsive beige-like anchor (LRBA), a novel regulator of human immune disorders. *Austin Journal of Clinical Immunology* 1, 9 (2014).
103. Charbonnier, L. M., Janssen, E., Chou, J., Ohsumi, T. K., Keles, S., Hsu, J. T., Massaad, M. J., Garcia-Lloret, M., Hanna-Wakim, R., Dbaibo, G., Alangari, A. A., Alsultan, A., Al-Zahrani, D., Geha, R. S. & Chatila, T. A. Regulatory T-cell deficiency and immune dysregulation, polyendocrinopathy, enteropathy, X-linked-like disorder caused by loss-of-function mutations in LRBA. *J Allergy Clin Immunol* 135, 217-27 (2015).
104. Schreiber, S. L., Preiss, A., Nagel, A. C., Wech, I. & Maier, D. Genetic screen for modifiers of the rough eye phenotype resulting from overexpression of the Notch antagonist hairless in *Drosophila*. *Genesis* 33, 141-52. (2002).
105. Shamloula, H. K., Mbogho, M. P., Pimentel, A. C., Chrzanowska-Lightowlers, Z. M., Hyatt, V., Okano, H. & Venkatesh, T. R. rugose (rg), a *Drosophila* A kinase anchor protein, is required for retinal pattern formation and interacts genetically with multiple signaling pathways. *Genetics* 161, 693-710 (2002).
106. de Souza, N., Vallier, L. G., Fares, H. & Greenwald, I. SEL-2, the *C. elegans* neurobeachin/LRBA homolog, is a negative regulator of lin-12/Notch activity and affects endosomal traffic in polarized epithelial cells. *Development* 134, 691-702 (2007).
107. Ramsdell, F. & Ziegler, S. F. FOXP3 and scurfy: how it all began. *Nat Rev Immunol* 14, 343-9 (2014).
108. Pearson, H. Surviving a knockout blow. *Nature* 415, 8-9 (2002).
109. Zuk, O., Hechter, E., Sunyaev, S. R. & Lander, E. S. The mystery of missing heritability: Genetic interactions create phantom heritability. *Proc Natl Acad Sci USA* 109, 1193-8 (2012).
110. cytometer, L.f. Flow cytometer can analyze up to 40,000 cells per second flow.ucsf.edu/selfanalysis-bd-lsriifortessa (2015).
111. Cai, D., Cohen, K. B., Luo, T., Lichtman, J. W. & Sanes, J. R. Improved tools for the Brainbow toolbox. *Nat Methods* 10, 540-7 (2013).
112. Boston-University-and-Boston-Medical-Center. Sample Size Calculations. bu.edu/orccommittees/iacuc/policies-and-guidelines/sample-size-calculations/.
113. Kim, J. H., Lee, S. R., Li, L. H., Park, H. J., Park, J. H., Lee, K. Y., Kim, M. K., Shin, B. A. & Choi, S. Y. High cleavage efficiency of a 2A peptide derived from porcine teschovirus-1 in human cell lines, zebrafish and mice. *PLoS One* 6, e18556 (2011).
114. Donoho, G., Jasin, M. & Berg, P. Analysis of gene targeting and intrachromosomal homologous recombination stimulated by genomic double-strand breaks in mouse embryonic stem cells. *Mol Cell Biol* 18, 4070-8 (1998).
115. Wang, B., Li, K., Wang, A., Reiser, M., Saunders, T. L., Lockey, R. F. & Wang, J. W. Highly efficient CRISPR/HDR-mediated knockin in mouse embryonic stem cells and zygotes. *BioTechniques*. 59, 201-208 (2015).
116. Yang, H., Wang, H., Shivalila, C. S., Cheng, A. W., Shi, L. & Jaenisch, R. One-step generation of mice carrying reporter and conditional alleles by CRISPR/Cas-mediated genome engineering. *Cell* 154, 1370-9.
117. Wang, H., Yang, H., Shivalila, C. S., Dawlaty, M. M., Cheng, A. W., Zhang, F. & Jaenisch, R. One-step generation of mice carrying mutations in multiple genes by CRISPR/Cas-mediated genome engineering. *Cell* 153, 910-8.
118. Wang, J. W., Wang, A., Li, K., Wang, B., Jin, S., Reiser, M. & Lockey, R. F. CRISPR/Cas9 nuclease cleavage combined with Gibson assembly for seamless cloning. *BioTechniques* 58, 161-70 (2015).
119. IDTDNA. gBlocks® Gene Fragments Protocol: Gibson Assembly® Method. idtdna.com/pages/docs/default-source/user-guides-and-protocols/gibsonassembly.pdf?sfvrsn=12 (2012).
120. Loulier, K., Barry, R., Mahou, P., Le Franc, Y., Supatto, W., Matho, K. S., Ieng, S., Fouquet, S., Dupin, E., Benosman, R., Chedotal, A., Beaurepaire, E., Morin, X. & Livet, J. Multiplex cell and lineage tracking with combinatorial labels. *Neuron* 81, 505-20 (2014).
121. Dean, K. M. & Palmer, A. E. Advances in fluorescence labeling strategies for dynamic cellular imaging. *Nat Chem Biol* 10, 512-23 (2014).
122. Wan, Y. Y. & Flavell, R. A. Identifying Foxp3-expressing suppressor T cells with a bicistronic reporter. *Proc Natl Acad Sci USA* 102, 5126-31 (2005).
123. Chambers, I., Silva, J., Colby, D., Nichols, J., Nijmeijer, B., Robertson, M., Vrana, J., Jones, K., Grotewold, L. & Smith, A. Nanog safeguards pluripotency and mediates germline development. *Nature* 450, 1230-4 (2007).
124. Endoh, M., Endo, T. A., Endoh, T., Fujimura, Y., Ohara, O., Toyoda, T., Otte, A. P., Okano, M., Brockdorff, N., Vidal, M. & Koseki, H. Polycomb group proteins Ring1A/B are functionally linked to the core transcriptional regulatory circuitry to maintain ES cell identity. *Development* 135, 1513-24 (2008).
125. Livet, J., Weissman, T. A., Kang, H., Draft, R. W., Lu, J., Bennis, R. A., Sanes, J. R. & Lichtman, J. W. Transgenic strategies for combinatorial expression of fluorescent proteins in the nervous system. *Nature* 450, 56-62 (2007).
126. Kratochwil, C. F. & Rijli, F. M. The Cre/Lox system to assess the development of the mouse brain. *Methods Mol Biol* 1082, 295-313 (2014).
127. Wang, J. W., Howson, J. M., Ghansah, T., Desponts, C., Ninos, J. M., May, S. L., Nguyen, K. H., Toyama-Sorimachi, N. & Kerr, W. G. Influence of SHIP on the NK repertoire and allogeneic bone marrow transplantation. *Science* 295, 2094-7 (2002).
128. van de Ven, A. A. & Warnatz, K. The autoimmune conundrum in common variable immunodeficiency disorders. *Curr Opin Allergy Clin Immunol* 15, 514-24 (2015).
129. Wang, J. W., Qi, Y. P., Huang, Y. X. & Li, S. D. Nucleotide sequence of a 1446 base pair SalI fragment and structure of a novel early gene of *Leucania separata* nuclear polyhedrosis virus. *Arch Virol* 140, 2283-91 (1995).
130. Kerr, W. G. & Wang, J.-W. LPS-responsive chs1/beige-like anchor gene and therapeutic applications thereof. U.S. Pat. No. 7,704,963 (2010).
131. Reiser, M. A., Li, K., Lockey, R. F. & Wang, J. W. Lipopolysaccharide Responsive Beige-Like Anchor Subcellular Localization Involving in Vesicle Trafficking Responsive to Lipopolysaccharide. *Austin Journal of Clinical Immunology* 1, 8 (2014).
132. Wang, J.-W., Wang, A., Li, K., Jin, S. & Lockey, R. F. CRISPR/Cas9 nuclease combined with Gibson assembly for seamless cloning into large vectors. *Biotechniques*. (2015).
133. Tu, Z., Ninos, J. M., Ma, Z., Wang, J. W., Lemos, M. P., Desponts, C., Ghansah, T., Howson, J. M. & Kerr, W. G. Embryonic and hematopoietic stem cells express a novel SH2-containing inositol 5'-phosphatase isoform that partners with the Grb2 adapter protein. *Blood* 98, 2028-38 (2001).

Supplemental Disclosure 2

Mutation of the LRBA gene causes primary immunodeficiency and severe autoimmune diseases, including several human common diseases such as inflammatory bowel diseases (IBD), type 1 diabetes, and rheumatoid arthritis. The molecular mechanism of how LRBA deficiency causes such a wide spectrum of diseases is unclear. Accordingly, there is no causal treatment available for LRBA deficiency. Tregs are indispensable for controlling various autoimmune diseases. LRBA regulates two important Treg regulators, and Treg is defective in some patients. Thus, it is hypothesized that LRBA is required for the development and function of Treg, and that deregulated Treg plays a major role in causing the wide spectrum of autoimmune manifestations. However, LRBA deficiency lacks a clear genotype-phenotype relationship (GPr) as the manifestations are highly variable, indicating complex genetic interactions (GI). In other words, the phenotype of LRBA deficiency is modified by other genes. In this sense, LRBA deficiency is a polygenic disease, and the genetic interactions of LRBA with other critical genes must be studied to define a clear GPr. The phenotype-based GI study in the intact animal provides the most compelling means to define GPr, but it is extremely challenging in humans and animal models, since the variations from genetic background, epigenetic modifications and environmental factors can interfere with or mask a gene's contribution to a phenotype, resulting in low phenotyping sensitivity. An impractically large sample size and highly sensitive phenotyping are required to obtain statistically significant data.

To overcome this barrier, the inventors propose studying each cell as an individual analogous to a mouse in a traditional assay and to label each genotype with a specific, distinct label (e.g., color), so that large number of cells (up to several million) with nine different genotypes in a single animal can be analyzed in a single flow cytometry tube. In this manner, the background variation between cells should be eliminated because the cells from the same mouse have the same genetic background, epigenetic modifications and environmental input. Phenotyping sensitivity thus can be greatly increased with the greatly increased sample size and eliminated variation. To test the hypothesis, the inventors will develop a mouse model, named "Genebow", by using the Clustered Regularly Interspaced Short Palindromic Repeats (CRISPR) cloning and mouse model generation techniques. The Genebow model will be used to determine how the genetic interaction of Lrba and Nfkb1 regulates the development and function of Treg. This will demonstrate that GI study, for the first time, can be efficiently conducted in animal models at high resolution, and provide high resolution data to determine whether LRBA plays, modified by NFKB1, a critical role in regulating Tregs to suppress autoimmunity, and to provide deep insight into how LRBA deficiency causes such a wide spectrum of highly variable clinical manifestations. It will also shed light on the etiology of these human common diseases including some top 10 deadliest diseases that are associated with LRBA deficiency.

The study of genetic interaction plays a key role in defining GPr in complex human diseases, but it is extremely challenging in humans and mice, because an impractically large sample size and highly sensitive phenotyping are often required to obtain statistically significant data due to variations between individuals. A variation-free technique which can fulfill the two requirements, i.e., a large sample size and high phenotyping sensitivity, for genetic interaction study will be developed, so that genetic interaction study can be efficiently conducted in animal models for the first time. As an exemplification, this technique can be used to determine how the genetic interaction of two critical immune genes in suppressing autoimmunity at high resolution, and such high resolution results may provide deep insight into the etiology of these complex human autoimmune diseases that are associated with LRBA deficiency.

The mutation of the LRBA gene causes primary immunodeficiency and a myriad of autoimmune problems.[1] The molecular and cellular mechanisms of how LRBA deficiency causes such a wide spectrum of highly variable clinical manifestations are unknown, and thus there is no causal treatment available for LRBA deficiency. LRBA regulates two important regulators of Tregs, the cytotoxic T lymphocyte-associated antigen 4 (CTLA-4) and programmed death 1 (PD-1). LRBA deficiency also causes the immune dysregulation, polyendocrinopathy, enteropathy, X-linked (IPEX)-like syndrome.2 IPEX is caused by deficiency of Tregs. Tregs are indispensable for controlling various autoimmune diseases. The inventors thus hypothesized that LRBA is required for the development and function of Tregs, and that defective Tregs play a major role in LRBA deficiency. A goal is to delineate the molecular mechanisms of LRBA's role in the regulation of Tregs. However, LRBA deficiency lacks a clear GPr as the clinical manifestations are highly variable. This indicates complex genetic interactions (GI), i.e., the phenotype of LRBA deficiency is dependent on the genetic interaction of LRBA with other genes, e.g., NFKB1. In this sense, LRBA deficiency is a polygenic disease, and the genetic interactions of LRBA with other critical genes must be studied to define a clear GPr to understand this complex human disease.

Figure 10:
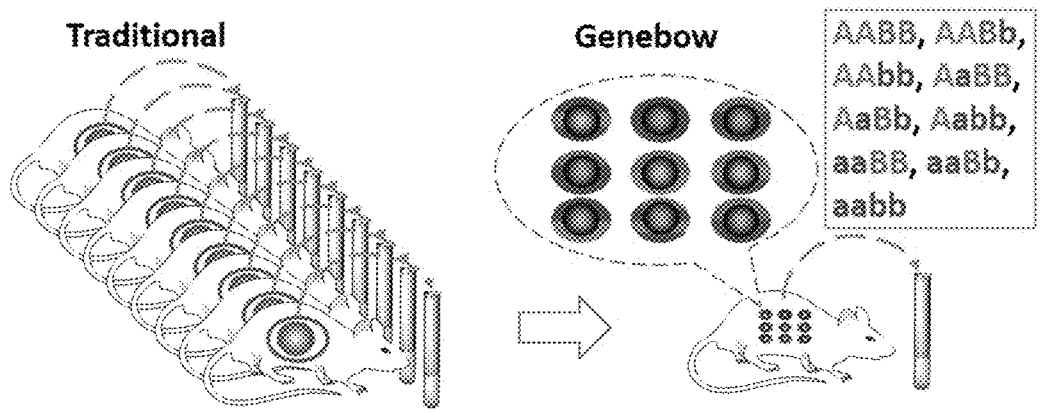
FIG. 10. Comparison of Genebow and traditional method. Traditionally, cells from each mouse (genotype) have to be analyzed separately, because if mixed, they cannot be distinguished. In contrast, Genebow can distinguish each genotype in a mixture. Consequently, e.g., to quantitate Tregs of different genotypes, the traditional method usually requires at least 27 mice and 27 tubes, while the Genebow requires only one mouse and one tube. More importantly, with greatly increased sample size and eliminated variations, the phenotyping sensitivity can be greatly increased. Nine genotypes are color-labeled. A=Lrba, B=Nfkb1, wild type: uppercase, knockout: lowercase.
Figure 13A:
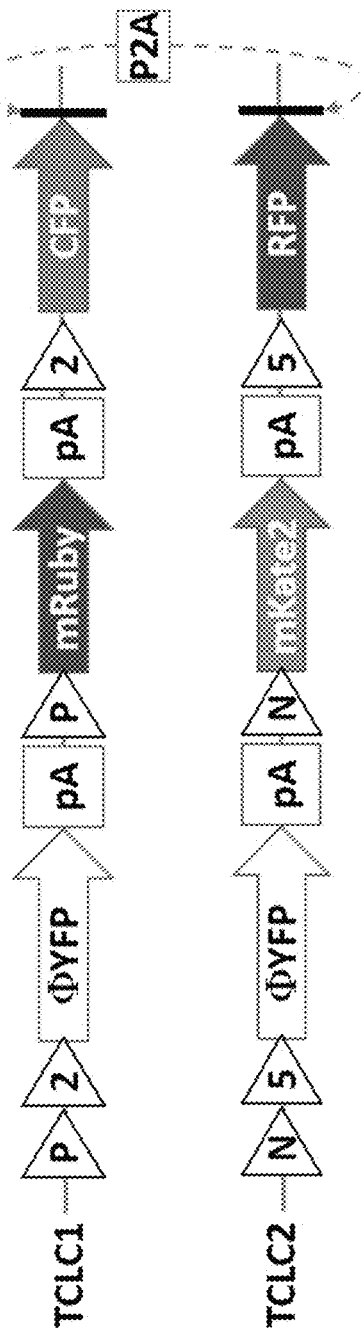

However, GI study is extremely challenging in humans and mice since that variations from genetic background, epigenetic modifications and environmental factors can interfere with or mask a gene's contribution, usually small, to a phenotype, greatly reducing the phenotyping sensitivity. Consistently, most mouse gene knockouts do not have a detectable phenotype. An impractically large sample size and highly sensitive phenotyping are required to obtain statistically significant data. For example, 500,000 subjects might be necessary to achieve sufficient statistical power to detect nonadditive effects of genetic variants.[3] To fulfil the two requirements, the inventors propose to study each cell as an individual analogous to a mouse in a traditional assay, so that large numbers of cells (~2×106 Tregs/spleen) in a single animal (e.g., a single mouse) can be analyzed in a single flow cytometry tube with greatly increased phenotyping sensitivity as a result of eliminated variations (FIG. 10, FIG. 13C). To this end, the nine genotypes of two genes will be generated and respectively labelled with four fluorescent reporters (FRs) (FIG. 13A) in a single mouse, so that the phenotypes of all genotypes of the two genes can be studied by flow cytometry in a single tube. As indicated above, this variation-free phenotyping technique was named "Genebow". LRBA and NFKB1 are closely related, e.g., among the genes that cause autoimmunity when mutated, NFKB1 has the most autoimmune problems that are found in LRBA deficiency. To test the inventors' hypothesis, a Genebow mouse model will be generated for the two genes to study their genetic interaction.

The first objective is to generate a Genebow mouse model in which Lrba and Nfkb1 expression can be turned on/off in a spatiotemporal and trackable manner. By using the CRISPR cloning and mouse model generation techniques, two transcription control and labeling cassettes (TCLC) will be separately inserted into the genomic loci of Lrba and Nfkb1. The second objective is to determine how the genetic interaction of Lrba and Nfkb1 regulates the development and function of Tregs. Reduced cell number and suppressive function of Tregs are two causes of the autoantibody overproduction. Autoantibodies cause autoimmunity in many autoimmune diseases. The working hypothesis is that deregulation of Lrba and Nfkb1 genetic interaction impairs the development and function of Tregs, and results in reduced cell number and ability to suppress autoimmunity.

If successful, it will demonstrate that a genetic interaction study of two genes, for the first time, can be efficiently conducted in animal models at high resolution, and provide high resolution data to determine whether LRBA plays, modified by NFKB1, a critical role in regulating Tregs to suppress autoimmunity, and to provide deep insight into how LRBA deficiency causes such a wide spectrum of highly variable clinical manifestations. It will also shed light on the etiology of these human common diseases, including some top 10 deadliest diseases, that are associated with LRBA deficiency.

Mutation of LRBA causes primary immunodeficiency (PID) and autoimmune diseases including IPEX-like syndrome,[2] IBD,[8] autoimmune lymphoproliferative syndrome (ALPS),[9] rheumatoid arthritis,[2,10] autoimmune hemolytic anemia (AHA), immune thrombocytopenia (ITP), and endocrinopathies (type 1 diabetes, hepatitis, growth hormone deficiency and hypothyroidism).[1,11] The clinical presentations of LRBA deficiency are highly variable.[9,12] Some patients have early onset PID, while others initially present with autoimmunity without PID.[8] The molecular mechanism of how LRBA deficiency causes such a wide spectrum of highly variable manifestations is unclear. Thus, there is no causal treatment available for LRBA deficiency. LRBA deficiency decreases CTLA-4[13] but increases PD-1.[2] CTLA-4 is required for the suppressive function of Tregs, while PD-1 is a negative regulator of Tregs. Accordingly, Treg is reduced in 16 out of 22 LRBA-deficient patients.[1] A significant number of IPEX-like syndromes might result from LRBA deficiency.[14] Treg is indispensable for controlling autoimmune diseases as demonstrated by the severity and intensity of autoimmune disease in IPEX patients and in scurfy mice. However, it is unknown whether the defective Tregs causes the autoimmune diseases in LRBA deficiency, because their suppressive ability has not been studied in vivo. It is also unknown whether LRBA deficiency directly impairs Tregs, since Tregs have only been studied in the context of all cells with LRBA mutation. In this proposal, we will test our hypothesis that LRBA is required for the development and function of Treg, and that deregulated Tregs play a major role in autoimmunity by transferring Genebow cells into an autoimmune diabetic mouse model. Furthermore, LRBA deficiency lacks a clear GPr as the clinical manifestations are highly variable, indicating complex GI. In other words, the phenotype is dependent on the genetic interaction of LRBA with other genes. Indeed, LRBA closely interacts with NFkB and other critical genes (FIGS. 11A-E).[15-18] In this sense, the LRBA deficiency is a polygenic disease, and the genetic interactions of LRBA with other critical genes must be studied to define a clear GPr.

Mouse Models.

Figure 13B:
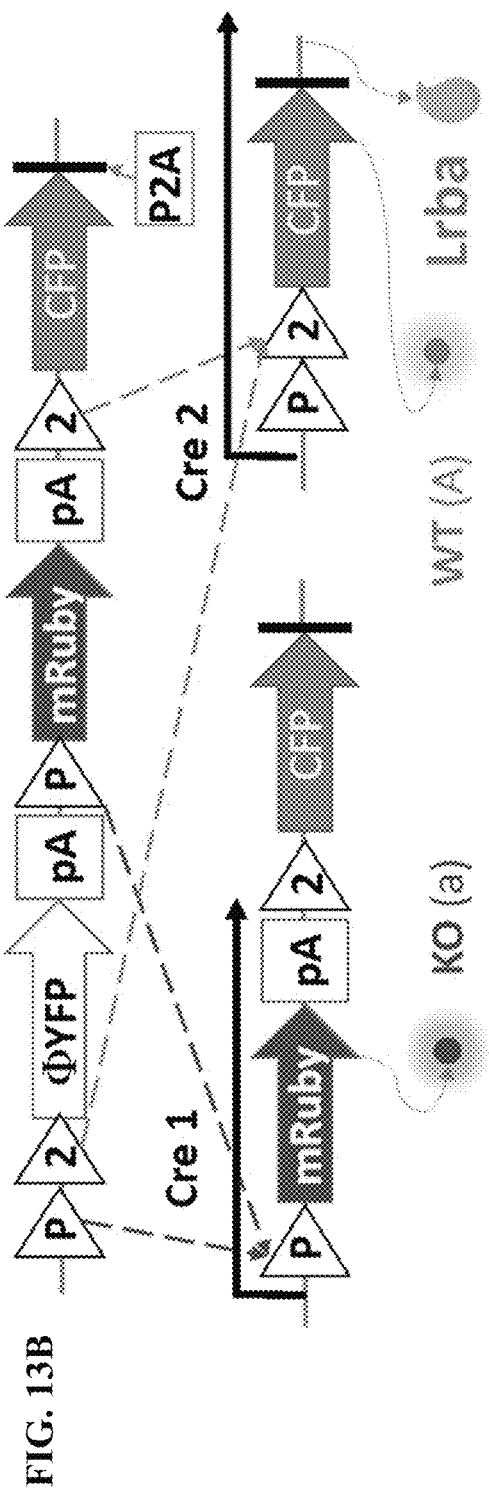

The phenotype-based GI study in the intact animal ('in vivo veritas') provides the most compelling means to define the GPr. While a physical interaction study, based on two-hybrid, affinity capture-Western/mass spectrometry, is important, it does not link genotype to phenotype. GI study has been efficiently conducted in yeast but is extremely challenging in humans and animal models. This is because the variations from genetic background, epigenetic modifications,[19] infections, etc.,[20-22] can interfere with or mask a gene's contribution to a phenotype, resulting in low phenotyping sensitivity or even false data.[23,24] An impractically large number of mice is required to obtain meaningful data in GI study. For example, 500,000 subjects might be necessary to achieve sufficient statistical power to detect non-additive effects of genetic variants.3 Since LRBA deficiency is rare, such a human study would be impossible. To fulfil the two requirements, the inventors propose to generate and label the nine genotypes of two genes with four FRs (FIG. 13A) in a single animal (a mouse), so that a large number of immune cells with nine different genotypes can be studies in a single flow cytometry tube (FIG. 10). With large sample size (e.g., ~2×10$^6$ Tregs and ~2×10$^8$ splenocytes/spleen) and eliminated variations, phenotyping sensitivity will be greatly increased (FIGS. 13A-C).

The principle of Genebow is based on, but an improvement over, the Brainbow and Cre/lox system. The mosaic analysis with double markers (MADM) system can be used to produce three genotypes with distinct fluorescent colors in a mouse.[26-28] However, MADM can only label the genotypes of a gene that is mutated and distal to the insertion site of the fluorescent genes on the same chromosome. It cannot be used to label two genes at the same time. Brainbow only labels cells.[25,29] In contrast, Genebow can be used to label the genotypes of two genes. The advantages of Genebow are large sample size and high sensitivity, and thus it can be broadly used to obtain high resolution data of any immunophenotyping based on single cells. Another premise of Genebow is that the competitive assay with different genotypes has been widely used in research, e.g., transplantation of mixed bone marrows and yeast fitness assay.

By studying each cell as an individual analogous to a mouse in a traditional assay, Genebow can greatly increase the sample size (up to several million) and eliminate background variations. Therefore, this greatly increases phenotyping sensitivity, making it possible, for the first time, to efficiently conduct GI study in animal models at very high resolution. While traditional GI study methods based on one-genotype-one-animal are much less powerful; 2) Genebow will be used to clearly determine whether the genetic interaction of LRBA and NFKB1 plays a critical role in regulating the development and autoimmune-suppression of Tregs in vivo, and thus will result in a clear GPr. These GI studies that require such large sample sizes cannot be conducted using current techniques.

Preliminary Results

1. LRBA Interacts with MAPKs and NFkB (FIGS. 11A-E).

FIG. 11A shows that LRBA knockdown (KD) increases NFkB activity.

Figure 11D:
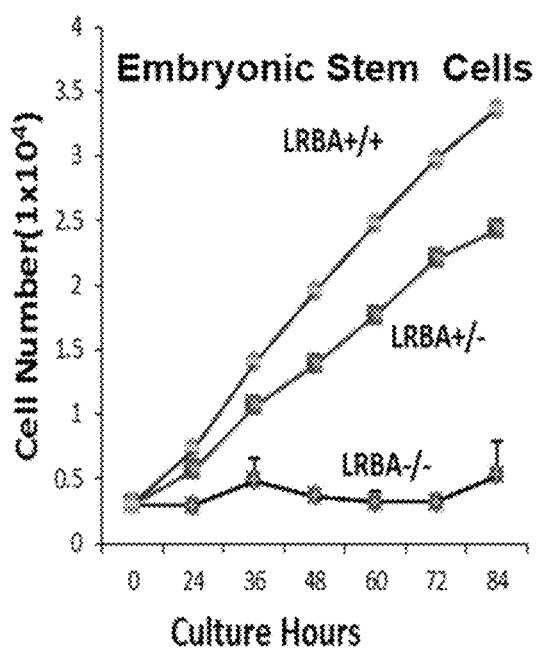
Figure 11E:
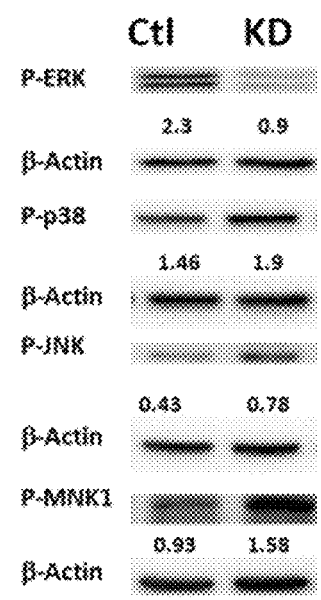

Consistently, phospho (P)-NFkB and cell survival (FIG. 11B) are increased, in agreement with NFkB being a major cell survival regulator. FIG. 11B shows that the inhibition of NFkB by PS-341 promotes apoptosis, which can be rescued by LRBA KD, suggesting that LRBA KD functions against PS-341 by increasing NFkB activity. LRBA promoter has several NFkB binding sites conserved in mouse. FIG. 11C shows that NFkB increases LRBA promoter activity. Lrba is required for cell proliferation. The results in FIG. 11D demonstrate that LRBA interacts with important genes in regulating apoptosis and proliferation. FIG. 11E shows that LRBA KD downregulates P-ERK but upregulates P-p38, P-JNK and correspondingly MAPK substrate P-MNK1. Complementing this data, MAPK (ERK orthologue) is decreased but JNK increased upon rugose (LRBA orthologue) mutation.[30]

2. Construction of Target Vector and Single Guide RNA (sgRNA)/Cas9 Vector (FIGS. 12A-F).

Figure 12B:
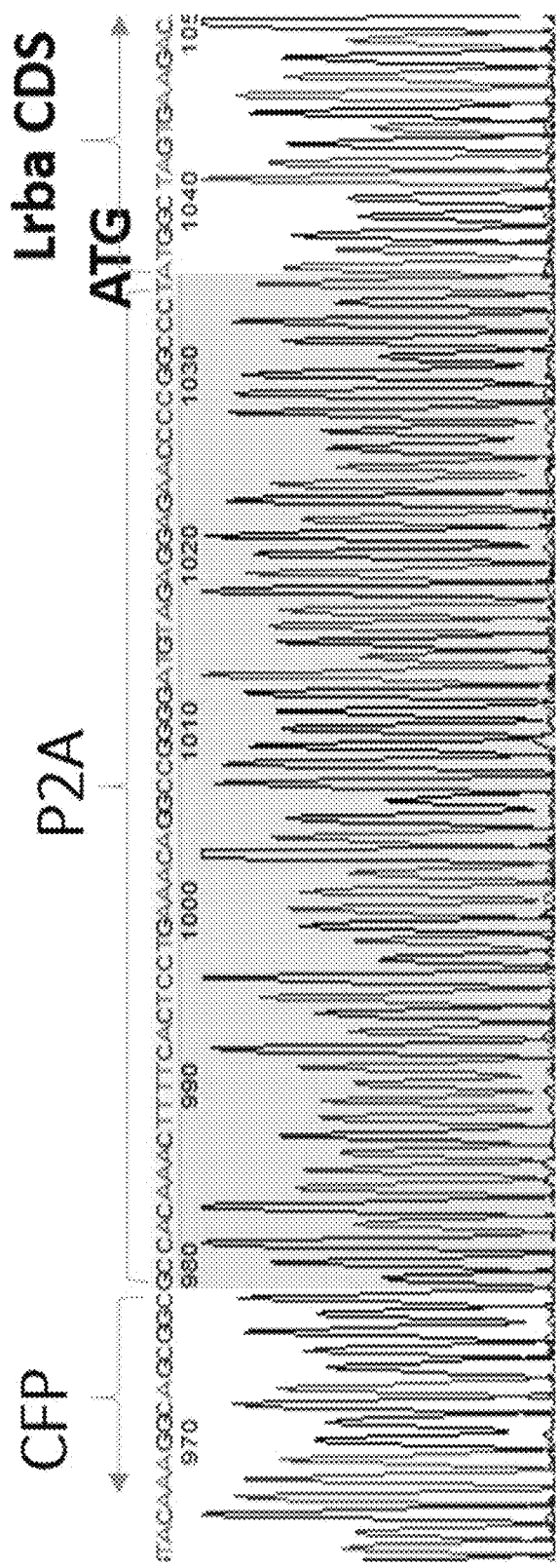
Figure 12D:
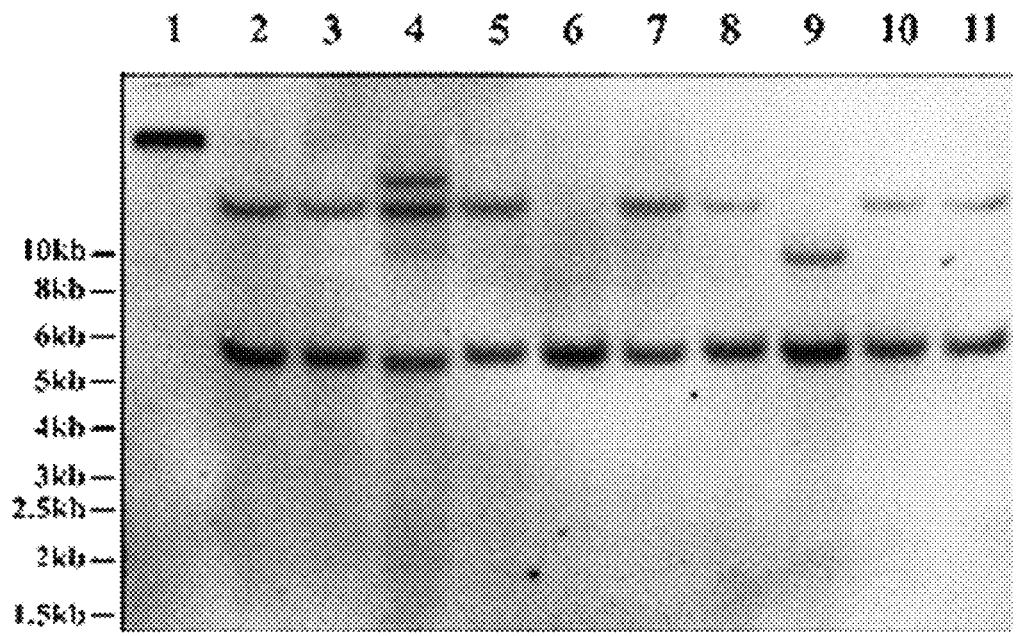
Figure 12E:
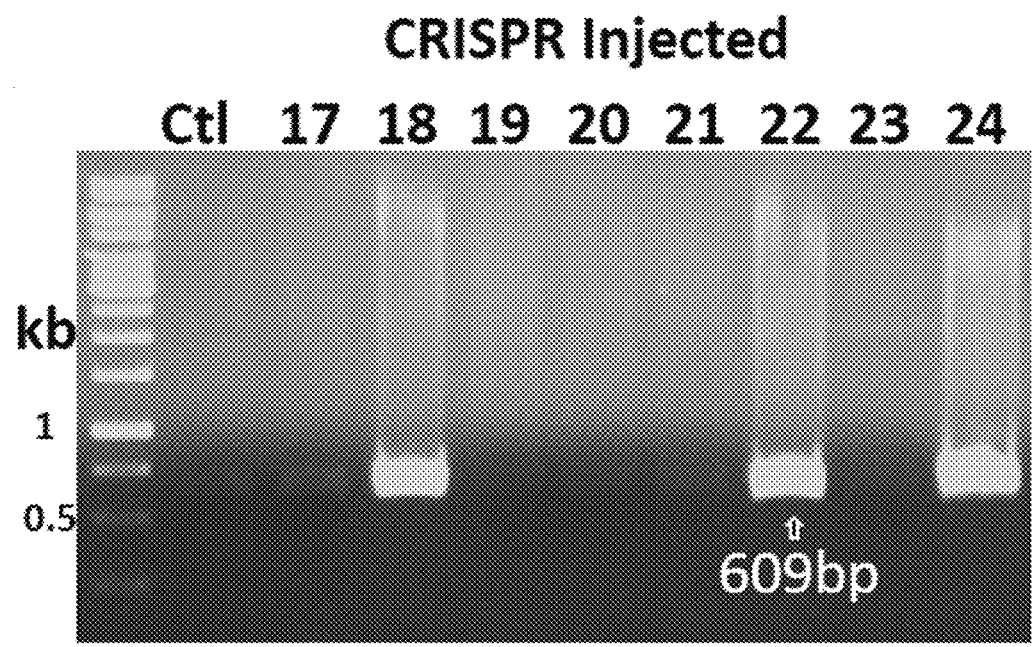

The methods have been described in the inventors' recent publication, which is incorporated herein by reference in its entirety.[7] The one-step generation of a mouse model by CRISPR requires a sgRNA/Cas9 vector and a target repair template vector for each gene. The Lrba target vector was constructed from a BAC clone using homologous recombineering (HR). The subsequent engineering of the vector included multiple rounds of HR and the inventors' CRISPR cloning method.[6] The correct cloning of the target vector was characterized by restriction digestion and then confirmed by sequencing (FIGS. 12A-B). The gRNA sequence was cloned into the pX330 vector.[31] The inventors then conducted CRISPR-mediated knockin in mouse ES cells and zygotes.[32] The inventors found that 67% of G418-positive ES clones are specifically targeted (FIG. 12C). Southern blot (D) confirmed the PCR results. The inventors also obtained high targeting efficiency (32%) and survival rate (87% of two cell eggs, 57% of blastocysts) of zygotes injected with only ⅓ of the normal concentrations of CRISPR reagents (FIG. 12E). The inventors also attempted a knockin construct with short homologous arms and obtained high knockin efficiency (FIG. 12F).

Production of the Nine Genotypes of Two Genes Specifically Labeled (the Genebow Principle).

TCLC1 (FIG. 13A) will be knocked into the genomic loci of Lrba. Cre recombinase-mediated recombination turns on red FR1 (knockout, ko, allele) or blue CFP (wild type, wt, allele) (FIG. 13B). The frequencies of the ko and wt alleles should be equal, as Cre stochastically chooes each lox pair. As each cell has two alleles, ko cells (with two ko alleles) will be labeled as red fluorescent color (FC), wt cells as blue FC, and heterozygous (het) cells as red/blue FCs. Thus wt and ko cells can be produced in equal number. Similarly, Nfkb1 can be labeled with two other FRs: ko (purple), het (purple/green) and wt (green) by knocking in TCLC2. The nine genotypes of the two genes thus can be produced and respectively labelled with four FRs (FIG. 10).

Genebow can Produce High Resolution Phenotyping Data Required for GI Study.

Statistically, phenotyping sensitivity is dependent positively on sample size but inversely on variation. The inventors propose to study each cell as an individual, analogous to a mouse in a traditional assay, to greatly increase the sample size (up to several million: ~2×106 Tregs/spleen). This can be done by producing all genotypes of two genes in a single animal (e.g., a single mouse) and analyzing cells with these genotypes in one vessel (e.g., flow cytometry tube). Thus, there are no background variations between the cells, because the cells from the same mouse should have the same genetic background, epigenetic modifications and environmental input. With greatly increased sample size and zero variation, high resolution (e.g., 1000 times higher than current methods) phenotyping data can be obtained (FIG. 13C).

To generate a Genebow mouse model in which Lrba and Nfkb1 expression can be turned on/off in a spatiotemporal and trackable manner. The CRISPR system is currently used to quickly generate mouse models (~3 months) with high efficiency (up to 78%) and ~100% germline transmission.[39-44] It causes DNA double strand break (DSB), which can be repaired by homology-directed-repair pathways. A DNA fragment flanked by two homologous sequences can be inserted into the DSB with high efficiency.[45] By using this technique, the inventors obtained correctly targeted ES cells and zygotes at high efficiency (67% and 32%, respectively).[7] Therefore, the inventors will take advantage of the efficient multiplex targeting CRISPR system to knock the two TCLCs into the genomic loci of Lrba and Nfkb1, and the CreERT2 into the Rosa26 genomic locus. (FIG. 13A).[41,42]

Construction of CRISPR Targeting Vectors.

Figures 14A, 14B:
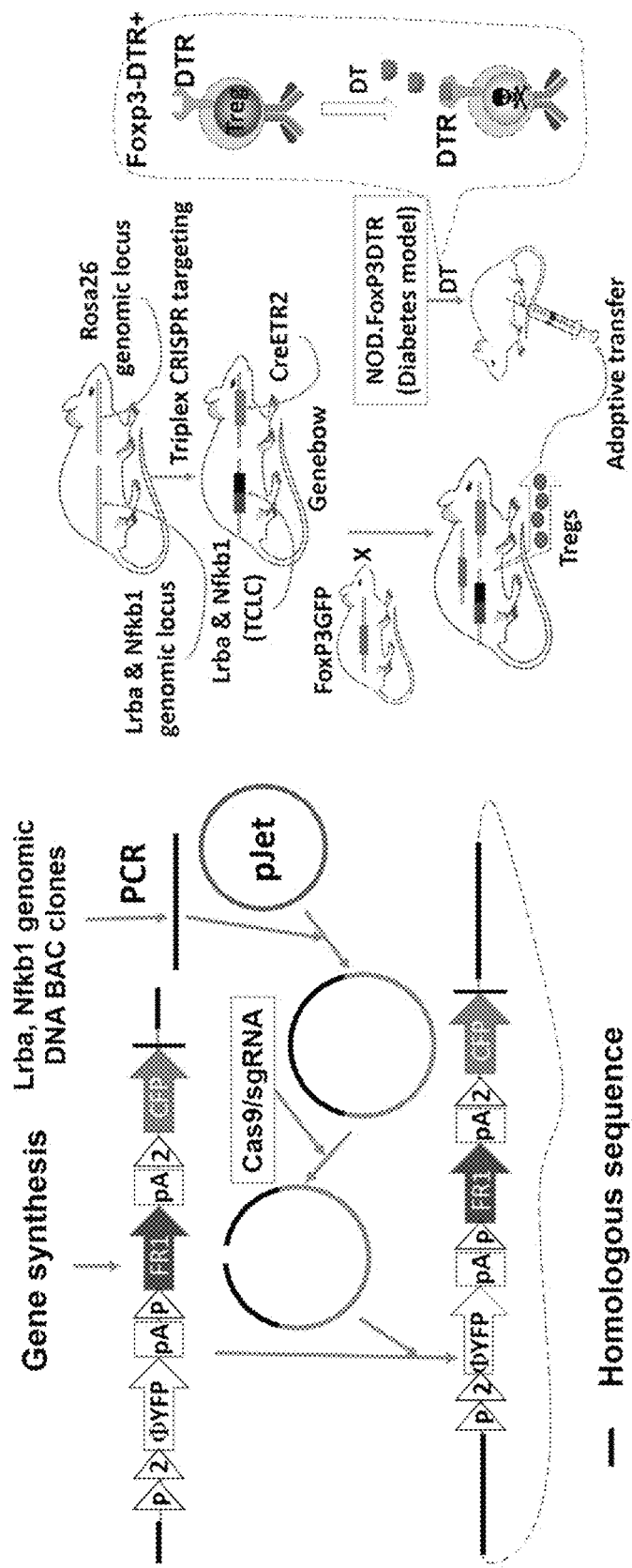

Two vectors, i.e., a donor vector and Cas9/sgRNA vector, are required for targeting each gene. The Cas9/sgRNA vector provides Cas9 endonuclease and a target site-specific sgRNA to cleave the target site. The donor vector contains a TCLC flanked by two homologous fragments and serves as a CRISPR repair template to mediate the knockin of the TCLC. The inventors have established a protocol to readily construct these vectors.[6] Lrba & Nfkb1: The Cas9/sgRNA vector for Lrba is ready and a Cas9/sgRNA vector for Nfkb1 will be cloned as described.7 The detailed cloning strategy of donor vectors is shown in FIG. 14A. CreERT2: CreERT2 consists of the Cre linked to the ligand-binding domain of the estrogen receptor. Cre recombinase activity thus can be efficiently induced by Tamoxifen (TAM) to mediate recombination between two lox sites (FIG. 13B).[46-48] Although transgenic mice that harbor this transgene are available, they are not on a NOD background, which is required for this study. The sgRNA vector for this knockin is ready, and the donor vector pMB80 has been obtained from Addgene.[49] The functionality of the CRISPR vectors for the genes will be validated in ES cells. These vectors will tested in ES cells before zygote injection and optimized as necessary using the inventors' CRISPR vector modification technique.[6] Briefly, triple knockins of the two TCLCs and CreERT2 will be obtained by using the CRISPR technique (FIGS. 12A-F).[4] The corrected targeted ES clones, confirmed by 5' and 3' PCR and Southern blot, will be subjected to TAM-induced Cre-cleavage. Gene expression will be detected by the expression of fluorescent proteins by flow cytometry directly.

Generation of Mouse Model Through CRISPR Technology.

The T7 promoter will be added to the sgRNAs of Nfkb1 or Rosa26 by PCR.6,39 The RNAs will be synthesized by T7 RNA polymerase in vitro and purified.6 Then, the Cas9 mRNA (TriLink)/sgRNA/plasmid donor (1 ng/µl/0.5 ng/µl/2 ng/µl) for each gene will be injected into the pronucleus of fertilized eggs. The concentrations of CRISPR reagents are only 1/5 of the amounts described,[50] but they produce high targeting efficiency and low toxicity (FIG. 12E). The genomic DNA from targeted and control mice (age 8 to 12 days) will be extracted from clipped toes and used to PCR-identify mice that have Lrba, Nfkb1, and Rosa26 correctly targeted at 5' and 3' ends (FIG. 12C),[4] which will be confirmed by Southern blot with the probes from CFP or RFP (FIG. 12D).4

Expected Outcomes and Alternative Strategy: 1) The inventors expect to obtain the correctly triple-targeted mice. The three loci have been targeted by traditional and/or CRISPR methods and disruption of any of them is not lethal in humans and/or mice.51 The Rosa26 is a safe harbor for knockin.[52] Although TCLC is large (~3 kb), the inventors have already inserted large (7.4 and 5.8 kb) fragments into the Lrba locus at high efficiency (FIGS. 12A-F). Others have also inserted ~6 kb fragments.[39,53] The off-target mutations induced by CRISPR targeting are low or undetectable in mice.[54,55] Furthermore, the inventors will use the new high-fidelity CRISPR-Cas9 nuclease to eliminate off-targeting.[56] Triple knockin should not be a concern as nine target loci were simultaneously edited in mouse zygotes.[57] If it is, single and/or double knockins, probably as side products of the triple targeting, will be obtained separately and then bred into one triple knockin.

Determination of how the Genetic Interaction of Lrba and Nfkb1 Regulates the Development and Function of Treg.

Many autoimmune diseases are caused by autoantibodies. Tregs play a determinant role in controlling autoimmunity,[58] likely by preventing autoantibody production, as Treg deficiency results in overproduction of autoantibodies. Treg is downregulated in 73% of LRBA deficiency, and autoantibodies are overproduced in LRBA-deficient patients. Thus, Tregs are likely defective and play a key role in LRBA deficiency and it is important to study how Treg development and function are regulated by LRBA. Furthermore, highly variable clinical presentations indicate background genes have a strong influence on the overall penetrance of the phenotype. LRBA deficiency is modified by other genes to the extent that one subject is asymptomatic. One of the most important modifiers could be NFKB1. LRBA and NFKB1 are closely related, e.g., among the genes that cause autoimmunity when mutated, NFKB1 has the most autoimmune problems that are found in LRBA deficiency, and NFKB1 also likely regulates Tregs. It would be intriguing to study the genetic interaction of the two genes. Thus, an objective of this study was to determine whether Lrba plays a critical role, modified by Nfkb1, in autoimmune diseases by regulating Treg development and function. The inventors' hypothesis is that deregulation of Lrba and Nfkb1 genetic interaction impairs the development and function of Tregs, resulting in reduced cell number and ability to suppress autoimmunity. To test this hypothesis, Tregs with nine different genotypes from Genebow mice will be transferred to an autoimmune mouse model to study how the genotype affects the development and suppressive function of Tregs. It is the inventors' expectation that the phenotypic differences of the nine genotypes will be detected at high resolution to determine whether LRBA plays, modified by NFKB1, a critical role in regulating Tregs to suppress autoimmunity. It will demonstrate that genetic interaction study, for the first time, can be efficiently conducted in animal models.

LRBA and NFKB1 interact with each other (FIGS. 11A-E). NFKB1, among the genes that cause autoimmunity when mutated, has the most autoimmune problems that are found in LRBA deficiency. Mutation of NFKB2 or several upstream genes of NFKB also cause immunodeficiency and autoimmunity.[59] LPS upregulates both Lrba and Nfkb1. Both genes interact with Notch1 and MAPK.[16] LRBA-NFKB1 fusion is present in cancers,[60] reminiscent of BCR-ABL fusion in leukemia. NF-κB family member Rel is required to turn on FoxP3, the most important transcription factor for Tregs, and NFKB1 p105 is a repressor of Rel, suggesting that NFKB1 may regulate Tregs. Therefore, Lrba and Nfkb1 likely interact with each other to regulate Tregs and play a major role in autoimmunity.

Testing Whether the Genetic Interaction of Lrba and Nfkb1 is Required for Treg Development.

The majority of Tregs are generated in thymus and matured into functional Tregs in the periphery.[58] One of the most important Treg subsets is T follicular Treg (Tfr). Tfr cells promote the production of high affinity antibodies but suppress autoantibody production. Tfr deficiency results in overproduction of autoantibodies. Consistently, circulating Tfrs were reduced and autoantibodies were overproduced in LRBA-deficient patients.[2] However, the frequency of recent thymic emigrants (RTEs) was normal,[2] it may suggest that the development of RTEs into Tfrs is impaired. Developmental defects usually result in no or fewer mature cells. Cell number is one of the most important parameters of deregulated immune cells. Because Tfr is one of the end products of Treg development, defective Tfrs indicate defect(s) in one or more developmental stages of Tregs.

Experimental design: As shown in FIGS. 14A-D, tregs will be isolated by cell sorting from T cells enriched by autoMACS as described.[61] T cells will be purified from the spleens of 12-day-old neonates treated with TAM* via negative selection of non-T cells. Cells will be stained with fluorochrome-conjugated CD4, CD3. Foxp3 is genetically tagged with EGFP. Tregs (Foxp3+CD4+CD3+) with nine genotypes will be sorted and 3.6×105 of mixed (4×104/genotype) Tregs will be injected i.p. into Treg-depleted non-obese diabetic (NOD) neonates at 12 days of age as described.61 For depletion of Treg cells, Foxp3-DTR+mice will be injected i.p. with DT or PBS every other day from day 0-10.[61] Finally, treated mice will be killed at 25 days and splenocytes will be stained with fluorochrome-conjugated antibodies of CD4, PD1, CXCR5 (the follicle homing receptor for both B and T cells), followed by standard flow cytometry†. Tfr cells are Foxp3+CD4+PD1+CXCR5+. The following four parameters will be analyzed: total cell numbers, percent of total CD4 T cells, percent of FoxP3+CD4 Treg cells, and percent of CD4+CXCR5+(follicular T) cells. Total Tfr numbers indicate relative differentiation/expansion. Tfr percent of total CD4 T cells provides an indication of relative Tfr cell development compared with total CD4 T cells. Tfr percent of FoxP3+CD4 Treg indicates Tfr cell development versus expansion of precursor Treg cells. Tfr percent of CD4+CXCR5+cells indicates the Tfr/Tfh ratio, which serves as an important way to gauge the GC reaction. GFP levels represent FoxP3 expression level in Tregs.

*TAM-induced Cre recombination. The TAM-inducible Cre system allows optimizing the dose and time of TAM administration to have complete or near complete Cre recombination, which will be determined by flow cytometry of Tregs. If the recombination is completed, RFP+(wt) or mKate2+(ko) Tregs should be a half of total Tregs (all Tregs are labeled with EGFP). TAM will be administered to neonates via lactating mother intraperitoneally (ip) injected with tamoxifen at a dosage of 0, 50, 100, 200 mg/kg body weight, once per day from P3 to P5.

† Flow cytometry. The LSR-II flow cytometer has an analysis rate of up to 40,000 cells per second and the capacity to measure 16 cell markers. 1) To exclude cell aggregates, two sequential gates of scatter width vs height signals will be applied. The singlet population will then be gated by forward scatter vs side scatter to exclude dead cells and debris. "Live cells" will be first gated using a contour plot and then switched to a dot plot for easy monitoring of acquisition. 2) A FMO-control (Fluorescence Minus One) is a control sample composed of all antibody labels except one, and it will be used as a negative control in place of an isotype control for that antibody staining.

Determination of Whether the Genetic Interaction of Lrba and Nfkb1 is Required for the Autoimmune-Suppression Function of Tregs.

Some LRBA-deficient patients have reduced Tfrs, defective Tregs with decreased suppressive ability in vitro and autoantibody overproduction,[2] it is unknown whether the defective Tregs cause the autoimmune diseases, because their suppressive ability in vivo has not been studied. It is also unknown whether NFKB1 deficiency causes autoimmunity by causing defective Tregs, although it likely does as NFKB1 closely interacts with LRBA and causes similar manifestations of autoimmunity when mutated. The inventors hypothesize that the deregulated GI of Lrba and Nfkb1 causes defective Tregs, which plays a major role in causing a variety of autoimmune diseases. To test this hypothesis, the autoimmune-suppression ability of Tregs with 9 different genotypes will be compared in an autoimmune diabetes mouse model (100% spontaneously develop into diabetes). Depletion of Treg greatly accelerates this process.

Experimental design: The following experiments will be conducted as described.[61] Tregs will be isolated as described above with the exception that the Tregs mouse donors will be 12 and 19 days of age. Treg-depleted NOD neonates (Foxp3-DTR+) at 12 and 19 days of age will be injected ip with 3.6×105 of Tregs† for each genotype from Genebow mice of the same age, and then followed for manifestations of autoimmune disease up to 100 days. The reason same age Tregs are to be injected into the same age of mice is that recent thymic emigrant Tregs take about 3 weeks to be matured into Tfrs. Blood glucose levels will be measured every 3 days after cell transfer for 30 days. The measurements for each group at every time point will be statistically analyzed. Other readouts are organ infiltration, weight loss, and death.[61]

†Pooled Tregs: For testing whether the genetic interaction of Lrba and Nfkb1 is required for Treg development 3.6×105 per Treg injection is desired. Three injections require 1.08× 106. It may be possible to obtain such amount of Tregs from one mouse. If not, sorted Tregs will be pooled from several mice. For determining whether the genetic interaction of Lrba and Nfkb1 is required for the autoimmune suppression function of Tregs, 3.6×105 per Treg injection for each genotype is desired. For 9 injections (each genotype per injection) in triplicate will require 10×106 Tregs. The inventors thus will pool sorted Tregs from ~10 mice. To ensure that each mouse has the same contribution to the pooled Tregs, the inventors will mix equal numbers of Tregs for each genotype from each mouse. In this manner, the pooled Tregs for each genotype will have the same genetic background, epigenetic modifications and environmental input as they were from one mouse.

Expected Outcomes, and Alternative Strategy. The inventors expect that 1) knockout (ko) of either or both genes will result in reduced Tfr number and suppression, and 2) dbko will have much fewer Tfr cells and less potent suppression than either single ko, and the reduced Tfr number and suppression are not additive results of two single knockouts.

If both are true, it will demonstrate that both genes are required for Treg development and function, and that the two genes genetically interact with each other, and NFKB1 would modify some phenotypes of LRBA deficiency, resulting in variable manifestations. In addition, the inventors expect that any small phenotypic differences between the nine genotypes will be detected by the Genebow model as it is highly sensitive. The Tfr number and suppressive ability of genotypes may follow the order: AABB>(AABb, AaBB)>(AAbb, AaBb, aaBB)>(Aabb, aaBb)>aabb (A=Lrba; B=Nfkb1). Thus the phenotypic difference between a mutant genotype and WT should be caused by that mutant genotype. Moreover, as each gene has two alleles, the dose effects of the two genes alone or in combination on Treg development and function should be detectable. Consequently, the inventors should be able to define a clear GPr at high resolution. These expectations are based, first, on that apoptosis plays a critical role in Treg development. Apoptosis is required for the positive and negative selection of Tregs in the thymus to develop into Tregs with appropriate affinity to self-antigens. In the periphery, Tregs are further shaped and maintained by the self-antigens through apoptosis. Second, there are more apoptosis in LRBA-deficient Tregs. The inventors also found LRBA downregulation induces apoptosis, and LRBA is overexpressed in several cancers. Others found that LRBA overexpression is a molecular signature of both mortality and recurrence risks for breast cancers. NFKB1 is an important cell survival regulator and is required for lymphocyte development,[62] both genes likely exert their roles on apoptosis mainly by intrinsic mechanism. Since all genotypes are in the same mouse, Genebow also can be used to study the extrinsic function of a gene by transferring cells with different combinations of genotypes into wild type mice will allow us to distinguish cell intrinsic function from the extrinsic effects of other cells with the mutation. Alternative strategy: 1) Both genes likely exert their roles on the development and function of Tregs mainly intrinsically, as they may function mainly on intrinsic apoptosis of Tregs. However, even though there are some extrinsic influence, with such high sensitivity of Genebow assay, it should be possible to detect the difference caused by different genotypes. Further, if either of the genes functions extrinsically on apoptosis and confounds the interpretation of results, the inventors will omit Tregs with some genotypes in the Treg injection and should be able to determine what phenotype is caused by the extrinsic effects. It is possible that defects in other cells, such as B and dendritic cells, may contribute to the defective Tregs. If this is the case, the inventors will conduct the above assay with Tregs combined with other type of cells (e.g., B cells) with different genotypes.

Vertebrate Animal Subjects.

Animal model generation. Due to its small size, rapid breeding and low costs, mouse is the choice for this proposal. Type I diabetes is characterized by destruction of the beta cells (insulin-producing cells) relatively early in life, it is thought by autoantibodies against the beta cells. The nonobese diabetic mouse (NOD) is considered to be a good animal model of autoimmune type I diabetes. Two transcription control and labeling cassette (TCLC) will be respectively inserted into the genomic loci of LRBA and NFKB1 by Clustered Regularly Interspaced Short Palindromic Repeats (CRISPR) technique The correctly targeted mice identified will be used as the founders to establish the "Genebow" colony.

Figure 15:
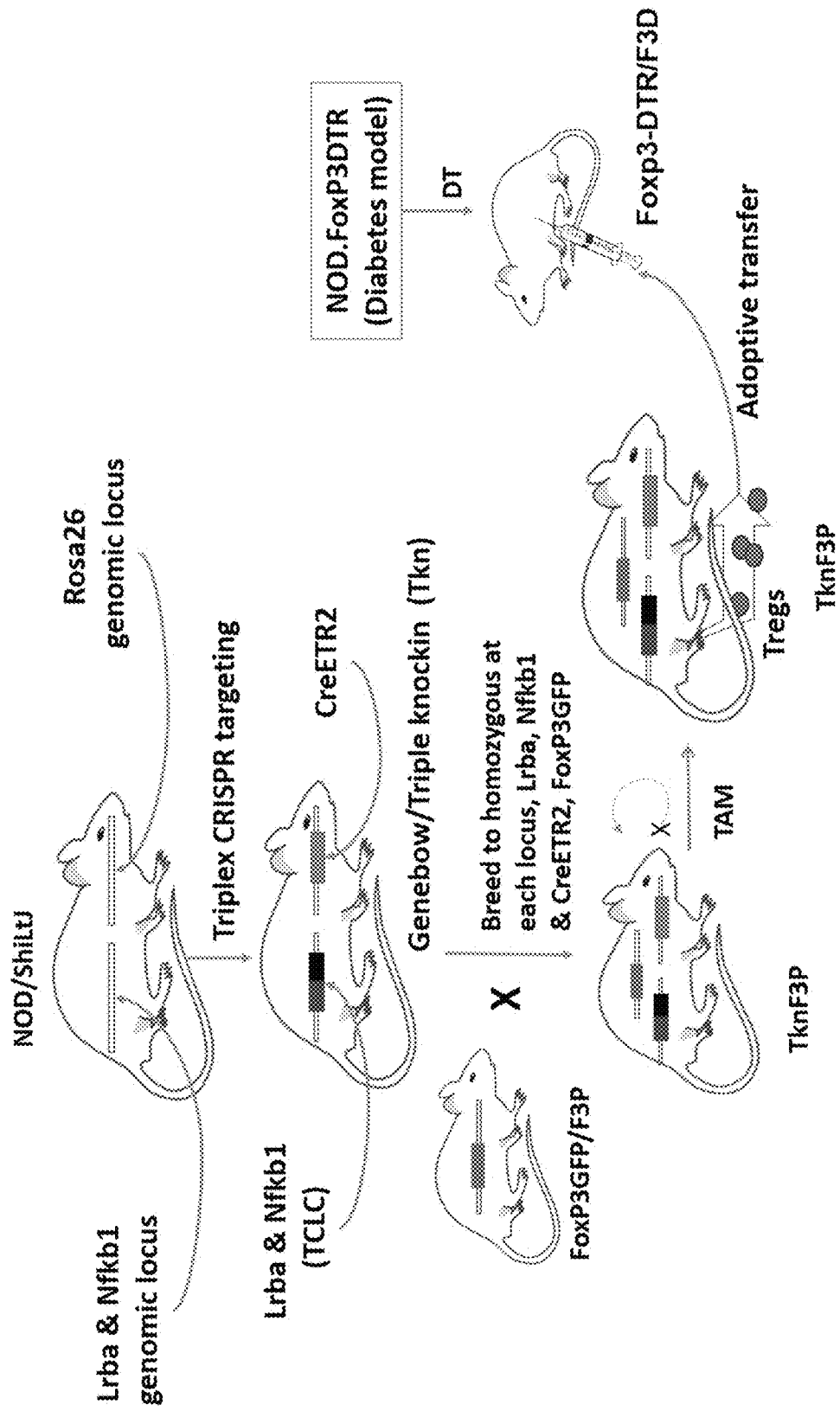
FIG. 15. One-step generation of Genebow mouse model by CRISPR technique and subsequent mating strategy. Two transcription control and labeling cassettes (TCLCs) will be inserted into the genomic loci of Lrba and Nfkb1, respectively, and the CreERT2 into the Rosa26 locus by using the CRISPR technique. Thus, Triple CRISPR targeting will produce Genebow and CreERT2 transgene mice. These genes are on different chromosomes, allowing free segregation and combination of these genes (Lrba and Nfkb1 are 49 Mb away on chromosome 3, CreERT2/Rosa 26 on chromosome 6, and FoxP3GFP on chromosome X).

Study 1: Animal model generation. Both males and females (NOD/ShiLtJ) will be used to establish the colony of the Genebow mouse model from the founders (could be both sex) generated by CRISPR/homology-directed-repair (HDR). During breeding, unwanted mice also will be produced and will be included in the animal number as breeding. The colonies will be established as shown in FIG. 15 and Table 1.

TABLE 1

Mice required to establish the colonies

| Strain name/ | Nickname | Genotype | Animal number | Ages | Sex | Usage |
|---|---|---|---|---|---|---|
| Founders | Triple knockin (Tkn) | Triple knockin (Tkn: Lrba, Nfkb1, Cre/ERT2) | 20 | 2-3 month | Both | Breeding |
| NOD.Foxp3GFP | F3P | Foxp3GFP | 4 | | Both | Tregs are EGFP+ |
| NOD.Tkn.Foxp3P | TknF3P | Tkn(Lrba, Nfkb1, CreERT2+/−)/FoxP3GFP | 100 | 2-3 month | Both | Breeding for neonates |
| NOD/ShiLtJ* | NOD | Wild type | 4 | 2-3 month | Both | Breeding. Mated with the founders |
| NOD.Foxp3DTR/ | F3D | Foxp3-DTR | 4 | 2-3 month | Both | Tregs can be depleted by administration of Diphteria Toxin |
| Total number | | | 132 | | | |

*NOD/ShiLtJ, an autoimmune diabetes mouse model, which 100% spontaneously develop into diabetes and depletion of Treg greatly accelerates this process.

Study 2: Characterization of mouse model functionality. As the inventors conduct experiments with a single mouse that has leukocytes with the nine genotypes: Lrba (wt, het and ko)×Nfkb1 (wt, het and ko), because each genotype has the other eight genotypes as controls in a single mouse, there is no need for control mice for each genotype. Other exogenous protein controls such as Cre background control are not required either, as all cells have the same proteins expressed. Moreover, as flow cytometry can analyze up to millions of cells with multiplex ability, small difference in phenotype can be detected with high confidence (low p values), allowing high sensitivity of phenotyping required to detect phenotypes caused by less penetrance (more dependent on genetic background, typical for genes in mutagenic diseases) of the targeted gene, detecting more phenotypes. Therefore, the number of mice can be greatly reduced

TABLE 2

Mice required to conduct genetic interaction assay of Lrba and Nfkb1 genes

| Group | Nickname | Ages | Sex | Animal number | Usage and Treatment |
|---|---|---|---|---|---|
| 1 | TknF3P | Neonates-several months | Both | 6 * 3 * 3 = 54 [Animals(Both sex) × 3 (TAM doses) × 3 (experimental repeats)] | Optimizing TAM treatment to have complete or near complete Crerecombination. TAM will be administered to neonates via lactating mother intraperitoneally injected with tamoxifen at a dosage of 0, 100 mg/kg body weight, once per day from P3 to P5. |
| 2 | TknF3P | Neonates-several months | Both | 6 * 3 * 3 = 54 [6 Animals (Both sex) × 3 (with and without TAM) × 3 (experimental repeats)] | Treg donors†. Using optimal TAM treatments obtained from group 1. TAM treatment control included. |
| 3 | F3D | Neonates-several months | Both | 6 * 3 * 3 = 54 [Animals (Both sex) × (with or transfer) × 3 (experimental repeats)] | Recipients for Treg transfer. Aim 2.1, Experimental group. Tregs and DT control (PBS) included. |
| 4 | F3D | Neonates-several months | Both | 54 * 1 * 3 = 162 [Animals (Both sex) × (with or without Treg transfer) × 3 (experimental repeats)] | Recipients for Treg transfer. Aim 2.2, Experimental group. Tregs and DT control (PBS) included. |
| Total number | | | | 324 | |

Required: 324
+Breeding: 276
Total = 600
Total animal numbers: 900.
†Pooled Tregs: For testing whether the genetic interaction of Lrba and Nfkb1 is required for Treg development, $3.6 \times 10^5$ per Treg injection is desired. Three injections require $1.08 \times 10^6$. The inventors may be able to obtain such amount of Tregs from one mouse. If not, the inventors will pool sorted Tregs from several mice. For determination of whether the genetic interaction of Lrba and Nfkb1 is required for the autoimmne suppression function of Tregs, $3.6 \times 10^5$ per Treg injection for each genotype is desired. For 9 injections (each genotype per injection) in triplicate will require $10 \times 10^6$ Tregs. The inventors thus will pool sorted Tregs from ~10 mice. To ensure that each mouse has the same contribution to the pooled Tregs, the inventors will mix equal numbers of Tregs for each genotype from each mouse. In this manner, the pooled Tregs for each genotype will have the same genetic background, epigenetic modifications and environmental input as they were from one mouse.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES FOR SUPPLEMENTAL DISCLOSURE 2

1. Gamez-Diaz, L., August, D., Stepensky, P., Revel-Vilk, S., Seidel, M. G., Noriko, M., Morio, T., Worth, A. J., Blessing, J., Van de Veerdonk, F., Feuchtinger, T., Kanariou, M., Schmitt-Graeff, A., Jung, S., Seneviratne, S., Burns, S., Belohradsky, B. H., Rezaei, N., Bakhtiar, S., Speckmann, C., Jordan, M. & Grimbacher, B. The extended phenotype of LPS-responsive beige-like anchor protein (LRBA) deficiency. J Allergy Clin Immunol 137, 223-30 (2016).
2. Charbonnier, L. M., Janssen, E., Chou, J., Ohsumi, T. K., Keles, S., Hsu, J. T., Massaad, M. J., Garcia-Lloret, M., Hanna-Wakim, R., Dbaibo, G., Alangari, A. A., Alsultan, A., Al-Zahrani, D., Geha, R. S. & Chatila, T. A. Regulatory T-cell deficiency and immune dysregulation, polyendocrinopathy, enteropathy, X-linked-like disorder caused by loss-of-function mutations in LRBA. J Allergy Clin Immunol 135, 217-27 (2015).
3. Zuk, O., Hechter, E., Sunyaev, S. R. & Lander, E. S. The mystery of missing heritability: Genetic interactions create phantom heritability. Proc Natl Acad Sci USA 109, 1193-8 (2012).
4. Wang, J. W., Howson, J. M., Ghansah, T., Desponts, C., Ninos, J. M., May, S. L., Nguyen, K. H., Toyama-Sorimachi, N. & Kerr, W. G. Influence of SHIP on the NK repertoire and allogeneic bone marrow transplantation. Science 295, 2094-7 (2002).
5. Wang, J. W., Howson, J., Haller, E. & Kerr, W. G. Identification of a novel lipopolysaccharide-inducible gene with key features of both A kinase anchor proteins and chsl/beige proteins. J Immunol 166, 4586-95 (2001).
6. Wang, J. W., Wang, A., Li, K., Wang, B., Jin, S., Reiser, M. & Lockey, R. F. CRISPR/Cas9 nuclease cleavage combined with Gibson assembly for seamless cloning. BioTechniques 58, 161-70 (2015).
7. Wang, B., Li, K., Wang, A., Reiser, M., Saunders, T. L., Lockey, R. F. & Wang, J. W. Highly efficient CRISPR/HDR-mediated knockin in mouse embryonic stem cells and zygotes. BioTechniques. 59, 201-208 (2015).
8. Serwas, N. K., Kansu, A., Santos-Valente, E., Kuloglu, Z., Demir, A., Yaman, A., Yaneth Gamez Diaz, L., Artan, R., Sayar, E., Ensari, A., Grimbacher, B. & Bortug, K. Atypical Manifestation of LRBA Deficiency with Predominant IBD-like Phenotype. Inflamm Bowel Dis 21, 40-7 (2015).
9. Seidel, M. G., Hirschmugl, T., Gamez-Diaz, L., Schwinger, W., Serwas, N., Deutschmann, A., Gorkiewicz, G., Zenz, W., Windpassinger, C., Grimbacher, B., Urban, C. & Bortug, K. Long-term remission after allogeneic hematopoietic stem cell transplantation in LPS-responsive beige-like anchor (LRBA) deficiency. J Allergy Clin Immunol (2014).
10. Wang, J.-W. & Lockey, R. F. Lipopolysaccharide-responsive beige-like anchor (LRBA), a novel regulator of human immune disorders. Austin Journal of Clinical Immunology 1, 9 (2014).
11. Alkhairy, O. K., Abolhassani, H., Rezaei, N., Fang, M., Andersen, K. K., Chavoshzadeh, Z., Mohammadzadeh, I., El-Rajab, M. A., Massaad, M., Chou, J., Aghamohammadi, A., Geha, R. S. & Hammarstrom, L. Spectrum of Phenotypes Associated with Mutations in LRBA. J Clin Immunol 36, 33-45 (2016).
12. Alangari, A., Alsultan, A., Adly, N., Massaad, M. J., Kiani, I. S., Aljebreen, A., Raddaoui, E., Almomen, A. K., Al-Muhsen, S., Geha, R. S. & Alkuraya, F. S. LPS-responsive beige-like anchor (LRBA) gene mutation in a family with inflammatory bowel disease and combined immunodeficiency. J Allergy Clin Immunol 130, 481-8 e2 (2012).
13. Lo, B., Zhang, K., Lu, W., Zheng, L., Zhang, Q., Kanellopoulou, C., Zhang, Y., Liu, Z., Fritz, J. M., Marsh, R., Husami, A., Kissell, D., Nortman, S., Chaturvedi, V., Haines, H., Young, L. R., Mo, J., Filipovich, A. H., Bleesing, J. J., Mustillo, P., Stephens, M., Rueda, C. M., Chougnet, C. A., Hoebe, K., McElwee, J., Hughes, J. D., Karakoc-Aydiner, E., Matthews, H. F., Price, S., Su, H. C., Rao, V. K., Lenardo, M. J. & Jordan, M. B. AUTOIMMUNE DISEASE. Patients with LRBA deficiency show CTLA4 loss and immune dysregulation responsive to abatacept therapy. Science 349, 436-40 (2015).
14. Schreiner, F., Plamper, M., Dueker, G., Schoenberger, S., Gamez-Diaz, L., Grimbacher, B., Hilger, A. C., Gohlke, B., Reutter, H. & Woelfle, J. Infancy-onset T1DM, short stature and severe immunodysregulation in two siblings with a homozygous LRBA-mutation. J Clin Endocrinol Metab, jc20153382 (2016).
15. Schreiber, S. L., Preiss, A., Nagel, A. C., Wech, I. & Maier, D. Genetic screen for modifiers of the rough eye phenotype resulting from overexpression of the Notch antagonist hairless in Drosophila. Genesis 33, 141-52. (2002).
16. Shamloula, H. K., Mbogho, M. P., Pimentel, A. C., Chrzanowska-Lightowlers, Z. M., Hyatt, V., Okano, H. & Venkatesh, T. R. rugose (rg), a Drosophila A kinase anchor protein, is required for retinal pattern formation and interacts genetically with multiple signaling pathways. Genetics 161, 693-710 (2002).
17. de Souza, N., Vallier, L. G., Fares, H. & Greenwald, I. SEL-2, the C. elegans neurobeachin/LRBA homolog, is a negative regulator of lin-12/Notch activity and affects endosomal traffic in polarized epithelial cells. Development 134, 691-702 (2007).
18. Wang, J. W., Gamsby, J. J., Highfill, S. L., Mora, L. B., Bloom, G. C., Yeatman, T. J., Pan, T. C., Ramne, A. L., Chodosh, L. A., Cress, W. D., Chen, J. & Kerr, W. G. Deregulated expression of LRBA facilitates cancer cell growth. Oncogene 23, 4089-97 (2004).
19. Bryant, C. D., Zhang, N. N., Sokoloff, G., Fanselow, M. S., Ennes, H. S., Palmer, A. A. & McRoberts, J. A. Behavioral differences among C57BL/6 substrains: implications for transgenic and knockout studies. J Neurogenet 22, 315-31 (2008).
20. Kado, S., Uchida, K., Funabashi, H., Iwata, S., Nagata, Y., Ando, M., Onoue, M., Matsuoka, Y., Ohwaki, M. & Morotomi, M. Intestinal microflora are necessary for development of spontaneous adenocarcinoma of the large intestine in T-cell receptor beta chain and p53 double-knockout mice. Cancer Res 61, 2395-8 (2001).
21. Franklin, C. L. Microbial considerations in genetically engineered mouse research. ILAR J 47, 141-55 (2006).
22. Treuting, P. M., Clifford, C. B., Sellers, R. S. & Brayton, C. F. Of mice and microflora: considerations for genetically engineered mice. Vet Pathol 49, 44-63 (2012).
23. Ridgway, W. M., Healy, B., Smink, L. J., Rainbow, D. & Wicker, L. S. New tools for defining the 'genetic background' of inbred mouse strains. Nat Immunol 8, 669-73 (2007).
24. Sundberg, J. P., Roopenian, D. C., Liu, E. T. & Schofield, P. N. The Cinderella effect: searching for the best fit between mouse models and human diseases. J Invest Dermatol 133, 2509-13 (2013).
25. Cai, D., Cohen, K. B., Luo, T., Lichtman, J. W. & Sanes, J. R. Improved tools for the Brainbow toolbox. Nat Methods 10, 540-7 (2013).
26. Espinosa, J. S., Tea, J. S. & Luo, L. Mosaic analysis with double markers (MADM) in mice. Cold Spring Harb Protoc 2014, 182-9 (2014).
27. Hippenmeyer, S., Johnson, R. L. & Luo, L. Mosaic analysis with double markers reveals cell-type-specific paternal growth dominance. Cell Rep 3, 960-7 (2013).
28. Liu, C., Sage, J. C., Miller, M. R., Verhaak, R. G., Hippenmeyer, S., Vogel, H., Foreman, O., Bronson, R. T., Nishiyama, A., Luo, L. & Zong, H. Mosaic analysis with double markers reveals tumor cell of origin in glioma. Cell 146, 209-21 (2011).
29. Livet, J., Weissman, T. A., Kang, H., Draft, R. W., Lu, J., Bennis, R. A., Sanes, J. R. & Lichtman, J. W. Transgenic strategies for combinatorial expression of fluorescent proteins in the nervous system. Nature 450, 56-62 (2007).
30. Wech, I. & Nagel, A. C. Mutations in rugose promote cell type-specific apoptosis in the Drosophila eye. Cell Death Differ 12, 145-52 (2005).
31. Cong, L., Ran, F. A., Cox, D., Lin, S., Barretto, R., Habib, N., Hsu, P. D., Wu, X., Jiang, W., Marraffini, L. A. & Zhang, F. Multiplex genome engineering using CRISPR/Cas systems. Science 339, 819-23.
32. Yang, H., Wang, H. & Jaenisch, R. Generating genetically modified mice using CRISPR/Cas-mediated genome engineering. Nat Protoc 9, 1956-68 (2014).
33. Erard, M., Fredj, A., Pasquier, H., Beltolngar, D. B., Bousmah, Y., Derrien, V., Vincent, P. & Merola, F. Mini- 34. Shcherbakova, D. M. & Verkhusha, V. V. Near-infrared fluorescent proteins for multicolor in vivo imaging. Nat Methods 10, 751-4 (2013).
35. Kim, J. H., Lee, S. R., Li, L. H., Park, H. J., Park, J. H., Lee, K. Y., Kim, M. K., Shin, B. A. & Choi, S. Y. High cleavage efficiency of a 2A peptide derived from porcine teschovirus-1 in human cell lines, zebrafish and mice. PLoS One 6, e18556 (2011).
36. Dean, K. M. & Palmer, A. E. Advances in fluorescence labeling strategies for dynamic cellular imaging. Nat Chem Biol 10, 512-23 (2014).
37. Wan, Y. Y. & Flavell, R. A. Identifying Foxp3-expressing suppressor T cells with a bicistronic reporter. Proc Natl Acad Sci USA 102, 5126-31 (2005).
38. Boston-University-and-Boston-Medical-Center. Sample Size Calculations. http://www.bu.edu/orccommittees/iacuc/policies-and-guidelines/sample-size-calculations/.
39. Yang, H., Wang, H., Shivalila, C. S., Cheng, A. W., Shi, L. & Jaenisch, R. One-step generation of mice carrying reporter and conditional alleles by CRISPR/Cas-mediated genome engineering. Cell 154, 1370-9 (2013).
40. Zhou, J., Wang, J., Shen, B., Chen, L., Su, Y., Yang, J., Zhang, W., Tian, X. & Huang, X. Dual sgRNAs facilitate CRISPR/Cas9-mediated mouse genome targeting. FEBS J 281, 1717-25 (2014).
41. Wang, H., Yang, H., Shivalila, C. S., Dawlaty, M. M., Cheng, A. W., Zhang, F. & Jaenisch, R. One-step generation of mice carrying mutations in multiple genes by CRISPR/Cas-mediated genome engineering. Cell 153, 910-8.
42. Yang, H., Wang, H., Shivalila, C. S., Cheng, A. W., Shi, L. & Jaenisch, R. One-step generation of mice carrying reporter and conditional alleles by CRISPR/Cas-mediated genome engineering. Cell 154, 1370-9.
43. Fujii, W., Kawasaki, K., Sugiura, K. & Naito, K. Efficient generation of large-scale genome-modified mice using gRNA and CAS9 endonuclease. Nucleic Acids Res 41, e187.
44. Jinek, M., Chylinski, K., Fonfara, I., Hauer, M., Doudna, J. A. & Charpentier, E. A programmable dual-RNA-guided DNA endonuclease in adaptive bacterial immunity. Science 337, 816-21 (2012).
45. Donoho, G., Jasin, M. & Berg, P. Analysis of gene targeting and intrachromosomal homologous recombination stimulated by genomic double-strand breaks in mouse embryonic stem cells. Mol Cell Biol 18, 4070-8 (1998).
46. Aghajani, K., Keerthivasan, S., Yu, Y. & Gounari, F. Generation of CD4CreER(T(2)) transgenic mice to study development of peripheral CD4-T-cells. Genesis 50, 908-13.
47. Metzger, D., Clifford, J., Chiba, H. & Chambon, P. Conditional site-specific recombination in mammalian cells using a ligand-dependent chimeric Cre recombinase. Proc Natl Acad Sci USA 92, 6991-5 (1995).
48. Feil, S., Valtcheva, N. & Feil, R. Inducible Cre mice. Methods Mol Biol 530, 343-63 (2009).
49. McLaughlin, M. E., Kruger, G. M., Slocum, K. L., Crowley, D., Michaud, N. A., Huang, J., Magendantz, M. & Jacks, T. The Nf2 tumor suppressor regulates cell-cell adhesion during tissue fusion. Proc Natl Acad Sci USA 104, 3261-6 (2007).
50. Wang, H., Yang, H., Shivalila, C. S., Dawlaty, M. M., Cheng, A. W., Zhang, F. & Jaenisch, R. One-Step Generation of Mice Carrying Mutations in Multiple Genes by CRISPR/Cas-Mediated Genome Engineering. Cell 153, 910-918 (2013).
51. Platt, R. J., Chen, S., Zhou, Y., Yim, M. J., Swiech, L., Kempton, H. R., Dahlman, J. E., Parnas, O., Eisenhaure, T. M., Jovanovic, M., Graham, D. B., Jhunjhunwala, S., Heidenreich, M., Xavier, R. J., Langer, R., Anderson, D. G., Hacohen, N., Regev, A., Feng, G., Sharp, P. A. & Zhang, F. CRISPR-Cas9 knockin mice for genome editing and cancer modeling. Cell 159, 440-55 (2014).
52. Sadelain, M., Papapetrou, E. P. & Bushman, F. D. Safe harbours for the integration of new DNA in the human genome. Nat Rev Cancer 12, 51-8 (2012).
53. Kimura, Y., Hisano, Y., Kawahara, A. & Higashijima, S. Efficient generation of knock-in transgenic zebrafish carrying reporter/driver genes by CRISPR/Cas9-mediated genome engineering. Sci Rep 4, 6545 (2014).
54. Inui, M., Miyado, M., Igarashi, M., Tamano, M., Kubo, A., Yamashita, S., Asahara, H., Fukami, M. & Takada, S. Rapid generation of mouse models with defined point mutations by the CRISPR/Cas9 system. Sci Rep 4, 5396 (2014).
55. Mashiko, D., Fujihara, Y., Satouh, Y., Miyata, H., Isotani, A. & Ikawa, M. Generation of mutant mice by pronuclear injection of circular plasmid expressing Cas9 and single guided RNA. Sci Rep 3, 3355 (2013).
56. Kleinstiver, B. P., Pattanayak, V., Prew, M. S., Tsai, S. Q., Nguyen, N. T., Zheng, Z. & Joung, J. K. High-fidelity CRISPR-Cas9 nucleases with no detectable genome-wide off-target effects. Nature 529, 490-5 (2016).
57. Sakurai, T., Kamiyoshi, A., Kawate, H., Mori, C., Watanabe, S., Tanaka, M., Uetake, R., Sato, M. & Shindo, T. A non-inheritable maternal Cas9-based multiple-gene editing system in mice. Sci Rep 6, 20011 (2016).
58. Cebula, A., Seweryn, M., Rempala, G. A., Pabla, S. S., McIndoe, R. A., Denning, T. L., Bry, L., Kraj, P., Kisielow, P. & Ignatowicz, L. Thymus-derived regulatory T cells contribute to tolerance to commensal microbiota. Nature 497, 258-62 (2013).
59. Cunningham-Rundles, C. Human B cell defects in perspective. Immunol Res 54, 227-32 (2012).
60. Teles Alves, I., Hartjes, T., McClellan, E., Hiltemann, S., Bottcher, R., Dits, N., Temanni, M. R., Janssen, B., van Workum, W., van der Spek, P., Stubbs, A., de Klein, A., Eussen, B., Trapman, J. & Jenster, G. Next-generation sequencing reveals novel rare fusion events with functional implication in prostate cancer. Oncogene 34, 568-77 (2015).
61. Yang, S., Fujikado, N., Kolodin, D., Benoist, C. & Mathis, D. Immune tolerance. Regulatory T cells generated early in life play a distinct role in maintaining self-tolerance. Science 348, 589-94 (2015).
62. Gerondakis, S., Fulford, T. S., Messina, N. L. & Grumont, R. J. NF-kappaB control of T cell development. Nat Immunol 15, 15-25 (2014).
63. Tanaka, K. F., Ahmari, S. E., Leonardo, E. D., Richardson-Jones, J. W., Budreck, E. C., Scheiffele, P., Sugio, S., Inamura, N., Ikenaka, K. & Hen, R. Flexible Accelerated STOP Tetracycline Operator-knockin (FAST): a versatile and efficient new gene modulating system. Biol Psychiatry 67, 770-3 (2010).
64. Baudouin, S. J., Gaudias, J., Gerharz, S., Hatstatt, L., Zhou, K., Punnakkal, P., Tanaka, K. F., Spooren, W., Hen, R., De Zeeuw, C. I., Vogt, K. & Scheiffele, P. Shared synaptic pathophysiology in syndromic and nonsyndromic rodent models of autism. Science 338, 128-32 (2012).

65. Ingenious-Targeting-Laboratory. Flexible Accelerated STOP Tetracycline Operator-knockin (FAST): a versatile and efficient new gene modulating system. http://www.genetargeting.com/products-and-services/types-of-mouse-model s/f-a-s-t/.

Exemplified Embodiments

Examples of embodiments of the invention include, but are not limited to:

Embodiment 1. A non-human animal model comprising nine genotypes of two genes specifically labeled with four distinct detectable labels.

Embodiment 2. The non-human animal model of embodiment 1, wherein the two genes comprise a wild-type first gene (A), a wild-type second gene (B), an inactivated form of the first gene (a), and an inactivated form of the second gene (b), wherein the four distinct detectable labels comprise:
  a first label co-expressed with the wild-type first gene (A),
  a second label co-expressed with the inactivated form of the first gene (a),
  a third label co-expressed with the wild-type second gene (B), and
  a fourth label co-expressed with the inactivated form of the second gene (b).

Embodiment 3. The non-human animal model of embodiment 2, wherein the animal comprises:
  (a) a first genotype comprising homozygous alleles for the wild-type first gene (AA) and homozygous alleles for the wild-type second gene (BB), wherein the wild-type first gene (A) is co-expressed with the first label and the wild-type second gene (B) is co-expressed with the third label;
  (b) a second genotype comprising homozygous alleles for the wild-type first gene (AA), one allele for the wild-type second gene (B), and one allele for the inactivated form of the second gene (b), wherein the first gene (A) is co-expressed with the first label, the second gene (B) is co-expressed with the third label, and wherein the allele for the inactivated form of the second gene (b) is co-expressed with the fourth label;
  (c) a third genotype comprising homozygous alleles for the wild-type first gene (AA) and homozygous alleles for the inactivated form of the second gene (bb), wherein the homozygous alleles for the wild-type first gene (AA) are co-expressed with the first label, and wherein the homozygous alleles for the inactivated form of the second gene (bb) are co-expressed with the fourth label;
  (d) a fourth genotype comprising one allele for the wild-type first gene (A), one allele for the inactivated version of the first gene (a), and homozygous alleles for the wild-type second gene (BB), wherein allele for the wild-type first gene (A) is co-expressed with the first label, the allele for the inactivated version of the first gene (a) is co-expressed with the second label, and the homozygous alleles for the wild-type second gene (BB) are co-expressed with the third label;
  (e) a fifth genotype comprising one allele for the wild-type first gene (A), one allele for the inactivated version of the first gene (a), one allele for the wild-type second gene (B), and one allele for the inactivated form of the second gene (b), wherein the allele for the wild-type first gene (A) is co-expressed with the first label, the allele for the inactivated version of the first gene (a) is co-expressed second label, wherein the allele for the wild-type second gene (B) is co-expressed with the third label, and wherein the allele for the inactivated form of the second gene (b) is co-expressed with the fourth label;
  (f) a sixth genotype comprising one allele for the wild-type first gene (A), one allele for the inactivated version of the first gene (a), and homozygous alleles for the inactivated version of the second gene (bb), wherein the allele for the wild-type first gene (A) is co-expressed with the first label, the allele for the inactivated version of the first gene (a) is co-expressed second label, and wherein the homozygous alleles for the inactivated form of the second gene (bb) are co-expressed with the fourth label;
  (g) a seventh genotype comprising homozygous alleles for the inactivated version of the first gene (aa), and homozygous alleles for the wild-type second gene (BB), wherein the homozygous alleles for the inactivated version of the first gene (aa) are co-expressed with the second label, and wherein the homozygous alleles for the wild-type second gene (BB) are co-expressed with the third label;
  (h) an eighth genotype comprising homozygous alleles for the inactivated version of the first gene (aa), one allele for the wild-type second gene (B), and one allele for the inactivated form of the second gene (b), wherein the homozygous alleles for the inactivated version of the first gene (aa) is co-expressed with the second label, the allele for the wild-type second gene (B) is co-expressed with the third label, and wherein the one allele for the inactivated form of the second gene (b) is co-expressed with the fourth label; and
  (i) a ninth genotype comprising homozygous alleles for the inactivated version of the first gene (aa), and homozygous alleles for the inactivated version of the second gene (bb), wherein the homozygous alleles for the inactivated version of the first gene (aa) is co-expressed with the second label, and wherein the homozygous alleles for the inactivated version of the second gene (bb) is co-expressed with the fourth label.

Embodiment 4. The non-human animal model of embodiment 2 or 3, wherein the first gene is Lrba and the second gene is NFkB, or vice-versa.

Embodiment 5. The non-human animal model of any preceding embodiment, wherein the detectable labels are fluorescent labels or luminescent labels.

Embodiment 6. The non-human animal model of any preceding embodiment, wherein the animal model is a rodent.

Embodiment 7. The non-human animal model of any preceding embodiment, wherein the animal model is a mouse.

Embodiment 8. The non-human animal model of any one of embodiments 1 to 5, wherein the animal model is a primate.

Embodiment 9. The non-human animal model of any preceding embodiment, wherein the animal model is further modified at the genetic or epigenetic level.

Embodiment 10. The non-human animal model of any preceding embodiment, wherein the animal model is further modified at the genetic or epigenetic level so as to be useful in modeling a disease.

Embodiment 11. The non-human animal model of embodiment 10, wherein the disease is selected from the group consisting of cancer, cardiovascular disease, metabolic disease, monogenic disease.

Embodiment 12. The non-human animal model of embodiment 10, wherein the disease is selected from the group consisting of Down Syndrome, cystic fibrosis, glaucoma, type-I diabetes, type-II diabetes, epilepsy, heart disease, muscular dystrophy, and gynecological cancer.

Embodiment 13. A composition comprising a population of cells from the non-human animal of embodiment 1.

Embodiment 14. A method for studying gene-gene interaction, comprising:
providing a non-human animal model of any one of embodiments 1 to 12;
analyzing the interaction of the two genes specifically labeled with four distinct detectable labels.

Embodiment 15. The method of embodiment 14, wherein said analyzing comprises analyzing the characteristics and/or behavior of the animal model or one or more cell populations of the animal model.

Embodiment 16. The method of embodiment 14, wherein said analyzing comprises subjecting cells of the animal model to flow cytometry.

Embodiment 17. The method of embodiment 14, wherein said analyzing is carried out in the presence and/or absence of an exogenous agent.

Embodiment 18. The method of embodiment 14, wherein said analyzing comprises measuring the detectable label of one of the genes and, optionally, comparing the measured detectable label to that of the other gene.

Embodiment 19. The method of embodiment 14, wherein the two genes comprise a wild-type first gene (A), a wild-type second gene (B), an inactivated form of the first gene (a), and an inactivated form of the second gene (b), wherein the four distinct detectable labels comprise:
a first label co-expressed with the wild-type first gene (A),
a second label co-expressed with the inactivated form of the first gene (a),
a third label co-expressed with the wild-type second gene (B), and
a fourth label co-expressed with the inactivated form of the second gene (b); and
wherein said analyzing comprises measuring one or more of the first label, second label, third label, or fourth label.

Embodiment 20. The method of embodiment 19, wherein the animal comprises:
(a) a first genotype comprising homozygous alleles for the wild-type first gene (AA) and homozygous alleles for the wild-type second gene (BB), wherein the wild-type first gene (A) is co-expressed with the first label and the wild-type second gene (B) is co-expressed with the third label;
(b) a second genotype comprising homozygous alleles for the wild-type first gene (AA), one allele for the wild-type second gene (B), and one allele for the inactivated form of the second gene (b), wherein the first gene (A) is co-expressed with the first label, the second gene (B) is co-expressed with the third label, and wherein the allele for the inactivated form of the second gene (b) is co-expressed with the fourth label;
(c) a third genotype comprising homozygous alleles for the wild-type first gene (AA) and homozygous alleles for the inactivated form of the second gene (bb), wherein the homozygous alleles for the wild-type first gene (AA) are co-expressed with the first label, and wherein the homozygous alleles for the inactivated form of the second gene (bb) are co-expressed with the fourth label;
(d) a fourth genotype comprising one allele for the wild-type first gene (A), one allele for the inactivated version of the first gene (a), and homozygous alleles for the wild-type second gene (BB), wherein allele for the wild-type first gene (A) is co-expressed with the first label, the allele for the inactivated version of the first gene (a) is co-expressed with the second label, and the homozygous alleles for the wild-type second gene (BB) are co-expressed with the third label;
(e) a fifth genotype comprising one allele for the wild-type first gene (A), one allele for the inactivated version of the first gene (a), one allele for the wild-type second gene (B), and one allele for the inactivated form of the second gene (b), wherein the allele for the wild-type first gene (A) is co-expressed with the first label, the allele for the inactivated version of the first gene (a) is co-expressed second label, wherein the allele for the wild-type second gene (B) is co-expressed with the third label, and wherein the allele for the inactivated form of the second gene (b) is co-expressed with the fourth label;
(f) a sixth genotype comprising one allele for the wild-type first gene (A), one allele for the inactivated version of the first gene (a), and homozygous alleles for the inactivated version of the second gene (bb), wherein the allele for the wild-type first gene (A) is co-expressed with the first label, the allele for the inactivated version of the first gene (a) is co-expressed second label, and wherein the homozygous alleles for the inactivated form of the second gene (bb) are co-expressed with the fourth label;
(g) a seventh genotype comprising homozygous alleles for the inactivated version of the first gene (aa), and homozygous alleles for the wild-type second gene (BB), wherein the homozygous alleles for the inactivated version of the first gene (aa) are co-expressed with the second label, and wherein the homozygous alleles for the wild-type second gene (BB) are co-expressed with the third label;
(h) an eighth genotype comprising homozygous alleles for the inactivated version of the first gene (aa), one allele for the wild-type second gene (B), and one allele for the inactivated form of the second gene (b), wherein the homozygous alleles for the inactivated version of the first gene (aa) is co-expressed with the second label, the allele for the wild-type second gene (B) is co-expressed with the third label, and wherein the one allele for the inactivated form of the second gene (b) is co-expressed with the fourth label; and
(i) a ninth genotype comprising homozygous alleles for the inactivated version of the first gene (aa), and homozygous alleles for the inactivated version of the second gene (bb), wherein the homozygous alleles for the inactivated version of the first gene (aa) is co-expressed with the second label, and wherein the homozygous alleles for the inactivated version of the second gene (bb) is co-expressed with the fourth label; and
wherein said analyzing comprises measuring one or more of the first label, second label, third label, or fourth label.

Embodiment 21. A method for studying gene-gene interaction, comprising:
providing a population of cells from the non-human animal model of embodiment 1; and
analyzing the interaction of the two genes specifically labeled with four distinct detectable labels.

Embodiment 22. The method of embodiment 21, wherein said analyzing comprises analyzing the characteristics and/or behavior of the cells.

Embodiment 23 The method of embodiment 21, wherein said analyzing comprises subjecting cells of the animal model to flow cytometry.

Embodiment 24. The method of embodiment 21, wherein said analyzing is carried out in the presence and/or absence of an exogenous agent administered to the animal in vivo or brought into contact with the cells in vitro.

Embodiment 25. The method of embodiment 21, wherein said analyzing comprises measuring the detectable label of one of the genes and, optionally, comparing the measured detectable label to that of the other gene.

Embodiment 26. The method of embodiment 21, wherein the two genes comprise a wild-type first gene (A), a wild-type second gene (B), an inactivated form of the first gene (a), and an inactivated form of the second gene (b), wherein the four distinct detectable labels comprise:

a first label co-expressed with the wild-type first gene (A), a second label co-expressed with the inactivated form of the first gene (a), a third label co-expressed with the wild-type second gene (B), and a fourth label co-expressed with the inactivated form of the second gene (b); and wherein said analyzing comprises measuring one or more of the first label, second label, third label, or fourth label (i.e., one, two, three, or all four labels).

Embodiment 27. The method of embodiment 19, wherein the animal comprises:

(a) a first genotype comprising homozygous alleles for the wild-type first gene (AA) and homozygous alleles for the wild-type second gene (BB), wherein the wild-type first gene (A) is co-expressed with the first label and the wild-type second gene (B) is co-expressed with the third label;

(b) a second genotype comprising homozygous alleles for the wild-type first gene (AA), one allele for the wild-type second gene (B), and one allele for the inactivated form of the second gene (b), wherein the first gene (A) is co-expressed with the first label, the second gene (B) is co-expressed with the third label, and wherein the allele for the inactivated form of the second gene (b) is co-expressed with the fourth label;

(c) a third genotype comprising homozygous alleles for the wild-type first gene (AA) and homozygous alleles for the inactivated form of the second gene (bb), wherein the homozygous alleles for the wild-type first gene (AA) are co-expressed with the first label, and wherein the homozygous alleles for the inactivated form of the second gene (bb) are co-expressed with the fourth label;

(d) a fourth genotype comprising one allele for the wild-type first gene (A), one allele for the inactivated version of the first gene (a), and homozygous alleles for the wild-type second gene (BB), wherein allele for the wild-type first gene (A) is co-expressed with the first label, the allele for the inactivated version of the first gene (a) is co-expressed with the second label, and the homozygous alleles for the wild-type second gene (BB) are co-expressed with the third label;

(e) a fifth genotype comprising one allele for the wild-type first gene (A), one allele for the inactivated version of the first gene (a), one allele for the wild-type second gene (B), and one allele for the inactivated form of the second gene (b), wherein the allele for the wild-type first gene (A) is co-expressed with the first label, the allele for the inactivated version of the first gene (a) is co-expressed second label, wherein the allele for the wild-type second gene (B) is co-expressed with the third label, and wherein the allele for the inactivated form of the second gene (b) is co-expressed with the fourth label;

(f) a sixth genotype comprising one allele for the wild-type first gene (A), one allele for the inactivated version of the first gene (a), and homozygous alleles for the inactivated version of the second gene (bb), wherein the allele for the wild-type first gene (A) is co-expressed with the first label, the allele for the inactivated version of the first gene (a) is co-expressed second label, and wherein the homozygous alleles for the inactivated form of the second gene (bb) are co-expressed with the fourth label;

(g) a seventh genotype comprising homozygous alleles for the inactivated version of the first gene (aa), and homozygous alleles for the wild-type second gene (BB), wherein the homozygous alleles for the inactivated version of the first gene (aa) are co-expressed with the second label, and wherein the homozygous alleles for the wild-type second gene (BB) are co-expressed with the third label;

(h) an eighth genotype comprising homozygous alleles for the inactivated version of the first gene (aa), one allele for the wild-type second gene (B), and one allele for the inactivated form of the second gene (b), wherein the homozygous alleles for the inactivated version of the first gene (aa) is co-expressed with the second label, the allele for the wild-type second gene (B) is co-expressed with the third label, and wherein the one allele for the inactivated form of the second gene (b) is co-expressed with the fourth label; and (i) a ninth genotype comprising homozygous alleles for the inactivated version of the first gene (aa), and homozygous alleles for the inactivated version of the second gene (bb), wherein the homozygous alleles for the inactivated version of the first gene (aa) is co-expressed with the second label, and wherein the homozygous alleles for the inactivated version of the second gene (bb) is co-expressed with the fourth label; and wherein said analyzing comprises measuring one or more of the first label, second label, third label, or fourth label (i.e., one, two, three, or all four labels).

We claim:

1. A transgenic, non-human animal whose genome comprises:

a first gene comprising an exon;

a second gene comprising an exon;

a first reporter gene and a second reporter gene integrated into the first gene, at positions flanking the exon of the first gene, wherein the first reporter gene and the second reporter gene are in opposite orientations, wherein the first reporter gene encodes a first fluorescent polypeptide label, and the second reporter gene encodes a second fluorescent polypeptide label;

a first recombinase target site and a second recombinase target site, in opposite orientation, and integrated into the first gene at positions flanking the first reporter gene and the second reporter gene, respectively;

a third reporter gene and a fourth reporter gene integrated into the second gene at positions flanking the exon of the second gene, wherein the third reporter gene and the fourth reporter gene are in opposite orientations, wherein the third reporter gene encodes a third fluorescent polypeptide label, and the fourth reporter gene encodes a fourth fluorescent polypeptide label, and wherein the first, second, third, and fourth fluorescent polypeptide labels are distinct from each other; and a third recombinase target site and a fourth recombinase target site, in opposite orientation, and integrated into the second gene at positions flanking the third reporter gene and the fourth reporter gene, respectively, and a nucleic acid sequence integrated at a separate locus, wherein the nucleic acid encodes an inducible recombinase.

2. The transgenic, non-human animal of claim 1, wherein the animal is a rodent.

3. The transgenic, non-human animal of claim 1, wherein the animal is a mouse.

4. The transgenic, non-human animal of claim 1, wherein the animal is further modified at the genetic or epigenetic level.

5. The transgenic, non-human animal of claim 1, wherein the first, second, third, and fourth recombinase target sites are loxP sites, and the inducible recombinase is a Cre recombinase.

6. The transgenic, non-human animal of claim 1, wherein the first, second, third, and fourth recombinase target sites are flippase recognition target (FRT) sites, and the inducible recombinase is a flippase (Flp) recombinase.

7. The transgenic, non-human animal of claim 1, wherein the first, second, third, and fourth recombinase target sites are attP and attB sites, and the inducible recombinase is a PhiC31 integrase.

8. The transgenic, non-human animal of claim 1, wherein the separate locus is a safe harbor site in the genome.

9. The transgenic, non-human animal of claim 1, wherein the animal is a mouse, and the safe harbor site is a ROSA26 locus.

10. The transgenic, non-human animal of claim 1, wherein the first, second, third, and fourth fluorescent polypeptide labels are each a distinct color selected from among the group consisting of red, blue, green, and purple.

11. A transgenic, mosaic non-human animal comprising nine populations of cells having nine distinct genotypes of two genes, wherein each population of the nine populations of cells has one of the nine distinct genotypes, wherein the animal is the result of expression of the inducible recombinase the animal of claim 1, and wherein the nine distinct genotypes comprise:

(a) a first genotype comprising homozygous alleles for a wild-type first gene (AA) and homozygous alleles for a wild-type second gene (BB), wherein the wild-type first gene (A) is operably linked with a reporter gene encoding a first fluorescent polypeptide label and the wild-type second gene (B) is operably linked with a reporter gene encoding a third fluorescent polypeptide label;

(b) a second genotype comprising homozygous alleles for the wild-type first gene (AA), one allele for the wild-type second gene (B), and one allele for an inactivated form of the second gene (b), wherein the first gene (A) is operably linked with the reporter gene encoding the first fluorescent polypeptide label, the second gene (B) is operably linked with the reporter gene encoding the third fluorescent polypeptide label, and wherein the allele for the inactivated form of the second gene (b) is operably linked with a reporter gene encoding a fourth fluorescent polypeptide label;

(c) a third genotype comprising homozygous alleles for the wild-type first gene (AA) and homozygous alleles for an inactivated form of the second gene (bb), wherein the homozygous alleles for the wild-type first gene (AA) are operably linked with the reporter gene encoding the first fluorescent polypeptide label, and wherein the homozygous alleles for the inactivated form of the second gene (bb) are operably linked with the reporter gene encoding the fourth fluorescent polypeptide label;

(d) a fourth genotype comprising one allele for the wild-type first gene (A), one allele for the inactivated version of the first gene (a), and homozygous alleles for the wild-type second gene (BB), wherein the allele for the wild-type first gene (A) is operably linked with the reporter gene encoding the first fluorescent polypeptide label, the allele for the inactivated version of the first gene (a) is operably linked with the second fluorescent polypeptide label, and the homozygous alleles for the wild-type second gene (BB) are operably linked with a reporter gene encoding a third fluorescent polypeptide label;

(e) a fifth genotype comprising one allele for the wild-type first gene (A), one allele for the inactivated version of the first gene (a), one allele for the wild-type second gene (B), and one allele for the inactivated form of the second gene (b), wherein the allele for the wild-type first gene (A) is operably linked with the reporter gene encoding the first fluorescent polypeptide label, the allele for the inactivated version of the first gene (a) is operably linked with the reporter gene encoding the second fluorescent polypeptide label, wherein the allele for the wild-type second gene (B) is operably linked with the reporter gene encoding the third fluorescent polypeptide label, and wherein the allele for the inactivated form of the second gene (b) is operably linked with the reporter gene encoding the fourth fluorescent polypeptide label;

(f) a sixth genotype comprising one allele for the wild-type first gene (A), one allele for the inactivated version of the first gene (a), and homozygous alleles for the inactivated version of the second gene (bb), wherein the allele for the wild-type first gene (A) is operably linked with the reporter gene encoding the first fluorescent polypeptide label, the allele for the inactivated version of the first gene (a) is operably linked with the reporter gene encoding the second fluorescent polypeptide label, and wherein the homozygous alleles for the inactivated form of the second gene (bb) are operably linked with the reporter gene encoding the fourth fluorescent polypeptide label;

(g) a seventh genotype comprising homozygous alleles for the inactivated version of the first gene (aa), and homozygous alleles for the wild-type second gene (BB), wherein the homozygous alleles for the inactivated version of the first gene (aa) are operably linked with the reporter gene encoding the second fluorescent polypeptide label, and wherein the homozygous alleles for the wild-type second gene (BB) are operably linked with the reporter gene encoding the third fluorescent polypeptide label;

(h) an eighth genotype comprising homozygous alleles for the inactivated version of the first gene (aa), one allele for the wild-type second gene (B), and one allele for the inactivated form of the second gene (b), wherein the homozygous alleles for the inactivated version of the first gene (aa) are operably linked with the reporter gene encoding the second fluorescent polypeptide label, the allele for the wild-type second gene (B) is operably linked with the reporter gene encoding the third fluorescent polypeptide label, and wherein the one allele for the inactivated form of the second gene (b) is operably linked with the reporter gene encoding the fourth fluorescent polypeptide label; and (i) a ninth genotype comprising homozygous alleles for the inactivated version of the first gene (aa), and homozygous alleles for the inactivated version of the second gene (bb), wherein the homozygous alleles for the inactivated version of the first gene (aa) is operabiy linked with the reporter gene encoding the second fluorescent polypeptide label, and wherein the homozygous alleles for the inactivated version of the second gene (bb) are operably linked with the fourth fluorescent polypeptide label, and wherein the first, second, third, and fourth fluorescent polypeptide labels are distinct from each other.

12. The transgenic, mosaic non-human animal of claim 11, wherein the inducible recombinase is a Cre recombinase, a flippase (Flp) recombinase, or a PhiC31 integrase.

13. The transgenic, mosaic non-human animal of claim 11, wherein the animal is a rodent.

14. The transgenic, mosaic non-human animal of claim 11, wherein the animal is a mouse.

15. The transgenic, mosaic non-human animal of claim 11, wherein the nucleic acid sequence encoding an inducible recombinase is integrated at a safe harbor site in the genome.

16. The transgenic, mosaic non-human animal of claim 15, wherein the animal is a mouse, and the safe harbor site is a ROSA26 locus.

17. The transgenic, mosaic non-human animal of claim 11, wherein the first, second, third, and fourth fluorescent polypeptide labels are each a distinct color selected from among the group consisting of red, blue, green, and purple.

18. The transgenic, mosaic non-human animal of claim 11, wherein the animal is further modified at the genetic or epigenetic level.

19. A composition comprising cells from among one or more of the populations of cells obtained from the non-human animal of claim 11.

* * * * *

SEQUENCE LISTING

```
<160> NUMBER OF SEQ ID NOS: 31

<210> SEQ ID NO 1
<211> LENGTH: 9900
<212> TYPE: DNA
<213> ORGANISM: Mus musculus

<400> SEQUENCE: 1
atctccgccg ccacctccgt ctcgctgcgc cccggcgggg gtgaggacga ggccggagtc      60
tccgggcttt ggcgttgttg tcagcctccg ggagagagat tggacaaata gtctccaaga     120
ggaggagggc gacgaccaag gactttcctg ctttttttggg tttctccgca agttggaaca    180
gagacccttt ttggtttagc gtttgcgtgt gtgttggtgc ctcttctccg tgcagcgact     240
gctggcccag ggtgactctg acttgtcctt tctcgtgaac tagtcatggc tagtgaagac     300
aatcgtgccc cttcccggcc accaacaggt gatgacgggg gaggtggagg gaaagaagaa     360
```

```
accctacgg aaggggtgc gctgtctctg aagccggggc tccccatcag gggcatcaga    420
atgaaattcg ccgtgctgac gggggttggtt gaagttggaa aagtgtccaa tagggatatt   480
gtagaaactg tctttaacct gctggtagga ggccagtttg atttggagat gaacttcatt   540
atccaggaag gtgagagcat tatgtgcatg gtggagctac tggaaaagtg tgatgtcact   600
tgccaagcag aagtctggag catgtttaca gccattctga agaagagcat acgaaatctt   660
caagtctgca cagaagtagg cctcgtggaa aaagtacttg ggaaaattga aaagttgac    720
agtatgattg cagatcttct cgttgacatg ttgggagtgc tggccagcta atttgaca     780
gttagagaac taaagctttt cttcagtaaa cttcaaggag ataaaggaca atggcctcct   840
cacgctggga agctgctgtc agtgttaaag cacatgcctc agaagtacgg tcctgacgcc   900
tttttcaact ttccaggaaa gagcgctgca gctattgcat tacctcctat agccagatgg   960
ccttaccaga atggttttac atttcacacc tggcttagaa tggatcctgt aaataatatt  1020
aatgttgaca aggataaacc atatttgtat tgtttcagaa ccagcaaagg tcttggctat  1080
tctgctcatt ttgttggagg ctgtttgatt ataacctcaa taaagtcaaa aggaaaaggc  1140
ttccaacatt gtgtgaaatt tgatttcaag ccacaaaagt ggtacatggt aactatagta  1200
cacatttata accggtggaa gaacagtgag cttcgctgtt acgtgaatgg ggaacttgct  1260
tcctatggag agataacatg gtttgtcaac ccagtgata cctttgacaa atgcttcctg    1320
ggatcatcgg agacagcgga tgcgaatcgg gtgttctgtg ccagatgac tgcggtttac    1380
ctgttcagtg atgctcttaa tgcagctcag atttttgcca tttatcagtt gggcctgggg  1440
tacaagggca catttaaatt taaagcagaa agtgacccttt cctcgctga gcaccataaa  1500
ctgttactgt atgacggcaa gctgtccagt gccattgcct tcacgtacaa cccgcgggcc  1560
acagatgccc agctgtgcct ggagtcgtct cccaaggaca cccctccat cttcgtccac  1620
tcgccacacg cactcatgct ccaggatgta aaggcagttt tgacacattc catccagagc  1680
gccatgcact ccataggagg agtacaagtt ctgtttccgc tcttcgccca gctggactac  1740
aagcaatatt tatctgatga ggttgacttg actatctgta caaccttgct ggcctttatc  1800
atggagttgc tgaagaactc aattgctatg caggagcaga tgcttgcttg taagggctttt  1860
ttggtaatag gttatagcct tgaaaagtct tccaaatccc acgtcagcag agcagtactt  1920
gaactttgcc ttgcgttttc aaagtatttg agcaatctgc agaatgggat gccctcctg    1980
aaacagctgt gtgatcacat tcttcttaac cctgctgtat ggatccacac tccagccaag  2040
gttcagttga tgctttatac ttatctatcc actgagttca ttgggacggt caacatctat  2100
aacactattc ggagagttgg aacagtgctg ctcatcatgc acacgctcaa gtactactac  2160
tgggcagtga atcctcagga ccgaagtggt atcaccccca aaggattaga tggaccaaga  2220
cccaatcaga aagaaatact ttctctgcga gcattcttac tgatgttcat taagcagtta  2280
gtgatgaagg actctggagt gaaggaagat gagctacagg ccattcttaa ctacctgctg  2340
actatgcatg aggacgacaa tctaatggat gtcctacagc tgcttgttgc gttgatggcg  2400
gagcatccta actccatgat tccggctttt gaccaaagga atgggctgcg tgttatctat  2460
aaacttctgg catcgaagag cgaaggaatc cgagtgcagc cactcaaggc actgggatac  2520
tttttaaagc atctggcgcc aaagagaaaa gctgaagtca tgcttgggca tggattgttc  2580
tcgctgctag ctgagagact tatgcttcag acaaatctaa tcacaatgac catgtataat  2640
gttctgtttg agattcttat agaacagatc tgtactcagg tgatccacaa acagcatcca  2700
```

```
gatcccgatt ctacagtaaa aatacaaaac cctcagatac taaaagtaat tgcgacccta   2760
cttcgaaatt ctccccagtg cccagagagc atggaggttc gccgagcatt tctttctgac   2820
atgattaaac tttttaataa cagtagagaa aacaggagga gcttgctgca gtgctctgtg   2880
tggcaagaat ggatgctttc tctctgctat tttaatccta agaattcaga tgagcaaaag   2940
ataacagaga tggtgtacgc catattcaga attctgcttt accatgcagt caaatacgag   3000
tggggtggct ggcgagtgtg ggtagacacc ttatccatca cacattcaaa ggttactttt   3060
gaaatacaca agaaaaacct tgccaatata tttagggaag agcagcggaa aggtgatgaa   3120
gaaacaggac cgtgttcttc aagcctggtt ccagaaggca ctggtgctac taggggtgtt   3180
gatgtttcag tggggtccca gcacgaagat cggaaggatt ctcccatctc tcctcatttc   3240
actagaaata gtgatgagaa ctcaagtatt ggagggcaa gttcaataga ttctgcatcc    3300
aacactgaac tgcagacaca tgatatgtct agtgatgaaa agaaagtaga gcgagaaaat   3360
caagagttac tggatcaagc caccgtggaa gaaacagcta caaatggggc aaaagatgac   3420
ttagaaacgt cttctgatgc agcagagcca gtgactatta actctaattc tttgaaacca   3480
ggcaaagata cagtgaccat cagtgaagta agtgcttcca taagttctcc ctcagaagaa   3540
gatgctgcag agatgccaga attactgaaa aagtctggag tagaggaaga gaggatgat    3600 gactatgtgg aactgaaggt agaaggcagc cctactgagg aagctggtct gcccacagag   3660
ctccaaggtg agggtttgtc tgtagctgcc tctgaaggca gagaagaacc agatatgtgt   3720
ggtcatggct gtgaagttca gtggaagca cctattacta aaattcataa tgatcctgaa    3780
actacagatt ctgaggattc taggtttcca actgtggcca cagcagggtc tttagctacc   3840
tcatcagaag ttcctgttcc ccaggcaact gtacagtcag acagccatga gatgctggat   3900
ggagggatga aagcaactaa ccttgccgga gaaactgagt cagttagtga ttgtgctgat   3960
aatgtctctg aggctcctgc cacttctgag cagaagatta ccaaactgga tgtttctagt   4020
gtggcttcag atactgagag gtttgaattg aaggccagta cgagcacaga agcaccacag   4080
cctcaacgac atgggcttga gatatcaagg caacaggagc agacagcaca aggaacagca   4140
ccagatgcag tagaccaaca aaggagggac tccagatcca ccatgtttcg cattcctgag   4200
ttcaagtggt ctcagatgca tcaacgtctg ctcactgatc tcttattttc catagaaaca   4260
gatatacaga tgtggagaag ccattcaaca aagacagtta tggacttcgt gaatagcagt   4320
gataatgtca tctttgtgca caacacaatt catctcatct ctcaagtgat ggacaatatg   4380
gtcatggctt gtgggggtat actgccatta ctctcagctg ctacctcggc cacacatgag   4440
ctggagaaca ttgagcctac tcaaggcctt tcaatagaag cctcagtgac atttcttcag   4500
aggctaatta gccttgtgga tgtgcttata tttgcaagtt ctcttggttt tactgaaatt   4560
gaagctgaaa aaatatgtc atctggagga attctgcgac agtgtctccg attggtgtgt    4620
gcagtagctg taaggaattg cttagagtgt cagcaacatt cacagctgaa agccagagga   4680
gatacagcaa agagctcgaa aacaatacat agcctgattc ccatgggaa atctgcagca    4740 aagagcccag tagacattgt gactggtggt atatctccgg taagagatct tgacaggctc   4800
ctgcaagaca tggacattaa tcggcttcga gcagttgttt tcagagacat cgaggacagc   4860
aagcaagctc aattcttggc tttggctgtt gtgtacttta tctctgttct gatggtctca   4920
aagtacagag acattttgga accccaagat gaaagacaca gtcagtctct taaggaaact   4980
agtagtgata atgggaatgc atcacttcct gatgcagaaa acacaccagc agaatttagt   5040 tcttttaactc tgtcgtcggt ggaagaatca ttggaaggca cctcatgcac tcgcaggagg   5100
```

```
gactcaggcc ttggtgagga aacagcctct ggcttaggaa gcggtctgtc tgtcgcttct    5160
ccagcggcgc ctctgggtgt cagcgcgggg ccagatgcca tcagcgaggt gctgtgcact    5220 cttctttgg aagtcaataa atctcaggaa acaagaattg atggaggaaa cgagttggac     5280
aggaaggtga caccatcagt cccagtttca aaaaatgtca acgtgaagga cattctccgg    5340
agcttggtga atatgccagc agatggagtc acagtggatc cagcccttct gcccccagcc    5400
tgccttggtg ctcttggaga tctgtctgtt gacccaccca tgcagttcag atcctttgac    5460
agaagtgtca tcattgcaac aaagaaatca tcagtcttac cttccgccct tactacaagt    5520
gcacctagta gcgccgtcag tgtggtgtct tcagtagatc ccacccacgc ctcagacacc    5580
ggaggagagt caccaggaag tagatctcct aatgcaaaac tgccctcagt tgcagcagtt    5640
ggctccgtcc cacaagaccc agctgcacac atgagtatta cagaaaggct agagcatgca    5700
ctggagaagg cagctcctct gctccgagag attttgtgg attttgcacc tttcctttct    5760
cggacacttt taggtagtca tggacaagaa ctgctgatag aaggaacaag cctggtctgc    5820
atgaagtcca gcagttcagt tgtggagctg gtcatgctgc tgtgttccca ggagtggcag    5880
aattctattc agaagaatgc aggccttgct tttattgaac ttgtcaatga aggaaggtta    5940
cttagccaaa caatgaagga tcatttagta agagtagcaa atgaagccga atttatcctg    6000
agcaggcaga gagcagagga tattcacaga catgcagaat ttgagtcatt gtgtgctcaa    6060
tactctgcag acaaaagaga agaggagaag atgtgtgatc atttgataag agcagctaaa    6120
tatcgagacc atgtgaccgc aactcagtta atccagaaaa ttatcaacct cctcacagac    6180
aagcatggag cctgggggag ctctgcagta agtcgtcctc gtgagttctg gcgccttgac    6240
tactgggaag atgacttgag gcgccggcga cgatttgtgc gtaaccctct aggatcgaca    6300
catcctgaag cgacactaaa aacagccgtg gaacatgctg cagatgaaga catccttgct    6360
aaaggaaaac agtccatcaa gagtcaggct ttaggaaatc agaactctga aaacgaggcc    6420
ctcctggaag gcgacgacga tactctgtca tccgtggatg agaaagattt agagaatctt    6480
gccggtcctg ttagcctgag cacccccagct cagcttgtgg cccctctgt tgtagtaaaa    6540 ggcactctct ctgtcacttc ctctgaactc tattttgagg tggatgaaga ggatcccaac    6600
ttcaagaaaa ttgacccaaa gatcttggca tatacagaag gtctgcatgg aaaatggctg    6660
ttcacagaga taagatcaat cttttctcgc cgttatcttt tgcaaaatac agctctggag    6720
atctttatgg caaacagagt tgctgtaatg ttcaacttcc cagaccctgc cacagtaaag    6780 aaaagtggtga actatctacc tcgtgttggt gtgggaacca gttttggatt acctcagacc    6840
aggcgtattt cattagccac tccacgtcag ctattcaaag cttcaaatat gactcagcgg    6900
tggcagcaca gagagatttc aaacttcgag tacttgatgt ttctcaacac aatagcaggg    6960
cggagttata atgacctaaa tcagtatcct gtgtttccct gggtcatcac taattatgag    7020
tcagaagaat tagatcttac cttgccaagc aatttcagag atttgtccaa gccaatagga    7080
gctttgaatc ccaaacgagc agcattcttt gcagagcgat ttgagtcatg ggaagatgat    7140
caagttccaa agttccacta tggtactcat tactcaactg caagttttgt tcttgcgtgg    7200
cttctaagaa tagaacctt tacaacttac tttctaaatt tacaaggagg gaaatttgat    7260
catgcagata ggacgttctc ctcagtctcc agagcatggc gaaacagtca gcgcgacaca    7320
tctgacatta aggaattgat tcctgaattt tattatctcc ctgagatgtt tgtcaacttc    7380
aataattata accttggagt gatggatgat gggacagtgg tgtctgatgt tgaacttcct    7440
```

```
ccttgggcca aaacctcgga agaattcgtt cgcataaaca gactggccct ggagagtgaa   7500
tttgtttcct gccagcttca ccaatggatt gatcttattt ttggctataa acaacaagga   7560
ccagaggcag tgcgagccct caatgtgttc tattacctaa cctatgaagg agctgtcaac   7620
ctgaactcaa taactgatcc tgtgctgaga gaggctgtgg aagctcagat ccgaagtttt   7680
ggacagacgc cttcgcaact gctcatagag ccccaccctc cccgaggttc ggccatgcag   7740
gcgagtccat tgatgttcac agaccaagcc cagcaagatg tcatcatggt cctaaagttc   7800
ccttcgaatt ctccagtcac ccacgttgcg gccaacaccc agccaggcct ggcaatgcct   7860
gctgtcatca ctgtcactgc taacaggctc tttgccgtga acaagtggca caaccttcct   7920
gctcaccaag gtgctgtaca agaccagcca taccagctgc cagtggaaat cgatcctctc   7980
atagcctgcg gcacagggac acacaggagg caggtaacag acctcctgga ccagagcatc   8040
caagtgcact cccagtgctt cgtcatcact tccgacaacc gctacattct cgtctgtggc   8100
ttctgggata gagtttccg ggtctactcc acagatacag gaaaattgat ccaagtggtg   8160
tttggccatt gggatgttgt cacttgccta gctcgctctg agtcgtacat aggggggaaat   8220 tgttacatcc tctcggggtc acgtgacgca actcttcttc tgtggtactg gaatgggaag   8280
agcagcggga ttggagataa ccctggcggt gaaactgcca ccctcgggc cattctcaca   8340 ggccatgact acgagatcac ctgtgctgct gtctgcgctg agctgggcct ggtgttaagt   8400
ggttcccaag aagggccgtg tctcatacac tccatgaatg agacctgtt aaggactttg   8460 gagggtcccg aaaattgcct gaaaccaaaa ctcatccaag catcgagaga gggtcactgt   8520
gtcatcttct atgaaaacgg ctgcttctgc accttcagtg tgaacgggaa gctgcaggcc   8580
accgtggaga cggatgatca cataagggcc atacagctga gcagagatgg gcagtacctg   8640
ctcacaggag gagacaacgg ggtggtgata gtgcggcagg tgtctgacct caagcagctc   8700
tttgcctacc caggctgtga tgctggaatc cgggccatgg ccctttcttt tgaccagagg   8760
tgcatcattt ctggaatggc ttcgggaagc attgtcctgt tttacaatga ctttaaccgc   8820
tggcatcatg agtaccagac ccgctactga ggggaacgaa tgcaccgtgg tcctgtttca   8880
gcccaagcaa ggaaggactt caaacaccac tctatagaaa tagctatcac atctgaatgt   8940
aacttaaatt tgcttgaaca agcaaaatat ttttttaaagt taattgctat ttttgtagac   9000
tttgctcgac atttttgggg gggggggggt gggaacagca caagcaggga actggctgct   9060
gggttctgta gtttacaaaa tctatatttt tagtcctaat gaaaagtcta ttttcaccaa   9120
ttatggatac agacagtgga accaataatc ccactaattc ttgctacatg tgaaaaacca   9180
tttcccactt atctgtaatc ttaagaaata tgattttagc aatagggaaa tgggttcaaa   9240
tgggggacag ggaaatttat tctgtactgg gtcctgtatt tttctagaca attgtgcttc   9300
ttcagtgctg acatttctag ggtttttaata gtaatgttta aattatgacg tgtaatttaa   9360
aacatctcag tgaattattt ctgtattatt ccccttcaag catgtgttag acctagaaaa   9420
ttatggttta gggaggctac tttattttac tgtgtgttaa acagcaaaga tctaagttta   9480
tcaatcataa atactgcttt tcctgatctg ccgtcctcat ggcagagagt ggaatgatgg   9540
gaccgctctt gggctcgcaa ccttttaagc actacagcct gcccgaggcc accagtgccc   9600
tgctaagcca gagccaggtg ggccactccc catgtccact ggcccacagt cctgtctcaa   9660
gatcagaggc gaccaggtac tgtgtaagca gcacccacct taccectatt tgttatgaag   9720 ctatctttac cttcctttg actagtaatt tgtatcaaga aaatgttatt ttggtgtcat   9780
ataattctac ttttttctagt agattgcttt atggaattct gtgaaaatat ttgagcagag   9840
```
gtctgtatta cataaataaa ttctttgtat gttgtgaact tgaaaaaaaa aaaaaaaaaa    9900

<210> SEQ ID NO 2
<211> LENGTH: 9387
<212> TYPE: DNA
<213> ORGANISM: Mus musculus

<400> SEQUENCE: 2
atctccgccg ccacctccgt ctcgctgcgc cccggcgggg gtgaggacga ggccggagtc      60
tccgggcttt ggcgttgttg tcagcctccg ggagagagat tggacaaata gtctccaaga     120
ggaggagggc gacgaccaag gactttcctg ctttttggg tttctccgca agttggaaca      180
gagacccttt ttggtttagc gtttgcgtgt gtgttggtgc ctcttctccg tgcagcgact     240
gctggcccag ggtgactctg acttgtcctt tctcgtgaac tagtcatggc tagtgaagac     300
aatcgtgccc cttcccggcc accaacaggt gatgacgggg gaggtggagg gaaagaagaa     360
acccctacgg aaggggtgc gctgtctctg aagccgggc tccccatcag ggcatcaga      420 atgaaattcg ccgtgctgac ggggttggtt gaagttggag aagtgtccaa tagggatatt     480
gtagaaactg tctttaacct gctggtagga ggccagtttg atttggagat gaacttcatt     540
atccaggaag gtgagagcat tatgtgcatg gtggagctac tggaaaagtg tgatgtcact     600
tgccaagcag aagtctggag catgtttaca gccattctga agaagagcat acgaaatctt     660
caagtctgca cagaagtagg cctcgtggaa aaagtacttg ggaaaattga aaagttgac     720 agtatgattg cagatcttct cgttgacatg ttgggagtgc tggccagcta aatttgaca      780 gttagagaac taaagctttt cttcagtaaa cttcaaggag ataaaggaca atggcctcct     840
cacgctggga agctgctgtc agtgttaaag cacatgcctc agaagtacgg tcctgacgcc     900 ttttcaact ttccaggaaa gagcgctgca gctattgcat tacctcctat agccagatgg      960
ccttaccaga atggttttac atttcacacc tggcttagaa tggatcctgt aaataatatt    1020
aatgttgaca aggataaacc atatttgtat tgtttcagaa ccagcaaagg tcttggctat    1080
tctgctcatt ttgttggagg ctgtttgatt ataacctcaa taaagtcaaa aggaaaaggc    1140
ttccaacatt gtgtgaaatt tgatttcaag ccacaaaagt ggtacatggt aactatagta    1200
cacatttata accggtggaa gaacagtgag cttcgctgtt acgtgaatgg ggaacttgct    1260
tcctatggag agataacatg gtttgtcaac accagtgata cctttgacaa atgcttcctg    1320
ggatcatcgg agacagcgga tgcgaatcgg gtgttctgtg ccagatgac tgcggtttac    1380 ctgttcagtg atgctcttaa tgcagctcag atttttgcca tttatcagtt gggcctgggg    1440
tacaagggca catttaaatt taaagcagaa agtgacctt tcctcgctga gcaccataaa     1500
ctgttactgt atgacggcaa gctgtccagt gccattgcct tcacgtacaa cccgcgggcc    1560
acagatgccc agctgtgcct ggagtcgtct cccaaggaca accctccat cttcgtccac      1620 tcgccacacg cactcatgct ccaggatgta aaggcagttt tgacacattc catccagagc    1680
gccatgcact ccataggagg agtacaagtt ctgtttccgc tcttcgccca gctggactac    1740
aagcaatatt tatctgatga ggttgacttg actatctgta caaccttgct ggcctttatc    1800
atggagttgc tgaagaactc aattgctatg caggagcaga tgcttgcttg taagggcttt    1860
ttggtaatag gttatagcct tgaaaagtct tccaaatccc acgtcagcag agcagtactt    1920
gaactttgcc ttgcgttttc aaagtatttg agcaatctgc agaatgggat gcccctcctg    1980
aaacagctgt gtgatcacat tcttcttaac cctgctgtat ggatccacac tccagccaag    2040

```
gttcagttga tgctttatac ttatctatcc actgagttca ttgggacggt caacatctat      2100
aacactattc ggagagttgg aacagtgctg ctcatcatgc acacgctcaa gtactactac      2160
tgggcagtga atcctcagga ccgaagtggt atcaccccca aaggattaga tggaccaaga      2220
cccaatcaga aagaaatact ttctctgcga gcattcttac tgatgttcat taagcagtta      2280
gtgatgaagg actctggagt gaaggaagat gagctacagg ccattcttaa ctacctgctg      2340
actatgcatg aggacgacaa tctaatggat gtcctacagc tgcttgttgc gttgatggcg      2400
gagcatccta actccatgat tccggctttt gaccaaagga atgggctgcg tgttatctat      2460
aaacttctgg catcgaagag cgaaggaatc cgagtgcagg cactcaaggc actgggatac      2520
tttttaaagc atctggcgcc aaagagaaaa gctgaagtca tgcttgggca tggattgttc      2580
tcgctgctag ctgagagact tatgcttcag acaaatctaa tcacaatgac catgtataat      2640
gttctgtttg agattcttat agaacagatc tgtactcagg tgatccacaa acagcatcca      2700
gatcccgatt ctacagtaaa aatacaaaac cctcagatac taaaagtaat tgcgacccta      2760
cttcgaaatt ctccccagtg cccagagagc atggaggttc gccgagcatt tctttctgac      2820
atgattaaac ttttttaataa cagtagagaa aacaggagga gcttgctgca gtgctctgtg      2880
tggcaagaat ggatgctttc tctctgctat tttaatccta agaattcaga tgagcaaaag      2940
ataacagaga tggtgtacgc catattcaga attctgcttt accatgcagt caaatacgag      3000
tggggtggct ggcgagtgtg ggtagacacc ttatccatca cacattcaaa ggttactttt      3060
gaaatacaca aagaaaacct tgccaatata tttagggaag agcagcggaa aggtgatgaa      3120
gaaacaggac cgtgttcttc aagcctggtt ccagaaggca ctggtgctac tagggggtgtt     3180 gatgtttcag tggggtccca gcacgaagat cggaaggatt ctcccatctc tcctcatttc      3240
actagaaata gtgatgagaa ctcaagtatt ggagggcaa gttcaataga ttctgcatcc       3300
aacactgaac tgcagacaca tgatatgtct agtgatgaaa agaaagtaga gcgagaaaat      3360
caagagttac tggatcaagc caccgtggaa gaaacagcta caaatggggc aaaagatgac      3420
ttagaaacgt cttctgatgc agcagagcca gtgactatta actctaattc tttggaacca      3480
ggcaaagata cagtgaccat cagtgaagta agtgcttcca taagttctcc ctcagaagaa      3540
gatgctgcag agatgccaga attactggaa aagtctggag tagaggaaga agaggatgat      3600
gactatgtgg aactgaaggt agaaggcagc cctactgagg aagctggtct gcccacagag      3660
ctccaaggtg agggtttgtc tgtagctgcc tctgaaggca gagaagaacc agatatgtgt      3720
ggtcatggct gtgaagttca agtggaagca cctattacta aaattcataa tgatcctgaa      3780
actacagatt ctgaggattc taggtttcca actgtggcca cagcagggtc tttagctacc      3840
tcatcagaag ttcctgttcc ccaggcaact gtacagtcag acagccatga gatgctggat      3900
ggagggatga aagcaactaa ccttgccgga gaaactgagt cagttagtga ttgtgctgat      3960
aatgtctctg aggctcctgc cacttctgag cagaagatta ccaaactgga tgtttctagt      4020
gtggcttcag atactgagag gtttgaattg aaggccagta cgagcacaga agcaccacag      4080
cctcaacgac atgggcttga gatatcaagg caacaggagc agacagcaca aggaacagca      4140
ccagatgcag tagaccaaca aaggagggac tccagatcca ccatgtttcg cattcctgag      4200
ttcaagtggt ctcagatgca tcaacgtctg ctcactgatc tcttattttc catagaaaca      4260
gatatacaga tgtgggagaag ccattcaaca aagacagtta tggacttcgt gaatagcagt     4320
gataatgtca tctttgtgca caacacaatt catctcatct ctcaagtgat ggacaatatg      4380
gtcatggctt gtggggggtat actgccatta ctctcagctg ctacctcggc cacacatgag     4440
```

```
ctggagaaca ttgagcctac tcaaggcctt tcaatagaag cctcagtgac atttcttcag    4500
aggctaatta gccttgtgga tgtgcttata tttgcaagtt ctcttggttt tactgaaatt    4560
gaagctgaaa aaatatgtc atctggagga attctgcgac agtgtctccg attggtgtgt    4620
gcagtagctg taaggaattg cttagagtgt cagcaacatt cacagctgaa agccagagga    4680
gatacagcaa agagctcgaa aacaatacat agcctgattc ccatggggaa atctgcagca    4740
aagagcccag tagacattgt gactggtggt atatctccgg taagagatct tgacaggctc    4800
ctgcaagaca tggacattaa tcggcttcga gcagttgttt tcagagacat cgaggacagc    4860
aagcaagctc aattcttggc tttggctgtt gtgtacttta tctctgttct gatggtctca    4920
aagtacagag acattttgga accccaagat gaaagacaca gtcagtctct taaggaaact    4980
agtagtgata tgggaatgc atcacttcct gatgcagaaa acacaccagc agaatttagt    5040
tctttaactc tgtcgtcggt ggaagaatca ttggaaggca cctcatgcac tcgcaggagg    5100
gactcaggcc ttggtgagga acagcctct ggcttaggaa gcggtctgtc tgtcgcttct    5160
ccagcggcgc ctctgggtgt cagcgcgggg ccagatgcca tcagcgaggt gctgtgcact    5220 cttctttgg aagtcaataa atctcaggaa acaagaattg atggaggaaa cgagttggac    5280
aggaaggtga caccatcagt cccagtttca aaaaatgtca acgtgaagga cattctccgg    5340
agcttggtga atatgccagc agatggagtc acagtggatc cagcccttct gcccccagcc    5400
tgccttggtg ctcttggaga tctgtctgtt gacccaccca tgcagttcag atcctttgac    5460
agaagtgtca tcattgcaac aaagaaatca tcagtcttac cttccgccct tactacaagt    5520
gcacctagta gcgccgtcag tgtggtgtct tcagtagatc ccacccacgc ctcagacacc    5580
ggaggagagt caccaggaag tagatctcct aatgcaaaac tgccctcagt tgcagcagtt    5640
ggctccgtcc cacaagaccc agctgcacac atgagtatta cagaaaggct agagcatgca    5700
ctggagaagg cagctcctct gctccgagag atttttgtgg attttgcacc tttcctttct    5760
cggacacttt taggtagtca tggacaagaa ctgctgatag aaggaacaag cctggtctgc    5820
atgaagtcca gcagttcagt tgtggagctg gtcatgctgc tgtgttccca ggagtggcag    5880
aattctattc agaagaatgc aggccttgct tttattgaac ttgtcaatga aggaaggtta    5940
cttagccaaa caatgaagga tcatttagta agagtagcaa atgaagccga atttatcctg    6000
agcaggcaga gagcagagga tattcacaga catgcagaat ttgagtcatt gtgtgctcaa    6060
tactctgcag acaaaagaga agaggagaag atgtgtgatc atttgataag agcagctaaa    6120
tatcgagacc atgtgaccgc aactcagtta atccagaaaa ttatcaacct cctcacagac    6180
aagcatggag cctggggag ctctgcagta agtcgtcctc gtgagttctg gcgccttgac    6240
tactgggaag atgacttgag gcgccggcga cgatttgtgc gtaaccctct aggatcgaca    6300
catcctgaag cgacactaaa aacagccgtg gaacatgctg cagatgaaga catccttgct    6360
aaaggaaaac agtccatcaa gagtcaggct ttaggaaatc agaactctga aaacgaggcc    6420
ctcctggaag gcgacgacga tactctgtca tccgtggatg agaaagattt agagaatctt    6480
gccggtcctg ttagcctgag cacccccagct cagcttgtgg cccctctgt tgtagtaaaa    6540 ggcactctct ctgtcacttc ctctgaactc tattttgagg tggatgaaga ggatcccaac    6600
ttcaagaaaa ttgacccaaa gatcttggca tatacagaag gtctgcatgg aaaatggctg    6660
ttcacagaga taagatcaat cttttctcgc cgttatcttt tgcaaaatac agctctggag    6720
atctttatgg caaacagagt tgctgtaatg ttcaacttcc cagaccctgc cacagtaaag    6780
```

| | |
|---|---|
| aaagtggtga actatctacc tcgtgttggt gtgggaacca gttttggatt acctcagacc | 6840 |
| aggcgtattt cattagccac tccacgtcag ctattcaaag cttcaaatat gactcagcgg | 6900 |
| tggcagcaca gagagatttc aaacttcgag tacttgatgt ttctcaacac aatagcaggg | 6960 |
| cggagttata atgacctaaa tcagtatcct gtgtttccct gggtcatcac taattatgag | 7020 |
| tcagaagaat tagatcttac cttgccaagc aatttcagag atttgtccaa gccaatagga | 7080 |
| gctttgaatc ccaaacgagc agcattcttt gcagagcgat ttgagtcatg gaagatgat | 7140 |
| caagttccaa agttccacta tggtactcat tactcaactg caagttttgt tcttgcgtgg | 7200 |
| cttctaagaa tagaaccttt tacaacttac tttctaaatt tacaaggagg gaaatttgat | 7260 |
| catgcagata ggacgttctc ctcagtctcc agagcatggc gaaacagtca gcgcgacaca | 7320 |
| tctgacatta aggaattgat tcctgaattt tattatctcc ctgagatgtt tgtcaacttc | 7380 |
| aataattata accttggagt gatggatgat gggacagtgg tgtctgatgt tgaacttcct | 7440 |
| ccttgggcca aaacctcgga agaattcgtt cgcataaaca gactggccct ggagagtgaa | 7500 |
| tttgtttcct gccagcttca ccaatggatt gatcttattt ttggctataa acaacaagga | 7560 |
| ccagaggcag tgcgagccct caatgtgttc tattacctaa cctatgaagg agctgtcaac | 7620 |
| ctgaactcaa taactgatcc tgtgctgaga gaggctgtgg aagctcagat ccgaagtttt | 7680 |
| ggacagacgc cttcgcaact gctcatagag ccccaccctc cccgaggttc ggccatgcag | 7740 |
| gcgagtccat tgatgttcac agaccaagcc cagcaagatg tcatcatggt cctaaagttc | 7800 |
| ccttcgaatt ctccagtcac ccacgttgcg gccaacaccc agccaggcct ggcaatgcct | 7860 |
| gctgtcatca ctgtcactgc taacaggctc tttgccgtga acaagtggca caaccttcct | 7920 |
| gctcaccaag gtgctgtaca agaccagcca taccagctgc cagtggaaat cgatcctctc | 7980 |
| atagcctgcg gcacagggac acacaggagg caggtaacag acctcctgga ccagagcatc | 8040 |
| caagtgcact cccagtgctt cgtcatcact tccgacaacc gctacattct cgtctgtggc | 8100 |
| ttctgggata gagtttccg ggtctactcc acagatacag gaaaattgat ccaagtggtg | 8160 |
| tttggccatt gggatgttgt cacttgccta gctcgctctg agtcgtacat aggggaaat | 8220 |
| tgttacatcc tctcggggtc acgtgacgca actcttcttc tgtggtactg gaatgggaag | 8280 |
| agcagcggga ttggagataa ccctggcggt gaaactgcca cccctcgggc cattctcaca | 8340 |
| ggccatgact acgagatcac ctgtgctgct gtctgcgctg agctgggcct ggtgttaagt | 8400 |
| ggttcccaag aagggccgtg tctcatacac tccatgaatg gagacctgtt aaggactttg | 8460 |
| gagggtcccg aaaattgcct gaaaccaaaa ctcatccaag catcgagaga gggtcactgt | 8520 |
| gtcatcttct atgaaaacgg ctgcttctgc accttcagtg tgaacgggaa gctgcaggcc | 8580 |
| accgtggaga cggatgatca cataagggtg agtgccgtag gctccacctt gttccttta | 8640 |
| ctgggaagct ctaagtaaag gataagttca ctgaagcagc ctaagtctga actagctggg | 8700 |
| gcctccgtcc catgccagag gggcagcact agctagcact tagaagccca gagcaccttg | 8760 |
| ctgcaggcta gtgccttcac tgtggccgtg tgcagagaac acccactgac tgatgtccca | 8820 |
| tagctgattc tagccatacc atttcctcta agtgctacct aacagcagac ccggctctaa | 8880 |
| gattcactgt acagcaaagc tgaactagat tctgcctaaa actgctttct cttcacattg | 8940 |
| gaaacggcag cacggagtcg ctgtgtattc ttggggtcag cagctaatag atatctgctc | 9000 |
| cgacctactg gagagcaaca ccaaagcaag tcatgttaga gacttgggtg tccaaatgac | 9060 |
| aggcgctgtt tcccctcctg tctgtaagga atgctaagct agtgggcagc acaggtcttg | 9120 |
| ccttgcttct caggccagcc cccaaggcgc tagacatagg ggggaagaga gccagggtgc | 9180 |

-continued

| | |
|---|---|
| tctttgggga taagctagga tgtccctgtc attttctaaa tggaaatgga agagccaagt | 9240 |
| gtggtggcac acgcctgtaa tcccagcaca tgggaagcat aggcagatgg atctccatga | 9300 |
| gttcaaagcc agcttggtct ataaagagaa ttccaagaca gccagtgctt cacagagaag | 9360 |
| ccctgtctca aaaacaaaa acaaaaa | 9387 |

<210> SEQ ID NO 3
<211> LENGTH: 8860
<212> TYPE: DNA
<213> ORGANISM: Mus musculus

<400> SEQUENCE: 3

| | |
|---|---|
| atctccgccg ccacctccgt ctcgctgcgc cccggcgggg gtgaggacga ggccggagtc | 60 |
| tccgggcttt ggcgttgttg tcagcctccg ggagagagat tggacaaata gtctccaaga | 120 |
| ggaggagggc gacgaccaag gactttcctg ctttttgggg tttctccgca agttggaaca | 180 |
| gagaccctt ttggtttagc gtttgcgtgt gtgttggtgc ctcttctccg tgcagcgact | 240 |
| gctggcccag ggtgactctg acttgtcctt tctcgtgaac tagtcatggc tagtgaagac | 300 |
| aatcgtgccc cttcccggcc accaacaggt gatgacgggg gaggtggagg gaaagaagaa | 360 |
| accccctacgg aaggggtgc gctgtctctg aagccgggc tccccatcag gggcatcaga | 420 |
| atgaaattcg ccgtgctgac ggggttggtt gaagttggag aagtgtccaa tagggatatt | 480 |
| gtagaaactg tctttaacct gctggtagga ggccagtttg atttggagat gaacttcatt | 540 |
| atccaggaag gtgagagcat tatgtgcatg gtggagctac tggaaaagtg tgatgtcact | 600 |
| tgccaagcag aagtctggag catgtttaca gccattctga agaagagcat acgaaatctt | 660 |
| caagtctgca cagaagtagg cctcgtggaa aaagtacttg ggaaaattga aaagttgac | 720 |
| agtatgattg cagatcttct cgttgacatg ttgggagtgc tggccagcta aatttgaca | 780 |
| gttagagaac taaagctttt cttcagtaaa cttcaaggag ataaaggaca atggcctcct | 840 |
| cacgctggga agctgctgtc agtgttaaag cacatgcctc agaagtacgg tcctgacgcc | 900 |
| tttttcaact ttccaggaaa gagcgctgca gctattgcat tacctcctat agccagatgg | 960 |
| ccttaccaga atggttttac atttcacacc tggcttagaa tggatcctgt aaataatatt | 1020 |
| aatgttgaca aggataaacc atatttgtat tgtttcagaa ccagcaaagg tcttggctat | 1080 |
| tctgctcatt tgttggagg ctgtttgatt ataacctcaa taaagtcaaa aggaaaaggc | 1140 |
| ttccaacatt gtgtgaaatt tgatttcaag ccacaaaagt ggtacatggt aactatagta | 1200 |
| cacatttata accggtggaa gaacagtgag cttcgctgtt acgtgaatgg ggaacttgct | 1260 |
| tcctatggag agataacatg gtttgtcaac accagtgata cctttgacaa atgcttcctg | 1320 |
| ggatcatcgg agacagcgga tgcgaatcgg gtgttctgtg gccagatgac tgcggtttac | 1380 |
| ctgttcagtg atgctcttaa tgcagctcag attttgcca tttatcagtt gggcctgggg | 1440 |
| tacaagggca catttaaatt taaagcagaa agtgacctt tcctcgctga gcaccataaa | 1500 |
| ctgttactgt atgacggcaa gctgtccagt gccattgcct tcacgtacaa cccgcgggcc | 1560 |
| acagatgccc agctgtgcct ggagtcgtct cccaaggaca accctccat cttcgtccac | 1620 |
| tcgccacacg cactcatgct ccaggatgta aaggcagttt tgacacattc catccagagc | 1680 |
| gccatgcact ccataggagg agtacaagtt ctgtttccgc tcttcgccca gctggactac | 1740 |
| aagcaatatt tatctgatga ggttgacttg actatctgta caaccttgct ggcctttatc | 1800 |
| atggagttgc tgaagaactc aattgctatg caggagcaga tgcttgcttg taagggcttt | 1860 |

```
ttggtaatag gttatagcct tgaaaagtct tccaaatccc acgtcagcag agcagtactt   1920
gaactttgcc ttgcgttttc aaagtatttg agcaatctgc agaatgggat gcccctcctg   1980
aaacagctgt gtgatcacat tcttcttaac cctgctgtat ggatccacac tccagccaag   2040
gttcagttga tgctttatac ttatctatcc actgagttca ttgggacggt caacatctat   2100
aacactattc ggagagttgg aacagtgctg ctcatcatgc acacgctcaa gtactactac   2160
tgggcagtga atcctcagga ccgaagtggt atcaccccca aaggattaga tggaccaaga   2220
cccaatcaga aagaaatact ttctctgcga gcattcttac tgatgttcat taagcagtta   2280
gtgatgaagg actctggagt gaaggaagat gagctacagg ccattcttaa ctacctgctg   2340
actatgcatg aggacgacaa tctaatggat gtcctacagc tgcttgttgc gttgatggcg   2400
gagcatccta actccatgat tccggctttt gaccaaagga atgggctgcg tgttatctat   2460
aaacttctgg catcgaagag cgaaggaatc cgagtgcagg cactcaaggc actgggatac   2520
tttttaaagc atctggcgcc aaagagaaaa gctgaagtca tgcttgggca tggattgttc   2580
tcgctgctag ctgagagact tatgcttcag acaaatctaa tcacaatgac catgtataat   2640
gttctgtttg agattcttat agaacagatc tgtactcagg tgatccacaa acagcatcca   2700
gatcccgatt ctacagtaaa aatacaaaac cctcagatac taaaagtaat tgcgacccta   2760
cttcgaaatt ctccccagtg cccagagagc atggaggttc gccgagcatt tctttctgac   2820
atgattaaac tttttaataa cagtagagaa acaggagga gcttgctgca gtgctctgtg   2880
tggcaagaat ggatgctttc tctctgctat tttaatccta agaattcaga tgagcaaaag   2940
ataacagaga tggtgtacgc catattcaga attctgcttt accatgcagt caaatacgag   3000
tggggtggct ggcgagtgtg ggtagacacc ttatccatca cacattcaaa ggttactttt   3060
gaaatacaca agaaaaacct tgccaatata tttaggaag agcagcggaa aggtgatgaa   3120
gaaacaggac cgtgttcttc aagcctggtt ccagaaggca ctggtgctac tagggtgtt   3180
gatgtttcag tggggtccca gcacgaagat cggaaggatt ctcccatctc tcctcatttc   3240
actagaaata gtgatgagaa ctcaagtatt gggagggcaa gttcaataga ttctgcatcc   3300
aacactgaac tgcagacaca tgatatgtct agtgatgaaa agaaagtaga gcgagaaaat   3360
caagagttac tggatcaagc caccgtggaa gaaacagcta caaatggggc aaaagatgac   3420
ttagaaacgt cttctgatgc agcagagcca gtgactatta actctaattc tttggaacca   3480
ggcaaagata cagtgaccat cagtgaagta agtgcttcca taagttctcc ctcagaagaa   3540
gatgctgcag agatgccaga attactgaa aagtctggag tagaggaaga agaggatgat   3600
gactatgtgg aactgaaggt agaaggcagc cctactgagg aagctggtct gcccacagag   3660
ctccaaggtg agggttttgtc tgtagctgcc tctgaaggca gagaagaacc agatatgtgt   3720
ggtcatggct gtgaagttca agtggaagca cctattacta aaattcataa tgatcctgaa   3780
actacagatt ctgaggattc taggtttcca actgtggcca cagcagggtc tttagctacc   3840
tcatcagaag ttcctgttcc ccaggcaact gtacagtcag acagccatga gatgctggat   3900
ggagggatga agcaactaa ccttgccgga gaaactgagt cagttagtga ttgtgctgat   3960
aatgtctctg aggctcctgc cacttctgag cagaagatta ccaaactgga tgtttctagt   4020
gtggcttcag atactgagag gtttgaattg aaggccagta cgagcacaga agcaccacag   4080
cctcaacgac atgggcttga gatatcaagg caacaggagc agacagcaca aggaacagca   4140
ccagatgcag tagaccaaca aaggagggac tccagatcca ccatgtttcg cattcctgag   4200
ttcaagtggt ctcagatgca tcaacgtctg ctcactgatc tcttattttc catagaaaca   4260
```

```
gatatacaga tgtggagaag ccattcaaca aagacagtta tggacttcgt gaatagcagt    4320
gataatgtca tctttgtgca caacacaatt catctcatct ctcaagtgat ggacaatatg    4380
gtcatggctt gtgggggtat actgccatta ctctcagctg ctacctcggc cacacatgag    4440
ctggagaaca ttgagcctac tcaaggcctt tcaatagaag cctcagtgac atttcttcag    4500
aggctaatta gccttgtgga tgtgcttata tttgcaagtt ctcttggttt tactgaaatt    4560
gaagctgaaa aaatatgtc atctggagga attctgcgac agtgtctccg attggtgtgt     4620
gcagtagctg taaggaattg cttagagtgt cagcaacatt cacagctgaa agccagagga    4680
gatacagcaa agagctcgaa aacaatacat agcctgattc ccatggggaa atctgcagca    4740
aagagcccag tagacattgt gactggtggt atatctccgg taagagatct tgacaggctc    4800
ctgcaagaca tggacattaa tcggcttcga gcagttgttt tcagagacat cgaggacagc    4860
aagcaagctc aattcttggc tttggctgtt gtgtacttta tctctgttct gatggtctca    4920
aagtacagag acattttgga accccaagat gaaagacaca gtcagtctct taaggaaact    4980
agtagtgata atgggaatgc atcacttcct gatgcagaaa acacaccagc agaatttagt    5040
tctttaactc tgtcgtcggt ggaagaatca ttggaaggca cctcatgcac tcgcaggagg    5100
gactcaggcc ttggtgagga aacagcctct ggcttaggaa gcggtctgtc tgtcgcttct    5160
ccagcggcgc ctctgggtgt cagcgcgggg ccagatgcca tcagcgaggt gctgtgcact    5220 cttctctttgg aagtcaataa atctcaggaa acaagaattg atggaggaaa cgagttggac   5280
aggaaggtga caccatcagt cccagtttca aaaaatgtca acgtgaagga cattctccgg    5340
agcttggtga atatgccagc agatggagtc acagtggatc cagcccttct gcccccagcc    5400
tgccttggtg ctcttggaga tctgtctgtt gacccaccca tgcagttcag atcctttgac    5460
agaagtgtca tcattgcaac aaagaaatca tcagtcttac cttccgccct tactacaagt    5520
gcacctagta gcgccgtcag tgtggtgtct tcagtagatc ccacccacgc ctcagacacc    5580
ggaggagagt caccaggaag tagatctcct aatgcaaaac tgccctcagt tgcagcagtt    5640
ggctccgtcc cacaagaccc agctgcacac atgagtatta cagaaaggct agagcatgca    5700
ctggagaagg cagctcctct gctccgagag atttttgtgg attttgcacc tttccttct    5760 cggacacttt taggtagtca tggacaagaa ctgctgatag aaggaacaag cctggtctgc    5820
atgaagtcca gcagttcagt tgtggagctg gtcatgctgc tgtgttccca ggagtggcag    5880
aattctattc agaagaatgc aggccttgct tttattgaac ttgtcaatga aggaaggtta    5940
cttagccaaa caatgaagga tcatttagta agagtagcaa atgaagccga atttatcctg    6000
agcaggcaga gagcagagga tattcacaga catgcagaat ttgagtcatt gtgtgctcaa    6060
tactctgcag acaaaagaga gaggagaag atgtgtgatc atttgataag agcagctaaa    6120
tatcgagacc atgtgaccgc aactcagtta atccagaaaa ttatcaacct cctcacagac    6180
aagcatggag cctgggggag ctctgcagta agtcgtcctc gtgagttctg cgccttgac    6240 tactgggaag atgacttgag gcgccggcga cgatttgtgc gtaaccctct aggatcgaca    6300
catcctgaag cgacactaaa aacagccgtg gaacatgctg cagatgaaga catccttgct    6360
aaaggaaaac agtccatcaa gagtcaggct ttaggaaatc agaactctga aaacgaggcc    6420
ctcctggaag gcgacgacga tactctgtca tccgtggatg agaaagattt agagaatctt    6480
gccggtcctg ttagcctgag cacccccagct cagcttgtgg ccccctctgt tgtagtaaaa    6540
ggcactctct ctgtcacttc ctctgaactc tattttgagg tggatgaaga ggatcccaac    6600
```

```
ttcaagaaaa ttgacccaaa gatcttggca tatacagaag gtctgcatgg aaaatggctg     6660
ttcacagaga taagatcaat cttttctcgc cgttatcttt tgcaaaatac agctctggag     6720
atctttatgg caaacagagt tgctgtaatg ttcaacttcc cagaccctgc cacagtaaag     6780
aaagtggtga actatctacc tcgtgttggt gtgggaacca gttttggatt acctcagacc     6840
aggcgtattt cattagccac tccacgtcag ctattcaaag cttcaaatat gactcagcgg     6900
tggcagcaca gagagatttc aaacttcgag tacttgatgt ttctcaacac aatagcaggg     6960
cggagttata atgacctaaa tcagtatcct gtgtttccct gggtcatcac taattatgag     7020
tcagaagaat tagatcttac cttgccaagc aatttcagag atttgtccaa gccaatagga     7080
gctttgaatc ccaaacgagc agcattcttt gcagagcgat ttgagtcatg ggaagatgat     7140
caagttccaa agttccacta tggtactcat tactcaactg caagttttgt tcttgcgtgg     7200
cttctaagaa tagaaccttt tacaacttac tttctaaatt tacaaggagg gaaatttgat     7260
catgcagata ggacgttctc ctcagtctcc agagcatggc gaaacagtca gcgcgacaca     7320
tctgacatta aggaattgat tcctgaattt tattatctcc ctgagatgtt tgtcaacttc     7380
aataattata accttggagt gatggatgat gggacagtgg tgtctgatgt tgaacttcct     7440
ccttgggcca aaacctcgga agaattcgtt cgcataaaca gactggccct ggagagtgaa     7500
tttgtttcct gccagcttca ccaatggatt gatcttattt ttggctataa caacaagga     7560 ccagaggcag tgcgagccct caatgtgttc tattacctaa cctatgaagg agctgtcaac     7620
ctgaactcaa taactgatcc tgtgctgaga gaggctgtgg aagctcagat ccgaagtttt     7680
ggacagacgc cttcgcaact gctcatagag ccccaccctc cccgaggttc ggccatgcag     7740
gcgagtccat tgatgttcac agaccaagcc cagcaagatg tcatcatggt cctaaagttc     7800
ccttcgaatt ctccagtcac ccacgttgcg gccaacaccc agccaggcct ggcaatgcct     7860
gctgtcatca ctgtcactgc taacaggctc tttgccgtga acaagtggca caaccttcct     7920
gctcaccaag gtgctgtaca agaccagcca taccagctgc cagtggaaat cgatcctctc     7980
ataggtctgt cacttctttc tctctttgcg attcattaag ctctgtatgg tggccctgaa     8040
gtgtagatta cagttgtttt tcacttgctg gttgctggga atggaatttt cctgataaac     8100
catttgcatg caaattggaa tgcaatgagc tgtggctatg ctggtatttc atcaactccc     8160
cctcgttggt ttgcctaatt tgaacaggcc taggacgcgt gtcactgaaa attaatatgg     8220
atgctgtaat aatgtgtgat tgagaatgcg catgaagtac tgtcaggata atattggatc     8280 tttcatcac tcagacttgt tgatgagcag gagcgaggtg cgttatgatg aattggtgca     8340
aatgtaatgt gatggagctg ctttgctggg gaaattttca taataacagt gggattctta     8400
gcagcactgt gttgtgagaa ataaaactat aatgccaggg tctcatcgtt agaggagatc     8460
aatcctttct tcctgggctc tgttcagtca gaggggatta atgtgcaatc gcagagcagt     8520
ttccaagttg aaatatatta cccagccaat ggtagtgtta agatatttgt attcattttc     8580
ctagagtcct gcagccaata aattgccatt ggaggttaaa tttgttgagg gagaagaagg     8640
aaaagaaaat agggaggaga ctagaaagag ccactgggag cgaggagagc atctgcagca     8700
gaggacttga aaattttaat tgctgttatg gtttcgagtc agctgaagtc tctagttagc     8760
atttatcatt cttatgcatt gggatttcaa atgtggtgtt accaaaaagg ttaagccttg     8820 ataacttta aaaaaaaaa aaaaaaaaa aaaaaaaaa                               8860

<210> SEQ ID NO 4
<211> LENGTH: 9919
```

<212> TYPE: DNA
<213> ORGANISM: Homo sapiens

<400> SEQUENCE: 4

| | |
|---|---|
| atctccgccg ccacctcggt ctcgctgctc ctgggcgggg ggtgaggacg agtccggagt | 60 |
| atctggggtt tggcgttgtt gtcagcctcg gggagagaga ttggacaaat attctccaag | 120 |
| aggaggaggg cgacgccaag gactttccac atcaactgct ttggggtatc tccacaagtt | 180 |
| ggaagaggga ccctttcgtt ttgcattgcg tgtgttgtgc tcattaccag tgcagcgact | 240 |
| gccgtcccag ggtgactctg agttgtcctt tatcgtgagc tagcaatggc tagcgaagac | 300 |
| aatcgtgtcc cttccccgcc accaacaggt gatgacgggg gaggtggagg gagagaagaa | 360 |
| accccctactg aaggggggtgc attgtctctg aaaccagggc tccccatcag gggcatcaga | 420 |
| atgaaatttg ccgtgttgac cggtttggtt gaagttggag aagtatccaa tagggatatt | 480 |
| gtagaaactg tctttaacct gttggtagga ggacagtttg atctggaaat gaatttcatt | 540 |
| atccaagaag gtgagagtat taactgcatg gtggacctac tggaaaaatg tgacattacg | 600 |
| tgccaagcag aagtctggag catgtttaca gccattctga agaaaagcat acggaatctt | 660 |
| caagtctgca ctgaagtagg ccttgttgaa aaagtgcttg ggaaaattga aaaagttgac | 720 |
| aatatgatag cagatctttt ggttgacatg ttgggagtgc tggctagcta aatttgaca | 780 |
| gttcgcgagc taaagctttt cttcagtaaa cttcaaggag ataaaggacg atggcctcca | 840 |
| catgctggga agttgctgtc tgtgttaaag catatgcctc agaagtatgg tcctgatgcc | 900 |
| ttttttaact ttccaggaaa gagtgctgca gctattgcat tacctcctat agccaaatgg | 960 |
| ccataccaga atggttttac atttcataca tggcttagaa tggatcctgt aaataacatc | 1020 |
| aatgtagata aggataaacc atatttgtat tgtttcagaa ccagcaaagg tcttggctat | 1080 |
| tctgctcatt ttgttggagg ctgtttgatt gtaacatcaa taaagtcaaa aggaaaaggc | 1140 |
| tttcaacact gtgtgaaatt tgatttcaag ccacaaaagt ggtatatggt taccatagta | 1200 |
| cacatctata accgatggaa gaatagtgaa cttcgatgtt atgtgaatgg tgagctggct | 1260 |
| tcctatggag agataacatg gtttgtcaac actagcgata cctttgacaa atgtttcctg | 1320 |
| ggctcatcag aaacagcaga tgctaataga gtattctgtg gtcagatgac tgcagtttac | 1380 |
| cttttcagtg aagctctaaa tgcagctcag atatttgcta tttatcagtt gggcctggga | 1440 |
| tacaagggta catttaaatt caaagcagaa agcgaccttt tccttgctga gcatcacaaa | 1500 |
| cttttattgt acgatgggaa actctctagt gccattgcat tcacgtacaa tccacgggct | 1560 |
| acagatgccc agctttgtct tgaatcatct cctaaggaca acccttcaat ttttgttcat | 1620 |
| tcaccacatg cactcatgct ccaggatgta aaggcagttt taacacattc catccaaagt | 1680 |
| gcaatgcatt caattggagg agtacaagta ctatttccac tttttgcaca gttggattac | 1740 |
| aggcaatatt tgtctgatga gattgatttg actatatgtt caaccttgct ggcctttatc | 1800 |
| atggaattgt tgaagaactc aattgctatg caggaacaga tgcttgcctg taagggcttc | 1860 |
| ttggtaatag gatatagcct tgaaaagtct tccaaatctc atgttagcag agcagtactt | 1920 |
| gaactttgcc ttgcattttc aaaatatctg agtaatctgc agaatgggat gccccctgctc | 1980 |
| aagcaattgt gtgatcacgt tcttcttaat cctgccatat ggattcatac cccagccaag | 2040 |
| gttcaactga tgctctatac ttatctgtcc acggaattca ttggtacagt caacatatat | 2100 |
| aacaccattc ggagagttgg aacagtgctt ctcatcatgc acacgctgaa gtactactac | 2160 |
| tgggcagtga atcctcagga tcgaagtggt atcacccccaa aaggattaga tggaccgcga | 2220 |

```
cctaatcaaa aagaaatgct ttctctacga gcattcttgt tgatgttcat taagcaatta   2280
gtgatgaagg attctggagt aaaggaagat gaattacagg ccattcttaa ttacctactg   2340
actatgcatg aggatgacaa tctaatggat gtcctacagc tgcttgttgc attaatgtca   2400
gaacacccta actctatgat tcctgctttt gaccaaagga atgggttacg tgttatctac   2460
aaacttctgg catcgaaaag tgaaggaatc agggtacaag ctcttaaggc aatgggttat   2520 ttttaaaac atctggcccc aaagaggaaa gcagaagtca tgcttggaca tggattgttt   2580
tcattgctag ctgaaaggct catgcttcag acaaatttaa tcacaatgac cacatataat   2640
gtgctgtttg agattcttat agaacagatt ggtactcagg tgatacataa acagcatcca   2700
gatcctgatt cttcagtgaa gatacaaaac cctcagatac taaaagtaat tgcgacccta   2760
cttcgaaatt ctccccagtg cccagagagc atggaggttc gcagagcctt tctttctgac   2820
atgattaaac tttttaataa cagtagagaa acaggagga gcttgctaca atgctctgtg   2880
tggcaagaat ggatgctttc tctctgctat tttaatccta agaattcaga tgagcaaaag   2940
ataacagaaa tggtatacgc catattcaga atcctgcttt accatgcagt caaatatgag   3000
tggggtggct ggcgtgtatg ggtagacact ttatcaatca ctcattcaaa ggtcactttt   3060
gaaatacaca agaaaaacct tgccaatata tttagggaac agcaaggaaa agttgatgaa   3120
gaaatagggc tgtgttcttc aacttcagtt caagcagcct ctggcattag aagggatatt   3180
aatgtttcag taggatccca gcaaccagat acgaaggatt ctcctgtctg tcctcatttc   3240
accacaaatg gtaatgaaaa ttcaagtata gagaagacaa gttcactaga atctgcatct   3300
aatattgaac tgcaaactac taatacatct tatgaagaaa tgaaagctga gcaagaaaat   3360
caggagttac cagatgaagg cactttggaa gaaacactga caaatgagac aaggaatgca   3420
gatgatttag aagtatcttc tgacataata gaagctgtgg ctatttcctc taattctttt   3480
ataacaactg gcaaagattc aatgactgtc agtgaagtaa ctgcttctat aagttctcct   3540
tcagaagagg atgcctcaga gatgccagaa ttcttggata aatctatagt agaggaagag   3600
gaagatgatg attatgtgga actgaaagta gaaggcagtc ctactgagga agctaatcta   3660
cccacagagc tccaagataa cagtttgtct ccagctgcat ctgaagccgg tgaaaaactg   3720
gacatgtttg gtaatgatga caaattaata tttcaagaag gaaaacctgt tactgaaaag   3780
caaactgata ctgaaaactca agattctaaa gattctggaa ttcagactat gacagcatca   3840
gggtcttcag ctatgtcacc agaaactact gtttcccaaa tagctgtaga atcagacctt   3900
ggtcagatgc tggaggaagg gaagaaagca actaacctca ctagagaaac caaattaatt   3960
aatgattgtc atggtagtgt ctctgaggct tcttctgagc aaaagattgc gaagttggat   4020
gtttccaatg ttgctacaga tactgagagg ctggagttga aggccagtcc caacgtggaa   4080
gcacctcaac ctcatcgaca tgtgcttgag atatcaaggc aacatgagca gccagggcaa   4140
ggaatagcac cagatgcagt taatggacaa aggagggatt ccagatctac tgtgtttcgt   4200
attcctgagt tcaactggtc tcagatgcat caacgtttgc tcactgatct attattttca   4260
atagaaacag atatacagat gtggagaagc cattcaacaa agacagttat ggacttcgtg   4320
aatagcagtg ataatgtcat cttttgtacac aacacaattc atctcatctc tcaagtgatg   4380
gacaatatgg tcatggcttg tgggggtata ctgccattgc tttcagctgc tacatcggct   4440
acacatgaac tggaaaatat tgaacctact caaggccttt caatagaagc ctctgtgaca   4500
tttttgcaga ggctaattag ccttgtggat gtgcttatat ttgcaagttc tcttggcttt   4560
actgaaattg aagctgaaaa aagtatgtca tctggaggaa ttttgcggca gtgtctccga   4620
```

```
ctagtttgtg cagtcgcagt aaggaattgc ttggagtgtc aacagcattc acaactgaaa    4680
actaggggag ataaagcctt gaaaccaatg catagcctta ttcctttagg gaaatctgca    4740
gcgaagagcc cagtggacat tgtgactggc ggtatatctc cagtaagaga tcttgacagg    4800
cttctacagg acatggatat taatcggctt agggcagttg ttttcagaga catagaggat    4860
agcaaacaag ctcaattttt agccttggca gtagtatact ttatctctgt tcttatggtc    4920
tccaagtaca gagacatttt ggaaccccaa aatgaaaggc atagccagtc atgtacagaa    4980
actggcagtg aaaatgagaa tgtatcactc tctgaaatca caccagcagc attcagcact    5040
ttaactacgg catcagtgga agaatctgaa agcacatcat ctgctcgaag agggactca    5100 ggcattgggg aagaaacagc cactggttta ggaagccatg tggaagtaac tcctcacaca    5160
gcacctcctg tgtcagtgc aggcccagat gcaatcagcg aggtgctatc tactctttct    5220
ttagaagtca ataagtctcc ggaaaccaaa aatgatagag gaaatgactt ggacactaag    5280
gctacaccgt cagtttcagt ttcaaaaaac gtcaatgtga agacattct ccgaagcttg    5340 gttaacatac cagcagatgg agtcacagtg gatcctgccc ttctgccacc agcctgcctt    5400
ggagcccttg tgatctatc tgtggaacaa cccgtgcagt tcagatcttt tgacagaagt    5460
gtcattgttg cagcaaaaaa gtcagcagtc tcaccttcca cctttaatac aagcatacct    5520
accaatgctg tcagtgtggt ttcctcagta gattcagccc aagcctcaga tatgggagga    5580
gaatcaccag gcagtagatc atctaatgca aaattgccct cagttccaac agttgattca    5640
gtttcacaag atccggtttc aaatatgagt attacagaga ggcttgaaca cgctttggaa    5700
aaggcagctc ctctccttcg tgagattttt gtggatttg caccttttct ttctcggaca    5760
cttttgggta gccatggaca agaactgctt atagaaggaa caagtctggt ttgcatgaag    5820
tcgagtagtt cagttgtgga attggttatg ctactgtgtt ctcaggagtg gcaaaattct    5880
attcagaaga atgcaggcct tgctttatc gaacttgtca atgaaggaag gttgcttagc    5940
cagacaatga aggatcatct agtaagagta gcaaatgaag ctgaatttat cctgagcagg    6000
cagagagcag aagatattca cagacatgcg gaatttgagt cactgtgtgc ccagtattct    6060
gcagacaaac gagaagatga aagatgtgt gatcatttga taagagcagc aaaatatcgt    6120
gaccacgtga cagcaactca actaatccag aaaattatca acattctcac agacaagcat    6180
ggagcctggg gaaattctgc agtgagtcgt cctcttgagt tctggcgcct tgactactgg    6240
gaagatgact tgcggcgccg gcgacgattt gtgcgtaacc ctctaggatc gacacatcct    6300
gaagcgacac taaaaacagc cgtggaacat gccacagatg aagatatcct tgctaaagga    6360
aaacagtcca tcaggagtca ggctttagga aatcagaact cagaaaacga gatcctcctg    6420
gaaggcgatg atgatactct gtcatccgtg gatgagaaag atttagagaa tcttgccggt    6480
cctgttagcc tgagcacacc agctcagctt gtggcccccct ctgttgtagt aaagggcact    6540 cttttctgtca cctcctccga actctatttt gaggtggatg aagaggatcc taacttcaaa    6600
aaaatcgacc ccaagatctt ggcatataca gaagggctgc atggaaaatg gctgttcaca    6660
gagatacgat caatcttttc tcgtcgttat cttttgcaaa atacagccct ggagatcttt    6720
atggcaaaca gagttgctgt gatgttcaac ttcccagacc ctgcaacagt aaagaaagtg    6780
gttaactatc tacctcgtgt tggcgttgga acaagttttg gattgcctca aaccagacgt    6840
atttcattag ctagtccacg tcagcttttt aaggcttcta atatgaccca gcgatggcaa    6900
cacagagaga tatctaattt tgagtacttg atgtttctca acacgatagc aggacggagt    6960
```

```
tataatgact taaatcagta tccagtgttt ccttgggtca tcactaatta tgaatcagaa    7020
gaactggatc ttaccttgcc caccaacttc agagatttgt ccaagccaat aggagctctg    7080
aacccaaaaa gagcagcatt cttcgctgag cgttatgaat catgggaaga tgatcaagtt    7140
ccaaagtttc actatggtac tcattactca actgcaagtt ttgttcttgc atggctgcta    7200
agaatagaac cctttacaac ttatttccta aatttgcaag gaggcaaatt tgatcatgca    7260
gatcgaactt tttcatcaat ttccagagct tggcgaaaca gtcagcgtga tacctctgat    7320
attaaggagt tgatccctga attttattat ctccctgaga tgtttgtcaa cttcaataat    7380
tataatcttg gagtgatgga tgatgggaca gtagtgtctg atgtcgaact tcctccttgg    7440
gccaaaacct cagaagaatt tgttcacata aacagattgg ccctggagag tgaatttgtt    7500
tcctgccagc ttcaccaatg gattgatctc attttggct ataaacagca aggaccagaa    7560
gctgtccgag ccctcaatgt gttctattac ttgacctatg aaggagctgt caatctgaat    7620
tcaataactg atcctgtgtt gagagaggct gttgaagctc aaatccgaag ttttggacag    7680
actccttctc aactactcat agagccccat cctcccagag ttctgccat gcaagtgagt    7740 ccattgatgt tcacagacaa agcccagcag gatgttatca tggtcctcaa gtttccctcc    7800
aactcccctg ttactcacgt ggcagccaac acccagcctg gtttggcaac tcccgctgtg    7860
atcacagtca ctgctaacag gttatttgcg gtgaacaaat ggcacaacct tcctgctcat    7920
caaggtgctg tacaagacca gccataccag ctgccagtgg aaatcgatcc tctcatagcc    7980
agcaatacag gaatgcacag gaggcaaatc actgaccttt tagaccaaag tattcaagtg    8040
cattcccagt gctttgtcat cacttcagac aaccgctata ttctcgtctg tggcttctgg    8100
gataaaagtt tcagagtcta ttctacagac acaggaagat tgatccaagt ggtgtttggc    8160
cattgggatg tcgtcacttg ccttgctcgt tctgagtcat atattggggg aaattgctac    8220
attctctcag ggtcacgtga tgcaactctt ttgctgtggt attggaatgg aaaatgcagt    8280
gggattggag ataacccagg tgagactgct gctcctcggg ccatttttgac cggccatgac    8340 tatgaggtca catgtgctgc ggtgtgtgcg gagctaggcc tggtgttgag tggttcacaa    8400
gaaggaccat gtctcataca ttccatgaat ggagacttgt tgaggacctt ggagggtcct    8460
gaaaactgcc tgaaaccaaa actcattcag gcttcaagag agggtcattg tgtcatattc    8520
tatgaaaacg gcctcttctg tacattcagt gtgaatggaa aactccaggc cacgatggaa    8580
acagatgata acataagagc catccagctg agccgagatg ggcagtacct gctcacagga    8640
ggagacagag gagtggtcgt ggtccggcag gtgtcggacc tcaagcagct cttgcctat    8700 ccaggatgtg acgctggaat ccgggccatg gcgctgtctt acgaccagag gtgcatcatt    8760
tctggcatgg cttcaggaag cattgtgcta ttttacaacg actttaaccg gtggcatcat    8820
gaataccaaa cccgctactg atggtgacag ctgtacatca actctgcccc taggatgagc    8880
agaagtacct ggagcatcat tctcttctac cacatctgaa tgtaacttaa atttgctcaa    8940
agaagcaaaa tatttttaa agttattaat aattgctatt tttgtagtct ttgcttgact    9000
tttttggggg ggattagcaa agcagaaaac tggctgctgg gttctgtagt tttaaaaaat    9060 ctatatttt agtcataatg agaagtctat tttcaccaat tatggaaaca tacagtggag    9120
caagtaaacc acttattcca gctataatat tatgaagaac atttcccatg catctacaag    9180
cttgagaaat aggattttca cagtggggaa gtgggttaca atattggaat aggaaaattt    9240
gatgctgtaa tttgggtcct gtatttttcc aaacaactgt gcttcttcag cactaatatt    9300
tctgggattt aaatagtaat gtttaaatta tggtaaatgt aatttaaaac atctcaatta    9360
```

```
agtctgtcta tcaatattgt tcttcaagca tgttttagac ctagaaaagt atggtttggg    9420
ggaggctatt ttattgtgtg gttagcacaa ggaatctaat ttatagcaag tgtgaaatag    9480
ttaccatttt ttcctgatct gtcatcttca tagcacaaca aaacgaaatg atggaaatgc    9540
tcttgagctc acaacatttg ttttttcttt aaagtaaatg caagtaccaa agctcactac    9600
tgcggtttgc ctgtgcctgg acaatgaggc ggagccactg ttgttttgtt ggggcacccc    9660
cttccctccc cgggtttgca atagaggct accgggtgct gtattcagca acacctgttt    9720
tactatttgt tattaaacta tcatctccac cttccttttg attagcaatt tgtactaaga    9780
aacgaaacaa tgttatttgg tggtgtataa ttctactttt ctagtagatt actgtgtgga    9840
attctgtgaa aaatatttga gaaaaggcct gtattgcata aataaattct ttgtatgttg    9900
tgaaaaaaaa aaaaaaaa                                                  9919

<210> SEQ ID NO 5
<211> LENGTH: 9914
<212> TYPE: DNA
<213> ORGANISM: Homo sapiens

<400> SEQUENCE: 5
agggaaactt ggaggctgcg accagggttt ggcgttgttg tcagcctcgg ggagagagat      60
tggacaaata ttctccaaga ggaggagggc gacgccaagg actttccaca tcaactgctt     120
tggggtatct ccacaagttg gaagagggac cctttcgttt tgcattgcgt gtgttgtgct     180
cattaccagt gcagcgactg ccgtcccagg gtgactctga gttgtccttt atcgtgagct     240
agcaatggct agcgaagaca atcgtgtccc ttccccgcca ccaacaggtg atgacggggg     300
aggtggaggg agagaagaaa cccctactga aggggtgca ttgtctctga aaccagggct      360
ccccatcagg ggcatcagaa tgaaatttgc cgtgttgacc ggtttggttg aagttggaga     420
agtatccaat agggatattg tagaaactgt ctttaacctg ttggtaggag acagtttga      480 tctggaaatg aatttcatta tccaagaagg tgagagtatt aactgcatgg tggacctact     540
ggaaaaatgt gacattacgt gccaagcaga agtctggagc atgtttacag ccattctgaa     600
gaaaagcata cggaatcttc aagtctgcac tgaagtaggc cttgttgaaa aagtgcttgg     660
gaaaattgaa aaagttgaca atatgatagc agatcttttg gttgacatgt tgggagtgct     720
ggctagctat aatttgacag ttcgcgagct aaagcttttc ttcagtaaac ttcaaggaga     780
taaaggacga tggcctccac atgctgggaa gttgctgtct gtgttaaagc atatgcctca     840
gaagtatggt cctgatgcct tttttaactt tccaggaaag agtgctgcag ctattgcatt     900
acctcctata gccaaatggc ataccagaa tggttttaca tttcatacat ggcttagaat      960
ggatcctgta ataacatca atgtagataa ggataaacca tatttgtatt gtttcagaac     1020
cagcaaaggt cttggctatt ctgctcattt tgttggaggc tgtttgattg taacatcaat    1080
aaagtcaaaa ggaaaaggct ttcaacactg tgtgaaattt gatttcaagc cacaaaagtg    1140
gtatatggtt accatagtac acatctataa ccgatggaag aatagtgaac ttcgatgtta    1200
tgtgaatggt gagctggctt cctatggaga gataacatgg tttgtcaaca ctagcgatac    1260
ctttgacaaa tgtttcctgg gctcatcaga aacagcagat gctaatagag tattctgtgg    1320
tcagatgact gcagtttacc ttttcagtga agctctaaat gcagctcaga tatttgctat    1380
ttatcagttg ggcctgggat acaagggtac atttaaattc aaagcagaaa gcgacctttt    1440
ccttgctgag catcacaaac tttttattgta cgatgggaaa ctctctagtg ccattgcatt    1500
```

| | |
|---|---|
| cacgtacaat ccacgggcta cagatgccca gctttgtctt gaatcatctc ctaaggacaa | 1560 |
| cccttcaatt tttgttcatt caccacatgc actcatgctc caggatgtaa aggcagtttt | 1620 |
| aacacattcc atccaaagtg caatgcattc aattggagga gtacaagtac tatttccact | 1680 |
| ttttgcacag ttggattaca ggcaatattt gtctgatgag attgatttga ctatatgttc | 1740 |
| aaccttgctg gcctttatca tggaattgtt gaagaactca attgctatgc aggaacagat | 1800 |
| gcttgcctgt aagggcttct tggtaatagg atatagcctt gaaaagtctt ccaaatctca | 1860 |
| tgttagcaga gcagtacttg aactttgcct tgcattttca aaatatctga gtaatctgca | 1920 |
| gaatgggatg cccctgctca agcaattgtg tgatcacgtt cttcttaatc ctgccatatg | 1980 |
| gattcatacc ccagccaagg ttcaactgat gctctatact tatctgtcca cggaattcat | 2040 |
| tggtacagtc aacatatata acaccattcg gagagttgga acagtgcttc tcatcatgca | 2100 |
| cacgctgaag tactactact gggcagtgaa tcctcaggat cgaagtggta tcaccccaaa | 2160 |
| aggattagat ggaccgcgac ctaatcaaaa agaaatgctt tctctacgag cattcttgtt | 2220 |
| gatgttcatt aagcaattag tgatgaagga ttctggagta aaggaagatg aattacaggc | 2280 |
| cattcttaat tacctactga ctatgcatga ggatgacaat ctaatggatg tcctacagct | 2340 |
| gcttgttgca ttaatgtcag aacaccctaa ctctatgatt cctgcttttg accaaaggaa | 2400 |
| tgggttacgt gttatctaca aacttctggc atcgaaaagt gaaggaatca gggtacaagc | 2460 |
| tcttaaggca atgggttatt ttttaaaaca tctggcccca aagaggaaag cagaagtcat | 2520 |
| gcttggacat ggattgtttt cattgctagc tgaaaggctc atgcttcaga caaatttaat | 2580 |
| cacaatgacc acatataatg tgctgtttga gattcttata gaacagattg gtactcaggt | 2640 |
| gatacataaa cagcatccag atcctgattc ttcagtgaag atacaaaacc ctcagatact | 2700 |
| aaaagtaatt gcgaccctac ttcgaaattc tccccagtgc ccagagagca tggaggttcg | 2760 |
| cagagccttt ctttctgaca tgattaaact ttttaataac agtagagaaa acaggaggag | 2820 |
| cttgctacaa tgctctgtgt ggcaagaatg gatgctttct ctctgctatt ttaatcctaa | 2880 |
| gaattcagat gagcaaaaga taacagaaat ggtatacgcc atattcgaaa tcctgcttta | 2940 |
| ccatgcagtc aaatatgagt ggggtggctg gcgtgtatgg gtagacactt tatcaatcac | 3000 |
| tcattcaaag gtcacttttg aaatacacaa agaaaacctt gccaatatat ttagggaaca | 3060 |
| gcaaggaaaa gttgatgaag aaatagggct gtgttcttca acttcagttc aagcagcctc | 3120 |
| tggcattaga agggatatta atgtttcagt aggatcccag caaccagata cgaaggattc | 3180 |
| tcctgtctgt cctcatttca ccacaaatgg taatgaaaat tcaagtatag agaagacaag | 3240 |
| ttcactagaa tctgcatcta atattgaact gcaaactact aatacatctt atgaagaaat | 3300 |
| gaaagctgag caagaaaatc aggagttacc agatgaaggc actttggaag aaacactgac | 3360 |
| aaatgagaca aggaatgcag atgatttaga agtatcttct gacataatag aagctgtggc | 3420 |
| tatttcctct aattcttta taacaactgg caaagattca atgactgtca gtgaagtaac | 3480 |
| tgcttctata agttctcctt cagaagagga tgcctcagag atgccagaat cttggataa | 3540 |
| atctatagta gaggaagagg aagatgatga ttatgtggaa ctgaaagtag aaggcagtcc | 3600 |
| tactgaggaa gctaatctac ccacagagct ccaagataac agtttgtctc agctgcatc | 3660 |
| tgaagccggt gaaaaactgg acatgtttgg taatgatgac aaattaatat tcaagaagg | 3720 |
| aaaacctgtt actgaaaagc aaactgatac tgaaactcaa gattctaaag attctggaat | 3780 |
| tcagactatg acagcatcag ggtcttcagc tatgtcacca gaaactactg tttcccaaat | 3840 |
| agctgtagaa tcagaccttg gtcagatgct ggaggaaggg aagaaagcaa ctaacctcac | 3900 |

```
tagagaaacc aaattaatta atgattgtca tggtagtgtc tctgaggctt cttctgagca    3960
aaagattgcg aagttggatg tttccaatgt tgctacagat actgagaggc tggagttgaa    4020
ggccagtccc aacgtggaag cacctcaacc tcatcgacat gtgcttgaga tatcaaggca    4080
acatgagcag ccagggcaag gaatagcacc agatgcagtt aatggacaaa ggagggattc    4140
cagatctact gtgtttcgta ttcctgagtt caactggtct cagatgcatc aacgtttgct    4200
cactgatcta ttattttcaa tagaaacaga tatacagatg tggagaagcc attcaacaaa    4260
gacagttatg gacttcgtga atagcagtga taatgtcatc tttgtacaca acacaattca    4320
tctcatctct caagtgatgg acaatatggt catggcttgt gggggtatac tgccattgct    4380
ttcagctgct acatcggcta cacatgaact ggaaaatatt gaacctactc aaggcctttc    4440
aatagaagcc tctgtgacat ttttgcagag gctaattagc cttgtggatg tgcttatatt    4500
tgcaagttct cttggcttta ctgaaattga agctgaaaaa agtatgtcat ctggaggaat    4560
tttgcggcag tgtctccgac tagtttgtgc agtcgcagta aggaattgct tggagtgtca    4620
acagcattca caactgaaaa ctaggggaga taaagccttg aaaccaatgc atagccttat    4680
tcctttaggg aaatctgcag cgaagagccc agtggacatt tgtgactggcg gtatatctcc    4740 agtaagagat cttgacaggc ttctacagga catggatatt aatcggctta gggcagttgt    4800
tttcagagac atagaggata gcaaacaagc tcaattttta gccttggcag tagtatactt    4860
tatctctgtt cttatggtct ccaagtacag agacattttg gaaccccaaa atgaaaggca    4920
tagccagtca tgtacagaaa ctggcagtga aaatgagaat gtatcactct ctgaaatcac    4980
accagcagca ttcagcactt taactacggc atcagtggaa gaatctgaaa gcacatcatc    5040
tgctcgaagg agggactcag gcattgggga agaaacagcc actggtttag gaagccatgt    5100
ggaagtaact cctcacacag cacctcctgg tgtcagtgca ggcccagatg caatcagcga    5160
ggtgctatct actctttctt tagaagtcaa taagtctccg gaaaccaaaa atgatagagg    5220
aaatgacttg gacactaagg ctacaccgtc agtttcagtt tcaaaaaacg tcaatgtgaa    5280
agacattctc cgaagcttgg ttaacatacc agcagatgga gtcacagtgg atcctgccct    5340
tctgccacca gcctgccttg gagcccttgg tgatctatct gtggaacaac ccgtgcagtt    5400
cagatctttt gacagaagtg tcattgttgc agcaaaaaag tcagcagtct caccttccac    5460
ctttaataca agcataccta ccaatgctgt cagtgtggtt tcctcagtag attcagccca    5520
agcctcagat atgggaggag aatcaccagg cagtagatca tctaatgcaa aattgccctc    5580
agttccaaca gttgattcag tttcacaaga tccggtttca aatatgagta ttacagagag    5640
gcttgaacac gctttggaaa aggcagctcc tctccttcgt gagattttg tggattttgc    5700 accttttctt tctcggacac ttttgggtag ccatggacaa gaactgctta tagaaggaac    5760
aagtctggtt tgcatgaagt cgagtagttc agttgtggaa ttggttatgc tactgtgttc    5820
tcaggagtgg caaaattcta ttcagaagaa tgcaggcctt gcttttatcg aacttgtcaa    5880
tgaaggaagg ttgcttagcc agacaatgaa ggatcatcta gtaagagtag caaatgaagc    5940
tgaatttatc ctgagcaggc agagagcaga agatattcac agacatgcgg aatttgagtc    6000
actgtgtgcc cagtattctg cagacaaacg agaagatgag aagatgtgtg atcatttgat    6060
aagagcagca aaatatcgtg accacgtgac agcaactcaa ctaatccaga aaattatcaa    6120
cattctcaca gacaagcatg gagcctgggg aaattctgca gtgagtcgtc ctcttgagtt    6180
ctggcgcctt gactactggg aagatgactt gcggcgccgg cgacgatttg tgcgtaaccc    6240
```

```
tctaggatcg acacatcctg aagcgacact aaaaacagcc gtggaacatg tgtgcatttt    6300
taaattgaga gagaacagca aagccacaga tgaagatatc cttgctaaag gaaaacagtc    6360
catcaggagt caggctttag gaaatcagaa ctcagaaaac gagatcctcc tggaaggcga    6420
tgatgatact ctgtcatccg tggatgagaa agatttagag aatcttgccg gtcctgttag    6480
cctgagcaca ccagctcagc ttgtggcccc ctctgttgta gtaaagggca ctctttctgt    6540
cacctcctcc gaactctatt ttgaggtgga tgaagaggat cctaacttca aaaaatcga    6600 ccccaagatc ttggcatata cagaagggct gcatggaaaa tggctgttca cagagatacg    6660
atcaatcttt tctcgtcgtt atcttttgca aaatacagcc ctggagatct ttatggcaaa    6720
cagagttgct gtgatgttca acttcccaga ccctgcaaca gtaaagaaag tggttaacta    6780
tctacctcgt gttggcgttg gaacaagttt tggattgcct caaaccagac gtatttcatt    6840
agctagtcca cgtcagcttt taaggcttc taatatgacc cagcgatggc aacacagaga    6900
gatatctaat tttgagtact tgatgttct caacacgata gcaggacgga gttataatga    6960
cttaaatcag tatccagtgt ttccttgggt catcactaat tatgaatcag aagaactgga    7020
tcttaccttg cccaccaact tcagagattt gtccaagcca ataggagctc tgaacccaaa    7080
aagagcagca ttcttcgctg agcgttatga atcatgggaa gatgatcaag ttccaaagtt    7140
tcactatggt actcattact caactgcaag ttttgttctt gcatggctgc taagaataga    7200
accctttaca acttatttcc taaatttgca aggaggcaaa tttgatcatg cagatcgaac    7260
tttttcatca atttccagag cttggcgaaa cagtcagcgt gatacctctg atattaagga    7320
gttgatccct gaattttatt atctccctga gatgtttgtc aacttcaata attataatct    7380
tggagtgatg gatgatggga cagtagtgtc tgatgtcgaa cttcctcctt gggccaaaac    7440
ctcagaagaa tttgttcaca taaacagatt ggccctggag agtgaatttg tttcctgcca    7500
gcttcaccaa tggattgatc tcattttgg ctataaacag caaggaccag aagctgtccg    7560
agccctcaat gtgttctatt acttgaccta tgaaggagct gtcaatctga attcaataac    7620
tgatcctgtg ttgagagagg ctgttgaagc tcaaatccga agttttggac agactccttc    7680
tcaactactc atagagcccc atcctcccag aggttctgcc atgcaagtga gtccattgat    7740
gttcacagac aaagcccagc aggatgttat catggtcctc aagtttccct ccaactcccc    7800
tgttactcac gtggcagcca acacccagcc tggtttggca actcccgctg tgatcacagt    7860
cactgctaac aggttatttg cggtgaacaa atggcacaac cttcctgctc atcaaggtgc    7920
tgtacaagac cagccatacc agctgccagt ggaaatcgat cctctcatag ccagcaatac    7980
aggaatgcac aggaggcaaa tcactgacct tttagaccaa gtattcaag tgcattccca    8040 gtgctttgtc atcacttcag acaaccgcta tattctcgtc tgtggcttct gggataaaag    8100
tttcagagtc tattctacag acacaggaag attgatccaa gtggtgtttg gccattggga    8160
tgtcgtcact tgccttgctc gttctgagtc atatattggg ggaaattgct acattctctc    8220
agggtcacgt gatgcaactc ttttgctgtg gtattggaat ggaaaatgca gtgggattgg    8280
agataaccca ggcagtgaga ctgctgctcc tcgggccatt ttgaccggcc atgactatga    8340
ggtcacatgt gctgcggtgt gtgcggagct aggcctggtg ttgagtggtt cacaagaagg    8400
accatgtctc atacattcca tgaatggaga cttgttgagg accttggagg gtcctgaaaa    8460
ctgcctgaaa ccaaaactca ttcaggcttc aagagagggt cattgtgtca tattctatga    8520
aaacggcctt ttctgtacat tcagtgtgaa tggaaaactc caggccacga tggaaacaga    8580
tgataacata agagccatcc agctgagccg agatgggcag tacctgctca caggaggaga    8640
```

| | |
|---|---|
| cagaggagtg gtcgtggtcc ggcaggtgtc ggacctcaag cagctctttg cctatccagg | 8700 |
| atgtgacgct ggaatccggg ccatggcgct gtcttacgac cagaggtgca tcatttctgg | 8760 |
| catggcttca ggaagcattg tgctatttta caacgacttt aaccggtggc atcatgaata | 8820 |
| ccaaacccgc tactgatggt gacagctgta catcaactct gccctagga tgagcagaag | 8880 |
| tacctggagc atcattctct tctaccacat ctgaatgtaa cttaaatttg ctcaaagaag | 8940 |
| caaaatattt tttaaagtta ttaataattg ctattttttgt agtctttgct tgacttttt | 9000 |
| gggggggatt agcaaagcag aaaactggct gctgggttct gtagttttaa aaaatctata | 9060 |
| ttttttagtca taatgagaag tctatttttca ccaattatgg aaacatacag tggagcaagt | 9120 |
| aaaccactta ttccagctat aatattatga agaacatttc ccatgcatct acaagcttga | 9180 |
| gaaataggat tttcacagtg gggaagtggg ttacaatatt ggaataggaa aatttgatgc | 9240 |
| tgtaatttgg gtcctgtatt tttccaaaca actgtgcttc ttcagcacta atatttctgg | 9300 |
| gatttaaata gtaatgttta aattatggta aatgtaattt aaaacatctc aattaagtct | 9360 |
| gtctatcaat attgttcttc aagcatgttt tagacctaga aaagtatggt ttgggggagg | 9420 |
| ctattttatt gtgtggttag cacaaggaat ctaatttata gcaagtgtga aatagttacc | 9480 |
| attttttcct gatctgtcat cttcatagca caacaaaacg aaatgatgga aatgctcttg | 9540 |
| agctcacaac atttgttttt cttttaaagt aaatgcaagt accaaagctc actactgcgg | 9600 |
| tttgcctgtg cctggacaat gaggcggagc cactgttgtt ttgttggggc accccttcc | 9660 |
| ctccccgggt ttgcaaatag aggctaccgg gtgctgtatt cagcaacacc tgtttttacta | 9720 |
| tttgttatta aactatcatc tccaccttcc ttttgattag caatttgtac taagaaacga | 9780 |
| aacaatgtta tttggtggtg tataattcta cttttctagt agattactgt gtggaattct | 9840 |
| gtgaaaaata tttgagaaaa ggcctgtatt gcataaataa attctttgta tgttgtgaaa | 9900 |
| aaaaaaaaaa aaaa | 9914 |

<210> SEQ ID NO 6
<211> LENGTH: 4128
<212> TYPE: DNA
<213> ORGANISM: Mus musculus

<400> SEQUENCE: 6

| | |
|---|---|
| gtccgtctgt ctgctctctc tcgacgtcag tgggaatttc cagccaggaa gtgagagagt | 60 |
| gagcgagaga ggacgagaga gaagtaccga ggcgagccgg gcaggaagag gaggtttcgc | 120 |
| cacccgagca gccggctgc gcgctgacgg cttcccgtgc cctgcgcgcc cccggcctgc | 180 |
| cgccgccgcc gccgccgccg ccgccctcgg cctgctcgcg ggccggctct agcagcgcag | 240 |
| gccggagctc agggccccgc cgcgcccggc ccgccccgcg cttctccgcc cgcgccgcag | 300 |
| ccatggcgcg ccgctgagcc gccgcccgc ccgcccgcgc ccgacccgg tcgggctcc | 360 |
| cgccggtccg cgccgctccg cagcgggagc ccgcaggcga ggagaggccg cgccgcatct | 420 |
| ccagggtacc ctcagaggcc agaagagggt gtcagagccc ttgtaactgg agtttgacgg | 480 |
| tcgtgagctg cgcatcttca ccatggcaga cgatgatccc tacggaactg ggcaaatgtt | 540 |
| tcatttgaac actgctttga ctcactcaat atttaatgca gaattatatt caccagaaat | 600 |
| accactgtca acagatggcc cataccttca atattagag caaccaaaac agaggggatt | 660 |
| tcgattccgc tatgtgtgtg aaggcccatc acacggaggg cttccgggag cctctagtga | 720 |
| gaagaacaag aaatcctacc cacaggtcaa aatttgcaac tatgtggggc ctgcaaaggt | 780 |

| | |
|---|---|
| tatcgttcag ttggtcacaa atggaaaaaa catccacctg cacgcccaca gcctggtggg | 840 |
| caagcactgt gaggacgggg tatgcaccgt aacagcagga cccaaggaca tggtggttgg | 900 |
| ctttgcaaac ctgggaatac ttcatgtgac taagaaaaag gtatttgaaa cactggaagc | 960 |
| acggatgaca gaggcgtgta ttaggggcta taatcctgga cttctggtgc attctgacct | 1020 |
| tgcctatcta caagcagaag gcggaggaga ccggcaactc acagacagag agaaggagat | 1080 |
| catccgccag gcagccgtgc agcagaccaa ggagatggac ctgagcgtgg tgcgcctcat | 1140 |
| gttcacagcc ttcctccctg acagcactgg cagcttcact cggagactgg agcctgtggt | 1200 |
| gtcagacgcc atctatgata gcaaagcccc gaatgcatcc aacctgaaaa tcgtgagaat | 1260 |
| ggacagaaca gcaggatgtg tgacgggagg ggaggagatt taccttctct gtgacaaggt | 1320 |
| tcagaaagat gacatccaga ttcggtttta tgaagaggaa gaaaatggcg gagtttggga | 1380 |
| aggatttggg gacttttccc ccacagatgt tcatagacag tttgccattg tcttcaaaac | 1440 |
| gccaaagtat aaggatgtca acattacaaa gccagcttcc gtgtttgttc agcttcggag | 1500 |
| gaaatcagac ctggaaacta gtgaaccgaa accctttctc tactaccctg aaatcaaaga | 1560 |
| caaagaggaa gtgcaaagga aacgccagaa gcttatgccg aacttctcgg acagcttcgg | 1620 |
| tggcggcagt ggagcgggag ccggtggtgg aggcatgttc ggtagtggcg gtggcggagg | 1680 |
| gagtaccgga agccctggcc cagggtatgg ctactcgaac tacggatttc ctccctacgg | 1740 |
| tgggattaca ttccatcccg gagtcacgaa atccaacgca ggggtcaccc atggcaccat | 1800 |
| aaacaccaaa tttaaaaatg gccctaaaga ttgtgccaag agtgatgacg aggagagtct | 1860 |
| gactctccct gagaaggaaa ctgaaggtga agggcccagc ctgcccatgg cctgcaccaa | 1920 |
| gacggaaccc atcgccttgg catccaccat ggaagacaag gagcaggaca tgggatttca | 1980 |
| ggataacctc tttcttgaga aggctctgca gctcgccagg cgacacgcca acgcccttt | 2040 |
| cgactacgca gtgacggggg atgtgaagat gttgctggcc gtgcaacgcc atctcaccgc | 2100 |
| cgtgcaggat gagaatgggg acagtgtctt acacttagcc atcatccacc tccacgctca | 2160 |
| gcttgtgagg gatctgctgg aagtcacatc tggtttgatc tctgatgaca tcatcaacat | 2220 |
| gagaaatgac ctgtatcaga cacctctgca cttggccgtg atcaccaagc aggaagatgt | 2280 |
| agtagaggat ttgctgaggg ttggggctga cctgagcctt ctggaccgct ggggcaactc | 2340 |
| tgtcctgcac ctagctgcca agaaggacac gacagaatc ctcagcatcc tgctcaagag | 2400 |
| cagaaaagca gcgcccctta tcgaccaccc caatgggaa ggtctaaatg ccatccacat | 2460 |
| agctgtgatg agcaatagcc tgccatgtct gctgctgctg gtggctgccg gggcagaagt | 2520 |
| caatgctcag gagcagaagt ctgggcgcac agcgctgcac ctggccgtgg agtacgacaa | 2580 |
| catctccttg gctggctgcc tgcttctgga gggtgatgcc cacgtggaca gtaccaccta | 2640 |
| tgatgggact acacctctgc atatagcggc cggaagaggg tccaccagac tggcagctct | 2700 |
| tctcaaagca gcaggagcag acccctggt ggagaacttt gagcctctct atgacctgga | 2760 |
| cgactcttgg gagaaggctg gagaagatga gggagtggtg ccaggtacca cacccctgga | 2820 |
| catggctgcc aactggcagg tatttgacat actaaatggg aaaccgtatg agcctgtgtt | 2880 |
| cacatctgat gatatactac acaaggggca catgaagcag ctgacagaag acacgaggct | 2940 |
| acaactctgc aaactgctgg aaattcctga tccagacaaa actgggcca ctctggcaca | 3000 |
| gaagttgggt ctggggatac tgaacaatgc cttccgctg agtcctgctc cttctaaaac | 3060 |
| tctcatggac aactatgagg tctctggggg taccatcaaa gagctgatgg aggccctgca | 3120 |
| acagatgggc tacacagagg ccattgaagt gatccaggca gccttccgca cccggcaac | 3180 |

-continued

| | |
|---|---|
| cacagcctcc agccccgtga ccactgctca ggtccactgt ctgcctctct cgtcttcctc | 3240 |
| cacgaggcag cacatagatg aactccggga tagtgacagc gtctgtgaca gtggtgtgga | 3300 |
| gacatccttc cgcaaactca gctttacaga gtctcttact ggagacagcc cactgctatc | 3360 |
| tctgaacaaa atgccccacg gttatgggca ggaaggacct attgaaggca aaatttagcc | 3420 |
| tgctggccgt tcccccacac tgtgtaaacc aaagccctga cagtccattg catcgtccca | 3480 |
| aaggaggaag gcaaagcgaa tccaaaggtg ctggagaatc gccggcctgc agggtcactc | 3540 |
| gatttcattc aaggccttcc gaatttggcg tcctttcttg gttctgaaat gaaatgtagt | 3600 |
| tgccacgcac agacggtgtc tagcaatcat ggcgctcgct cgctcagctg cactctatgg | 3660 |
| ctcaggtgca gtgtcttgag cttttctctgc tgctactgga tcacatttgc tttgtgttgt | 3720 |
| tactgctgtc cctccgctgg gttcctgctg tcattaaaag gtgtcgctgt ccccacccgg | 3780 |
| tgtcctttct agccatctac tgtaagttgt gcattcaaat taagattaag gaaaaacata | 3840 |
| ttttaaatg agtaccttga tgcgcaataa aaaaagaca tttctttttt taatgtggtt | 3900 |
| tatctgtgat ttaaaaataa aaaacacatg aacttacaat atttaaaaca tgctacaatc | 3960 |
| agtgctgaaa atagtatttt ccccgtttta tgcattttac tattgtaaat atgttttcta | 4020 |
| aatcaaatac tttaaaagaa gaaatgttga atttataaat gctatttact ttttattt | 4080 |
| actttataa taaagtaca agcacattgt tgacctaaaa aaaaaaaa | 4128 |

<210> SEQ ID NO 7
<211> LENGTH: 3625
<212> TYPE: DNA
<213> ORGANISM: Homo sapiens

<400> SEQUENCE: 7

| | |
|---|---|
| ggccaccgga gcggcccggc gacgatcgct gacagcttcc cctgcccttc ccgtcggtcg | 60 |
| ggccgccagc cgccgcagcc ctcggcctgc acgcagccac cggccccgct cccggagccc | 120 |
| agcgccgccg aggccgcagc cgcccggcca gtaaggcggc gccgcccgcg gccaccgcgg | 180 |
| gccctgccgt tccctccgcc gcgctgcgcc atggcgcggc gctgactggc ctggcccggc | 240 |
| cccgccgcgc tcccgctcgc cccgaccccgc actcgggccc gccggggctc cggcctgccg | 300 |
| ccgcctcttc cttctccagc cggcaggccc cgccgcttag gagggagagc ccacccgcgc | 360 |
| caggaggccg aacgcggact cgccaccegg cttcagaatg gcagaagatg atccatattt | 420 |
| gggaaggcct gaacaaatgt ttcatttgga tccttctttg actcatacaa tatttaatcc | 480 |
| agaagtattt caaccacaga tggcactgcc aacagatggc ccataccttc aaatattaga | 540 |
| gcaacctaaa cagagaggat ttcgtttccg ttatgtatgt gaaggcccat cccatggtgg | 600 |
| actacctggt gcctctagtg aaaagaacaa gaagtcttac cctcaggtca aaatctgcaa | 660 |
| ctatgtggga ccagcaaagg ttattgttca gttggtcaca aatggaaaaa atatccacct | 720 |
| gcatgcccac agcctggtgg gaaaacactg tgaggatggg atctgcactg taactgctgg | 780 |
| acccaaggac atggtggtcg gcttcgcaaa cctgggtata cttcatgtga caagaaaaa | 840 |
| agtatttgaa acactggaag cacgaatgac agaggcgtgt ataaggggct ataatcctgg | 900 |
| actcttggtg caccctgacc ttgcctattt gcaagcagaa ggtggagggg accggcagct | 960 |
| gggagatcgg gaaaagagc taatccgcca agcagctctg cagcagacca aggagatgga | 1020 |
| cctcagcgtg gtgcggctca tgtttacagc ttttcttccg gatagcactg gcagcttcac | 1080 |
| aaggcgcctg gaacccgtgg tatcagacgc catctatgac agtaaagccc ccaatgcatc | 1140 |

```
caacttgaaa attgtaagaa tggacaggac agctggatgt gtgactggag gggaggaaat    1200
ttatcttctt tgtgacaaag ttcagaaaga tgacatccag attcgatttt atgaagagga    1260
agaaaatggt ggagtctggg aaggatttgg agattttcc cccacagatg ttcatagaca     1320
atttgccatt gtcttcaaaa ctccaaagta taaagatatt aatattacaa aaccagcctc    1380
tgtgtttgtc cagcttcgga ggaaatctga cttggaaact agtgaaccaa aacctttcct    1440
ctactatcct gaaatcaaag ataaagaaga agtgcagagg aaacgtcaga agctcatgcc    1500 caattttcg gatagtttcg gcggtggtag tggtgccgga gctggaggcg gaggcatgtt     1560
tggtagtggc ggtggaggag ggggcactgg aagtacaggt ccagggtata gcttcccaca    1620
ctatggattt cctacttatg gtgggattac tttccatcct ggaactacta aatctaatgc    1680
tgggatgaag catggaacca tggacactga atctaaaaag gaccctgaag ttgtgacaa     1740 aagtgatgac aaaaacactg taaacctctt tgggaaagtt attgaaacca cagagcaaga    1800
tcaggagccc agcgaggcca ccgttgggaa tggtgaggtc actctaacgt atgcaacagg    1860
aacaaaagaa gagagtgctg gagttcagga taacctcttt ctagaaagg ctatgcagct     1920 tgcaaagagg catgccaatg ccctttttcga ctacgcggtg acaggagacg tgaagatgct   1980
gctggccgtc cagcgccatc tcactgctgt gcaggatgaa aatggggaca gtgtcttaca    2040
cttagcaatc atccaccttc attctcaact tgtgagggat ctactagaag tcacatctgg    2100
tttgatttct gatgacatta tcaacatgag aaatgatctg taccgacgc ccttgcactt     2160 ggcagtgatc actaagcagg aagatgtggt ggaggatttg ctgagggctg ggccgacct     2220 gagccttctg gaccgcttgg gtaactctgt tttgcaccta gctgccaaag aaggacatga    2280
taaagttctc agtatcttac tcaagcacaa aaaggcagca ctacttcttg accaccccaa    2340
cggggacggt ctgaatgcca ttcatctagc catgatgagc aatagcctgc catgtttgct    2400
gctgctggtg gccgctgggg ctgacgtcaa tgctcaggag cagaagtccg gcgcacagc     2460 actgcacctg gctgtggagc acgacaacat ctcattggca ggctgcctgc tcctggaggg    2520
tgatgcccat gtggacagta ctacctacga tggaaccaca cccctgcata tagcagctgg    2580
gagagggtcc accaggctgg cagctcttct caaagcagca ggagcagatc ccctggtgga    2640
gaactttgag cctctctatg acctggatga ctcttgggaa aatgcaggag aggatgaagg    2700
agttgtgcct ggaaccacgc ctctagatat ggccaccagc tggcaggtat ttgacatatt    2760
aaatgggaaa ccatatgagc cagagtttac atctgatgat ttactagcac aaggagacat    2820
gaaacagctg gctgaagatg tgaagctgca gctgtataag ttactagaaa ttcctgatcc    2880
agacaaaaac tgggctactc tggcgcagaa attaggtctg gggatactta ataatgcctt    2940
ccggctgagt cctgctccct tccaaaacac ttatgagtct ctgggggtac                3000
agtcagagag ctggtggagg ccctgagaca aatgggctac accgaagcaa ttgaagtgat    3060
ccaggcagcc tccagcccag tgaagaccac ctctcaggcc cactcgctgc ctctctcgcc    3120
tgcctccaca aggcagcaaa tagacgagct ccgagacagt gacagtgtct gcgacacggg    3180
cgtggagaca tccttccgca aactcagctt taccgagtct ctgaccagtg gtgcctcact    3240
gctaactctc aacaaaatgc cccatgatta tgggcaggaa ggacctctag aaggcaaaat    3300
ttagcctgct gacaatttcc cacaccgtgt aaaccaaagc cctaaaattc cactgcgttg    3360
tccacaagac agaagctgaa gtgcatccaa aggtgctcag agagccggcc cgcctgaatc    3420
attctcgatt taactcgaga cctttcaac ttggcttcct ttcttggttc ataaatgaat     3480
tttagtttgg ttcacttaca gatagtatct agcaatcaca acactggctg agcggatgca    3540
```

```
tctggggatg aggttgctta ctaagctttg ccagctgctg ctggatcaca gctgctttct    3600
gttgtcattg ctgttgtccc tctgc                                         3625

<210> SEQ ID NO 8
<211> LENGTH: 13
<212> TYPE: DNA
<213> ORGANISM: Artificial
<220> FEATURE:
<223> OTHER INFORMATION: target template

<400> SEQUENCE: 8
cgcgggagac gga                                                        13

<210> SEQ ID NO 9
<211> LENGTH: 13
<212> TYPE: DNA
<213> ORGANISM: Artificial
<220> FEATURE:
<223> OTHER INFORMATION: target template

<400> SEQUENCE: 9
gacgtctctt cga                                                        13

<210> SEQ ID NO 10
<211> LENGTH: 13
<212> TYPE: DNA
<213> ORGANISM: Artificial
<220> FEATURE:
<223> OTHER INFORMATION: target template

<400> SEQUENCE: 10
gcgccctctg cct                                                        13

<210> SEQ ID NO 11
<211> LENGTH: 13
<212> TYPE: DNA
<213> ORGANISM: Artificial
<220> FEATURE:
<223> OTHER INFORMATION: target template

<400> SEQUENCE: 11
ctgcagagaa gct                                                        13

<210> SEQ ID NO 12
<211> LENGTH: 69
<212> TYPE: DNA
<213> ORGANISM: Artificial
<220> FEATURE:
<223> OTHER INFORMATION: Lrba/SD/loxP portion of Lrba BAC subclone
      plasmid

<400> SEQUENCE: 12
tttctcgtga acgcgtcttc agggtgagtt tataacttcg tataatgtat gctatacgaa     60
gttatacgc                                                             69

<210> SEQ ID NO 13
<211> LENGTH: 84
<212> TYPE: DNA
<213> ORGANISM: Artificial
<220> FEATURE:
<223> OTHER INFORMATION: STOP/loxP portion of Lrba BAC subclone plasmid

<400> SEQUENCE: 13
tgctctaggg ggtatcccca cgtaatacga ctcactatag ggctcgagat aacttcgtat     60
```

```
aatgtatgct atacgaagtt atgc                                             84

<210> SEQ ID NO 14
<211> LENGTH: 87
<212> TYPE: DNA
<213> ORGANISM: Artificial
<220> FEATURE:
<223> OTHER INFORMATION: Aqua/P2A/Lrba portion of Lrba BAC subclone
      plasmid

<400> SEQUENCE: 14
tacaaaggca gcggcgccac aaacttttca ctcctgaaac aggccgggga tgtagaggag      60
aaccccggcc ctatggctag tgaagac                                          87

<210> SEQ ID NO 15
<211> LENGTH: 10
<212> TYPE: DNA
<213> ORGANISM: Homo sapiens

<400> SEQUENCE: 15
ggactacccc                                                             10

<210> SEQ ID NO 16
<211> LENGTH: 10
<212> TYPE: DNA
<213> ORGANISM: Homo sapiens

<400> SEQUENCE: 16
aggactttcc                                                             10

<210> SEQ ID NO 17
<211> LENGTH: 10
<212> TYPE: DNA
<213> ORGANISM: Homo sapiens

<400> SEQUENCE: 17
ggggctcccc                                                             10

<210> SEQ ID NO 18
<211> LENGTH: 10
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t

<400> SEQUENCE: 18 gggrnwyycc                                                             10

<210> SEQ ID NO 19
<211> LENGTH: 34
<212> TYPE: DNA
<213> ORGANISM: Artificial
<220> FEATURE:
<223> OTHER INFORMATION: locus of Cre recombinase-mediated crossover

<400> SEQUENCE: 19
ataacttcgt atagcataca ttatacgaag ttat                                  34

<210> SEQ ID NO 20
<211> LENGTH: 34
<212> TYPE: DNA
<213> ORGANISM: Artificial
```

```
<220> FEATURE:
<223> OTHER INFORMATION: locus of Cre recombinase-mediated crossover

<400> SEQUENCE: 20
ataacttcgt ataatgtatg ctatacgaag ttat                              34

<210> SEQ ID NO 21
<211> LENGTH: 34
<212> TYPE: DNA
<213> ORGANISM: Artificial
<220> FEATURE:
<223> OTHER INFORMATION: locus of Cre recombinase-mediated crossover

<400> SEQUENCE: 21
tattgaagca tatcgtatgt aatatgcttc aata                              34

<210> SEQ ID NO 22
<211> LENGTH: 34
<212> TYPE: DNA
<213> ORGANISM: Artificial
<220> FEATURE:
<223> OTHER INFORMATION: locus of Cre recombinase-mediated crossover

<400> SEQUENCE: 22
tattgaagca tattacatac gatatgcttc aata                              34

<210> SEQ ID NO 23
<211> LENGTH: 14
<212> TYPE: DNA
<213> ORGANISM: Artificial
<220> FEATURE:
<223> OTHER INFORMATION: locus of Cre recombinase-mediated crossover

<400> SEQUENCE: 23
ataacttcgt atag                                                    14

<210> SEQ ID NO 24
<211> LENGTH: 20
<212> TYPE: DNA
<213> ORGANISM: Artificial
<220> FEATURE:
<223> OTHER INFORMATION: locus of Cre recombinase-mediated crossover

<400> SEQUENCE: 24
catacattat acgaagttat                                              20

<210> SEQ ID NO 25
<211> LENGTH: 14
<212> TYPE: DNA
<213> ORGANISM: Artificial
<220> FEATURE:
<223> OTHER INFORMATION: locus of Cre recombinase-mediated crossover

<400> SEQUENCE: 25
ataacttcgt ataa                                                    14

<210> SEQ ID NO 26
<211> LENGTH: 20
<212> TYPE: DNA
<213> ORGANISM: Artificial
<220> FEATURE:
<223> OTHER INFORMATION: locus of Cre recombinase-mediated crossover

<400> SEQUENCE: 26
tgtatgctat acgaagttat                                              20
```

```
<210> SEQ ID NO 27
<211> LENGTH: 20
<212> TYPE: DNA
<213> ORGANISM: Artificial
<220> FEATURE:
<223> OTHER INFORMATION: locus of Cre recombinase-mediated crossover

<400> SEQUENCE: 27
tattgaagca tatcgtatgt                                               20

<210> SEQ ID NO 28
<211> LENGTH: 14
<212> TYPE: DNA
<213> ORGANISM: Artificial
<220> FEATURE:
<223> OTHER INFORMATION: locus of Cre recombinase-mediated crossover

<400> SEQUENCE: 28
aatatgcttc aata                                                     14

<210> SEQ ID NO 29
<211> LENGTH: 20
<212> TYPE: DNA
<213> ORGANISM: Artificial
<220> FEATURE:
<223> OTHER INFORMATION: locus of Cre recombinase-mediated crossover

<400> SEQUENCE: 29
tattgaagca tattacatac                                               20

<210> SEQ ID NO 30
<211> LENGTH: 14
<212> TYPE: DNA
<213> ORGANISM: Artificial
<220> FEATURE:
<223> OTHER INFORMATION: locus of Cre recombinase-mediated crossover

<400> SEQUENCE: 30
gatatgcttc aata                                                     14

<210> SEQ ID NO 31
<211> LENGTH: 83
<212> TYPE: DNA
<213> ORGANISM: Artificial
<220> FEATURE:
<223> OTHER INFORMATION: sequence at 5' junction of TCLC cassette
      insertion

<400> SEQUENCE: 31
tttctcgtga acgcgtcttc agggtgagtt tataacttcg tataatgtat gctatacgaa    60
gttatacgcg ttgacattga tta                                           83
```